(12) United States Patent
Dobson

(10) Patent No.: US 8,404,839 B2
(45) Date of Patent: *Mar. 26, 2013

(54) CRYSTALLINE 4-(3-CHLORO-2-FLUOROANILINO)-7 METHOXY-6-{[1-(N-METHYLCARBAMOYL METHYL)PIPERIDIN-4-YL]OXY} QUINAZOLINE DIFUMARATE FORM A

(75) Inventor: Andrew Hornby Dobson, Macclesfield (GB)

(73) Assignee: Astrazeneca AB, Alderley Park, Macclesfield, Cheshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/273,392

(22) Filed: Oct. 14, 2011

(65) Prior Publication Data
US 2012/0035363 A1    Feb. 9, 2012

Related U.S. Application Data

(63) Continuation of application No. 12/463,624, filed on May 11, 2009, now Pat. No. 8,088,782.

(60) Provisional application No. 61/110,637, filed on Nov. 3, 2008, provisional application No. 61/052,706, filed on May 13, 2008.

(51) Int. Cl.
*A61K 31/517*    (2006.01)

(52) U.S. Cl. .................................................. 544/293

(58) Field of Classification Search .................. 544/293
See application file for complete search history.

(56) References Cited

U.S. PATENT DOCUMENTS

| | | | |
|---|---|---|---|
| 3,985,749 A | 10/1976 | Foster | |
| 4,332,420 A | 6/1982 | Coski | |
| 4,335,127 A | 6/1982 | Vandenberk et al. | |
| 4,640,920 A | 2/1987 | Boyle et al. | |
| 4,921,863 A | 5/1990 | Sugimoto et al. | |
| 5,252,586 A | 10/1993 | Cain et al. | |
| 5,264,417 A * | 11/1993 | Okada et al. | 514/1.6 |
| 5,405,843 A | 4/1995 | Fukazawa et al. | |
| 5,457,105 A | 10/1995 | Barker | |
| 5,616,582 A | 4/1997 | Barker | |
| 5,721,237 A | 2/1998 | Myers et al. | |
| 5,747,498 A | 5/1998 | Schnur et al. | |
| 5,770,599 A | 6/1998 | Gibson | |
| 5,770,603 A | 6/1998 | Gibson | |
| 5,795,909 A * | 8/1998 | Shashoua et al. | 514/449 |
| 5,821,246 A | 10/1998 | Brown et al. | |
| 5,866,572 A | 2/1999 | Barker et al. | |
| 5,929,080 A | 7/1999 | Frost et al. | |
| 5,962,458 A | 10/1999 | Lohmann et al. | |
| 6,004,967 A | 12/1999 | McMahon et al. | |
| 6,046,206 A | 4/2000 | Pamukcu et al. | |
| 6,117,433 A | 9/2000 | Edens et al. | |
| 6,126,917 A | 10/2000 | Mishani et al. | |
| 6,177,433 B1 | 1/2001 | Uckun et al. | |
| 6,225,318 B1 | 5/2001 | Sobolov-Jaynes et al. | |
| 6,262,054 B1 | 7/2001 | Fennelly et al. | |
| 6,297,258 B1 | 10/2001 | Wissner et al. | |
| 6,313,130 B1 | 11/2001 | Uckun et al. | |
| 6,326,373 B1 | 12/2001 | Uckun et al. | |
| 6,384,223 B1 | 5/2002 | Gletsos | |
| 6,562,319 B2 | 5/2003 | Mishani et al. | |
| 6,617,329 B2 | 9/2003 | Himmelsbach et al. | |
| 6,627,651 B1 | 9/2003 | Shiraishi et al. | |
| 6,653,305 B2 | 11/2003 | Himmelsbach et al. | |
| 6,656,946 B2 | 12/2003 | Himmelsbach et al. | |
| 6,673,803 B2 | 1/2004 | Thomas et al. | |
| 6,740,651 B2 | 5/2004 | Himmelsbach et al. | |
| 6,900,206 B2 * | 5/2005 | Kadow et al. | 514/235.2 |
| 6,924,285 B2 | 8/2005 | Himmelsbach et al. | |
| 6,972,288 B1 | 12/2005 | Himmelsbach et al. | |
| 7,019,012 B2 | 3/2006 | Himmelsbach et al. | |
| 7,119,084 B2 | 10/2006 | Himmelsbach et al. | |
| 7,148,230 B2 | 12/2006 | Bradbury et al. | |
| 7,160,981 B2 | 1/2007 | La Thangue et al. | |
| 7,220,750 B2 | 5/2007 | Himmelsbach et al. | |
| 7,252,971 B2 * | 8/2007 | Benson et al. | 435/69.1 |
| 7,294,629 B2 | 11/2007 | Kitano et al. | |

(Continued)

FOREIGN PATENT DOCUMENTS

| | | |
|---|---|---|
| CA | 2086968 | 7/1993 |
| CA | 2375259 | 12/2000 |

(Continued)

OTHER PUBLICATIONS

Arnold et al. Epidermal growth factor receptor tyrosine kinase inhibitors:present and future role in gastrointestinal cancer treatment:A review. 2006, Oncologist, 11,602-611.*

(Continued)

*Primary Examiner* — Brian McDowell
(74) *Attorney, Agent, or Firm* — Astrazeneca AB

(57) ABSTRACT

4-(3-chloro-2-fluoroanilino)-7 methoxy-6-{[1-(N-methyl-carbamoylmethyl)piperidin-4-yl]oxy}quinazoline

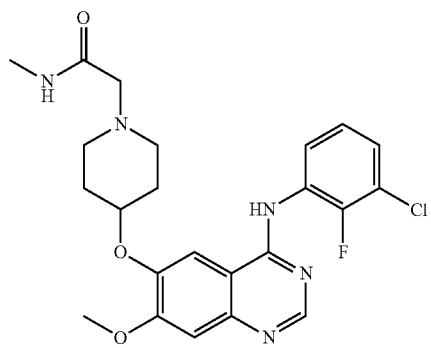

difumarate, pharmaceutical compositions containing the difumarate, the use of the difumarate in the treatment of hyperproliferative disorders such as cancer and processes for the manufacture of the difumarate are described.

6 Claims, 23 Drawing Sheets

U.S. PATENT DOCUMENTS

| | | |
|---|---|---|
| 2002/0049197 A1 | 4/2002 | Himmelsbach et al. |
| 2002/0082270 A1 | 6/2002 | Himmelsbach et al. |
| 2002/0082271 A1 | 6/2002 | Himmelsbach et al. |
| 2002/0128553 A1 | 9/2002 | Mishani et al. |
| 2002/0169180 A1 | 11/2002 | Himmelsbach et al. |
| 2002/0173509 A1 | 11/2002 | Himmelsbach et al. |
| 2002/0173646 A1 | 11/2002 | Thomas et al. |
| 2002/0177601 A1 | 11/2002 | Himmelsbach et al. |
| 2003/0149062 A1 | 8/2003 | Jung et al. |
| 2003/0158196 A1 | 8/2003 | Jung et al. |
| 2004/0044014 A1 | 3/2004 | Himmelsbach et al. |
| 2004/0048880 A1 | 3/2004 | Himmelsbach et al. |
| 2004/0053972 A1 | 3/2004 | Nara et al. |
| 2004/0176361 A1 | 9/2004 | Fujio et al. |
| 2004/0192664 A1 | 9/2004 | Kunz et al. |
| 2004/0198997 A1 | 10/2004 | Scholz et al. |
| 2005/0019375 A1 | 1/2005 | Artisa et al. |
| 2005/0043395 A1 | 2/2005 | Wedge |
| 2005/0130995 A1 | 6/2005 | Nishino et al. |
| 2005/0148607 A1 | 7/2005 | Suzuki et al. |
| 2005/0165035 A1 | 7/2005 | Bradbury et al. |
| 2005/0182043 A1 | 8/2005 | Himmelsbach et al. |
| 2005/0215574 A1 | 9/2005 | Bradbury et al. |
| 2006/0014832 A1* | 1/2006 | Breitenbach et al. ......... 514/540 |
| 2006/0167026 A1 | 7/2006 | Nawa et al. |
| 2006/0188501 A1 | 8/2006 | Homma et al. |
| 2006/0223794 A1* | 10/2006 | Bourghol Hickey et al. . 514/220 |
| 2006/0223820 A1* | 10/2006 | Brand et al. ............. 514/253.07 |
| 2006/0270672 A1 | 11/2006 | Himmelsbach et al. |
| 2007/0037837 A1 | 2/2007 | Hennequin et al. |
| 2007/0043010 A1 | 2/2007 | Bradbury et al. |
| 2007/0099943 A1 | 5/2007 | Bradbury et al. |
| 2008/0076415 A1 | 3/2008 | Kang et al. |
| 2008/0096881 A1 | 4/2008 | Hennequin et al. |
| 2008/0269487 A1 | 10/2008 | Bradbury et al. |
| 2008/0279932 A1* | 11/2008 | Reber et al. ................... 424/464 |
| 2009/0312313 A1 | 12/2009 | Shimizu et al. |

FOREIGN PATENT DOCUMENTS

| | | |
|---|---|---|
| CA | 2417050 | 3/2002 |
| CA | 2417652 | 1/2003 |
| CA | 2417897 | 1/2003 |
| CA | 2417907 | 1/2003 |
| CA | 2417042 | 3/2003 |
| EP | 0288563 | 2/1988 |
| EP | 0326330 | 2/1989 |
| EP | 566226 | 10/1993 |
| EP | 0607439 | 7/1994 |
| EP | 0602851 | 10/1996 |
| EP | 0520722 | 6/1997 |
| EP | 078772 | 8/1997 |
| EP | 0837063 | 4/1998 |
| EP | 0635507 | 9/1999 |
| EP | 1230919 | 8/2002 |
| EP | 1283039 | 2/2003 |
| EP | 1369418 | 12/2003 |
| GB | 2033894 | 5/1980 |
| GB | 2160201 | 12/1985 |
| GB | 2295387 | 5/1996 |
| JP | 11189586 | 7/1999 |
| JP | 2003246780 | 9/2003 |
| WO | WO 88/02365 | 4/1988 |
| WO | WO 92/14746 | 9/1992 |
| WO | WO 92/20642 | 11/1992 |
| WO | WO 93/08170 | 4/1993 |
| WO | WO 93/17682 | 9/1993 |
| WO | WO 94/27965 | 8/1994 |
| WO | WO 95/00146 | 1/1995 |
| WO | WO 95/03283 | 2/1995 |
| WO | WO 95/15758 | 6/1995 |
| WO | WO 95/24190 | 9/1995 |
| WO | WO 96/09294 | 3/1996 |
| WO | WO 96/15118 | 5/1996 |
| WO | WO 96/16960 | 6/1996 |
| WO | WO 96/30347 | 10/1996 |
| WO | WO 96/33977 | 10/1996 |
| WO | WO 96/33978 | 10/1996 |
| WO | WO 96/33979 | 10/1996 |
| WO | WO 96/33980 | 10/1996 |
| WO | WO 96/33981 | 10/1996 |
| WO | WO 96/39145 | 12/1996 |
| WO | WO 97/03069 | 1/1997 |
| WO | WO 97/11692 | 4/1997 |
| WO | WO 97/18813 | 5/1997 |
| WO | WO 97/22596 | 6/1997 |
| WO | WO 97/30034 | 8/1997 |
| WO | WO 97/30035 | 8/1997 |
| WO | WO 97/30044 | 8/1997 |
| WO | WO 97/32856 | 9/1997 |
| WO | WO 97/38983 | 10/1997 |
| WO | WO 97/38994 | 10/1997 |
| WO | WO 97/42187 | 11/1997 |
| WO | WO 98/02434 | 1/1998 |
| WO | WO 98/13354 | 4/1998 |
| WO | WO 98/38984 | 9/1998 |
| WO | WO 98/50370 | 11/1998 |
| WO | WO 98/50038 | 12/1998 |
| WO | WO 99/06378 | 2/1999 |
| WO | WO 99/09016 | 2/1999 |
| WO | WO 99/10349 | 3/1999 |
| WO | WO 99/24037 | 5/1999 |
| WO | WO 99/35132 | 7/1999 |
| WO | WO 99/61428 | 12/1999 |
| WO | WO 00/00202 | 1/2000 |
| WO | WO 00/06555 | 2/2000 |
| WO | WO 00/10981 | 3/2000 |
| WO | WO 00/12497 | 3/2000 |
| WO | WO 00/09481 | 4/2000 |
| WO | WO 00/18740 | 4/2000 |
| WO | WO 00/19788 | 4/2000 |
| WO | WO 00/20402 | 4/2000 |
| WO | WO 00/24718 | 5/2000 |
| WO | WO 00/44728 | 8/2000 |
| WO | WO 00/47212 | 8/2000 |
| WO | WO 00/51587 | 9/2000 |
| WO | WO 00/51991 | 9/2000 |
| WO | WO 00/55141 | 9/2000 |
| WO | WO 00/55162 | 9/2000 |
| WO | WO 00/56338 | 9/2000 |
| WO | WO 00/56720 | 9/2000 |
| WO | WO 00/68203 | 11/2000 |
| WO | WO 00/72489 | 12/2000 |
| WO | WO 00/73260 | 12/2000 |
| WO | WO 00/78735 | 12/2000 |
| WO | WO 01/04102 | 1/2001 |
| WO | WO 01/07432 | 1/2001 |
| WO | WO 01/12227 | 2/2001 |
| WO | WO 01/21160 | 3/2001 |
| WO | WO 01/21594 | 3/2001 |
| WO | WO 01/21595 | 3/2001 |
| WO | WO 01/21596 | 3/2001 |
| WO | WO 01/21597 | 3/2001 |
| WO | WO 01/32155 | 5/2001 |
| WO | WO 01/32632 | 5/2001 |
| WO | WO 01/32651 | 5/2001 |
| WO | WO 01/45641 | 6/2001 |
| WO | WO 01/64642 | 9/2001 |
| WO | WO 01/66099 | 9/2001 |
| WO | WO 01/76586 | 10/2001 |
| WO | WO 01/77085 | 10/2001 |
| WO | WO 01/94341 | 12/2001 |
| WO | WO 01/98277 | 12/2001 |
| WO | WO 02/05791 | 1/2002 |
| WO | WO 02/16352 | 2/2002 |
| WO | WO 02/17712 | 3/2002 |
| WO | WO 02/18351 | 3/2002 |
| WO | WO 02/18370 | 3/2002 |
| WO | WO 02/18372 | 3/2002 |
| WO | WO 02/18373 | 3/2002 |
| WO | WO 02/18376 | 3/2002 |
| WO | WO 02/20020 | 3/2002 |
| WO | WO 02/24684 | 3/2002 |
| WO | WO 02/30358 | 4/2002 |
| WO | WO 02/30924 | 4/2002 |
| WO | WO 02/34711 | 5/2002 |
| WO | WO 02/34744 | 5/2002 |

| | | |
|---|---|---|
| WO | WO 02/41882 | 5/2002 |
| WO | WO 02/44166 | 6/2002 |
| WO | WO 02/48117 | 6/2002 |
| WO | WO 02/50043 | 6/2002 |
| WO | WO 02/056882 | 7/2002 |
| WO | WO 02/062767 | 8/2002 |
| WO | WO 02/066445 | 8/2002 |
| WO | WO 02/068409 | 9/2002 |
| WO | WO 02/073235 | 9/2002 |
| WO | WO 02/076976 | 10/2002 |
| WO | WO 02/092577 | 11/2002 |
| WO | WO 02/092578 | 11/2002 |
| WO | WO 02/092579 | 11/2002 |
| WO | WO 02/094760 | 11/2002 |
| WO | WO 03/000188 | 1/2003 |
| WO | WO 03/031406 | 4/2003 |
| WO | WO 03/039551 | 5/2003 |
| WO | WO 03/040108 | 5/2003 |
| WO | WO 03/040109 | 5/2003 |
| WO | WO 03/045395 | 6/2003 |
| WO | WO 03/049740 | 6/2003 |
| WO | WO 03/064413 | 8/2003 |
| WO | WO 03/082290 | 10/2003 |
| WO | WO 03/082831 | 10/2003 |
| WO | WO 03/096615 | 11/2003 |
| WO | WO 03/097086 | 11/2003 |
| WO | WO 03/099276 | 12/2003 |
| WO | 20040006846 | 1/2004 |
| WO | 20040013091 | 2/2004 |
| WO | WO 2004/010929 | 2/2004 |
| WO | WO 2004/064718 | 8/2004 |
| WO | WO 2004/072038 | 8/2004 |
| WO | WO 2004/085385 | 10/2004 |
| WO | WO 2004/093880 | 11/2004 |
| WO | WO 2004/096224 | 11/2004 |
| WO | WO 2004/096226 | 11/2004 |
| WO | WO 2005/001053 | 1/2005 |
| WO | WO 2005/003325 | 1/2005 |
| WO | WO 2005/012290 | 2/2005 |
| WO | WO 2005/016347 | 2/2005 |
| WO | WO 2005/026150 | 3/2005 |
| WO | WO 2005/026151 | 3/2005 |
| WO | WO 2005/026152 | 3/2005 |
| WO | WO 2005/026156 | 3/2005 |
| WO | WO 2005/026157 | 3/2005 |
| WO | WO 2005/028469 | 3/2005 |
| WO | WO 2005/028470 | 3/2005 |
| WO | WO 2005/030140 | 4/2005 |
| WO | WO 2005/030757 | 4/2005 |
| WO | WO 2005/030765 | 5/2005 |
| WO | WO 2005/041973 | 5/2005 |
| WO | WO 2005/051923 | 6/2005 |
| WO | WO 2005/061488 | 7/2005 |
| WO | WO 2005/075439 | 8/2005 |
| WO | WO 2005/118572 | 12/2005 |
| WO | WO 03/045364 | 6/2006 |
| WO | WO 2006/064196 | 6/2006 |
| WO | WO 2006/090163 | 8/2006 |
| WO | WO 2006/092573 | 9/2006 |
| WO | WO 2006/092574 | 9/2006 |
| WO | WO 2006/117521 | 11/2006 |
| WO | WO 2006/117523 | 11/2006 |
| WO | WO 2007/034114 | 3/2007 |
| WO | WO 2007/034143 | 3/2007 |
| WO | WO 2007/054551 | 5/2007 |
| WO | WO 2007/063291 | 6/2007 |
| WO | WO 2007/063293 | 6/2007 |
| WO | WO 2007/066185 | 6/2007 |
| WO | WO 2008/154469 | 12/2008 |
| WO | WO 2009/138779 | 11/2009 |
| WO | WO 2009/138780 | 11/2009 |
| WO | WO 2009/138781 | 11/2009 |
| WO | WO 2010/061208 | 6/2010 |
| WO | WO 2010/122340 | 10/2010 |

OTHER PUBLICATIONS

Alferez et al., "Inhibiting Signaling by erbB Receptor Tyrosine Kinases with AZD8931, a Potent Reversible small Molecule Inhibitor, Reduces Intestinal Adenoma Formation in the ApcMin/+ Mouse Model", EORTC-NCI-AACR (2010), Abstract 471.

Alferez et al., "Inhibiting Signaling by erbB Receptor Tyrosine Kinases with AZD8931, a Potent Reversible small Molecule Inhibitor, Reduces Intestinal Adenoma Formation in the ApcMin/+ Mouse Model", EORTC-NCI-AACR (2010), Poster.

Ballard et al., "5-Substituted 4-anilinoquinazolines as potent, selective and orally active inhibitors of erbB2 receptor tyrosine kinase", Bioorganic & Medicinal Chemistry Letters 15(19): 4226-4229 (2005).

Ballard et al., "Inhibitors of epidermal growth factor receptor tyrosine kinase: Novel C-5 substituted anilinoquinazolines designed to target the ribose pocket", Bioorganic & Medicinal Chemistry Letters 16(6): 1633-1637 (2006).

Ballard et al., "Inhibitors of epidermal growth factor receptor tyrosine kinase: Optimization of potency and in vivo pharmacokinets", Bioorganic & Medicinal Chemistry Letters 16(18): 4908-4912 (2006).

Barker et al., "Studies Leading to the Identification ofZD1839 (Iressa™): An Orally Active, Selective Epidermal Growth Factor Receptor Tyrosine Kinase Inhibitor Targeted to the Treatment of Cancer", Bioorg. Med. Chem. Lett. 11(14): 1911-1914 (2001).

Blowers "AZD8931", IASLC Annual Targeted Therapies of the Treatment of Lung Cancer Meeting (2011), Santa Monica, CA, PowerPoint Presentation.

Bridges et al., "Tyrosine kinase inhibitors. 8. An unusually steep structure-activity relationship for analogues of 4-(3-bromoanilino)-6,7-dimethoxyquinazoline (PD 153035), a potent inhibitor of the epidermal growth factor receptor", 1. Med. Chem. 39: 267-276 (1996).

Chen et al., "Eludicating inhibitory models of the inhibitors of epidermal growth factor receptor by docking and 3D-QSAR", Bioorganic and Medicinal Chemistry 12: 2409-2417 (2004).

Ciardiello et al., "Phase II study of gefitinib in combination with docetaxel as first-line therapy in metastic breast cancer", British Journal of Cancer 94(11): 1604-1609 (2006).

Communication from European Patent Office dated Mar. 9, 2006, in EP App. No. 03710015.3, the European counterpart of the U.S. Appl. No. 10/508,675.

Communication from European Patent Office in EP App. No. 03710015.3, the European counterpart of the present application, U.S. Appl. No. 10/508,675, dated Sep. 22, 2006.

Communication from European Patent Office dated May 27, 2005, in EP App. No. 03710015.3, the European counterpart of U.S. Appl. No. 10/508,675.

Corrected version of Examination report in Singapore App. No. 200601647-1, the Singapore counterpart to the present application dated Sep. 5, 2008.

Cristofanilli et al., "Exploratory Subset Analysis According to Prior Endocrine Treatment of Two Randomized Phase II Trials Comparing Gefitinib (G) with Placebo (P) in Combination with Tamoxifen (T) or Anastrozole (A) in Hormone Receptor-Positive (HR+) Metastatic Breast Cancer (MBC)". J Clin. Oncol. (2009), vol. 27, 15s, Abstract 1014.

*Daiichi Sankyo Company, Ltd. et al. v. Matrix Laboratories, Ltd., et al.*, Appeal from the US District Court for the District of NJ in Case No. 06-CV-03462, 2009-1511, Decided Sep. 9, 2010.

Decision in Patent Interferences 105,595 McK and 105,596 McK dated Jun. 17, 2008.

Dennison et al., "A phase II clinical trial of ZD1839 (Iressa (TM)) in combination with docetaxel as first-line treatment in patients with advanced breast cancer", Investigational New Drugs; The Journal of New Anticancer Agents, Kluwer Academic Publishers 25(6): 545-551 (2007).

Gazit et al., "Tyrophostins IV—Highly Potent Inhibitors . . . Relationship Study of 4-Anilidoquinazolines", Bioorganic & Medicinal Chemistry 4(8): 1203-1207 (1996).

Ghosh et al., "Structure-based design of potent inhibitors of EGF-receptor tyrosine kinase as anticancer agents", Anti-Cancer Drug Design 14: 403-410 (1999).

Grunwald et al., "Developing Inhibitors of the Epidermal Growth Factor Receptor for Cancer Treatment", J. National Cancer Institute 95(12): 851-887 (2003).

Harris et al., "Selective alkylation of a 6,7-dihydroxyquinazoline", Tetrahedron Letters 46(45): 7715-7719 (2005).

Harris et al., Poster presented at the XXII Colloquium on Heterocyclic Chemistry (XXII ECHC-2006) in Bari, Italy, on Sep. 2-6, 2006.

Harris et al., "Facile synthesis of 7-amino anilinoquinazolines via direct amination of the quinazoline core", Tetrahedron Letters 46(43): 7381-7384 (2005).

Hennequin et al., "Novel 4-anilinoquinazolines with C-6 carbon-linked side chains: Synthesis and structure-activity relationship of a series of potent, orally active, EGF receptor tyrosine kinase inhibitors", Bioorganic & Medicinal Chemistry Letters 16(10): 2672-2676 (2006).

Hennequin et al., "Design and structure-activity relationship of a new class of potent VEGF receptor tyrosine kinase inhibitors", J. Med. Chem. 42: 5369-5389 (1999).

Hennequin et al., "Novel 4-anilinoquinazolines with C-7 basis side chains. Design and structure activity relationship of a series of potent, orally active, VEGF receptor tyrosine kinase inhibitors", J. Med. Chem. 45(6): 1300-1312 (2002).

Hickinson et al., "AZD8931, an Equipotent, Reversible Inhibitor of Signaling by Epidermal Growth Factor Receptor, ERBB2 (HER2), and ERBB3: A Unique Agent for Simultaneous ERBB Receptor Blockage in Cancer", Clinical Cancer Research 16: 1159-1169 (2010).

Keilholz et al. "Phase I Dose-Finding Study of Monotherapy with AZD8931, an Inhibitor of erbB 1, 2 and 3 Signaling, in Patients with Advanced Solid Tumors". ASCO (2011), Poster.

Keilholz et al. "Phase I Dose-Finding Study of Monotherapy with AZD8931, an Inhibitor of erbB 1, 2 and 3 Signaling, in Patients with Advanced Solid Tumors". J Clin Oncol. (2011), vol. 29, Abstract 3097.

Klinowska et al. "AZD8931, an Equipotent, Reversible Inhibitor of erbBl, erbB2 and erbB3 Receptor Signaling: Characterisation of Pharmacological Profile". European Journal of Cancer Supplements (2009), vol. 7, No. 2, 127.

Kurebayashi et al., "Inhibition of HER1 signaling pathway enhances antitumor effect of endocrine therapy in breast cancer", 11(1): 38-41 (2004).

Liu et al., "Blockage of epidermal growth factor receptor by quinazoline tyrosine kinase inhibitors suppresses growth of human hepatocellular carcinoma", Cancer Letters 248: 32-40 (2007).

Lopez-Martin et al. "Phase I Dose-Finding Study of AZD8931, an Inhibitor of erbB 1, 2 and 3 Receptor Signaling, in Combination with Paclitaxel". J Clin. Oncol. (2011), vol. 29, Abstract 3105.

Lopez Martin et al. "Phase I Dose-Finding Study of AZD8931, an Inhibitor of erbB 1, 2 and 3 Receptor Signaling, in Combination with Paclitaxel". ASCO (2011), Poster.

March, J. Advanced Organic Chemistry—Reactions, Mechanisms, and Structure, 4th Ed., John Wiley & Sons, NY, NY 357-362 (1992).

Marshall et al. "Evaluation of AZD8931, an Equipotent Inhibitor of erbB 1, erbB2 and erbB3 Receptor Signaling, on Ligand Stimulated Breast Cancer Cell Lines with Differing Levels of erbB2 Expression". SABCS (2009), Abstract 5059.

Mendelsohn "Targeting the Epidermal Growth Factor Receptor for Cancer Therapy", Journal of Clinical Oncology 29(18s): 2s-13s (2002).

Mendelsohn et al., "Status of Epidermal Growth Factor Receptor Antagonists in the Biology and Treatment of Cancer", Journal of Clinical Oncology 21(14): 2787-2799 (2003).

Myers et al., "The preparation and SAR of 4-(aniline),4-(phenoxy), and 4-(thiophenoxy)-quinazolines: inhibitors of p56lck and EGF-R tyrosine kinase activity", Bioorg. Med. Chem. Lett. 7(4): 417-420 (1997).

Normanno et al. "Target-based therapies in breast cancer: current status and future perspectives". Endocr. Relat. Cancer (2009), vol. 16(3): 675-702.

Notices of Allowability and Allowance dated Jul. 26, 2006, in copending U.S. Appl. No. 10/857,342.

Office Action in copending U.S. Appl. No. 10/571,991 mailed Aug. 19, 2008.

Office Action in copending U.S. Appl. No. 10/572,048 mailed Oct. 31, 2008.

Office Action in copending U.S. Appl. No. 10/571,991 mailed Jan. 6, 2009.

Office Action in copending U.S. Appl. No. 12/147,250 mailed Aug. 17, 2009.

Office Action in copending U.S. Appl. No. 11/636,549 mailed Sep. 29, 2009.

Office Action in copending U.S. Appl. No. 10/572,048 mailed Jan. 5, 2010.

Office Action in copending U.S. Appl. No. 10/572,048 mailed Jun. 9, 2009.

Office Action in copending U.S. Appl. No. 10/573,352 mailed Oct. 28, 2009.

Office Action in copending U.S. Appl. No. 10/573,352 mailed Mar. 5, 2009.

Office Action in Singapore App. No. 200601647-1, the Singapore counterpart to the present application dated Sep. 7, 2007.

Okubo et al., "Additive antitumour effect of the epidermal growth factor receptor tyrosine kinase inhibitor gefitinib (Iressa, ZD 1839) and the antioestrogen fulvestrant (Faslodex, ICI 18, 780) in breast cancer cells", British Journal of Cancer 90(1): 236-244 (2004).

Pao et al., "Epidermal Growth Factor Receptor Mutations, Small-Molecule Kinase Inhibitors, and Non-Small-Cell Lung Cancer: Current Knowledge and Future Directions", Journal of Clinical Oncology 23(11): 1-13 (2005).

Patani et al., "Bioisosterism: A Rational Approach in Drug Design", Chem. Rev. 96: 3147-3176 (1996).

Polychronis et al., "Preoperative gefitinib versus gefitinib and anastrozole in postmenopausal patents with oestrogen-receptor positive and epiderman-growth-factor-receptor-positive primary breast cancer: a double-blind placebo-controlled phase II randomized trial", 6(6): 383-391 (2005).

Rewcastle et al., "Tyrosine Kinase Inhibitors. 5 . . . 4-(Phenylamino)quinazolines as Potent . . . Inhibitors of the Tyrosine Kinase Domain of the Epidermal Growth Factor Receptor", 1. Med. Chem. 38: 3482-3487 (1995).

Rewcastle et al., "Tyrosine Kinase Inhibitors. 12. Synthesis and Strukcture -Activity Relationships for 6-Substituted 4-(Phenylamino)pyrimido[5,4-d]pyrimidines Designed as Inhibitors of the Epidermal Growth Factor Receptor", J. Med. Chem. 40: 1820-1826 (1997).

Singh et al., "Inhibitors of the epidermal growth factor receptor protein tyrosine kinase: A quantitative structure-activity relationship analysis", J. Enzyme Inhibition 13: 125-134 (1998).

Smaill et al., "Tyrosine kinase inhibitors. 17. Irreversible inhibitors of the epidermal growth factor receptor: 4-(Phenylamino)quinazoline-and 4-(Phe-nylamino)pyrido", J. Med. Chem. 43(16): 3199 (2000).

Speake et al. "Characterization of AZD8931, a Potent Reversible Small Molecule Inhibitor Against Epidermal Growth Factor Receptor (EGFR), Erythroblastic Leukemia Viral Oncogene Homolog 2 (HER2) and 3 (HER3) with a Unique and Balanced Pharmacological Profile". J Clin. Oncol. (2009), vol. 27, 15s, Abstract 11072.

Stamos et al., "Structure of the Epidermal Growth Factor Receptor Kinase Domain Alone and in Complex with a 4-Anilinoquinazoline Inhibitor", J. Bio. Chem. 277(48): 46265-46272 (2002).

Takabatake et al., "Tumor inhibitory effect of gefitinib (ZD1839, Iressa) and taxane combination therapy in EGFR-overexpressing breast cancer cell lines (MCMADR, MDA-MB-23 1)", International Journal of Cancer 120(1): 181-188 (2007).

Thompson et al., "Tyrosine Kinase Inhibitors. 13. Structure-Activity Relationships for Soluble 7-Substituted 4-[(3-Bromophenyl)amino]pyrido[4,4-d]pyrimidines Designed as Inhibitors of the Tyrosine Kinase Activity of the Epidermal Growth Factor Receptor", 1. Med. Chem. 40: 3915-3925 (1997).

Traxler et al., "4-(Phenylamino)pyrrolopyrimidines: Potent and Selective, ATP Site Directed Inhibitors of the EFT-Receptor Protein Tyrosine Kinase", 1. Med. Chem. 39: 2285-2292 (1996).

Traxler "Oncologic, Endocrine & Metabolic: Protein tyrosine kinase inhibitors in cancer treatment", Expert Opinion on Therapeutic Patents 7: 571-588 (1997).

Traxler "Monthly Focus: Oncologic, Endocrine & Metabolic: Tyrosine kinase inhibitors in cancer treatment (Part II)", Expert Opinion on Therapeutic Patents 8: 1599-1625 (1998).

Tsou et al., "6-Substituted-4-(3-bromophenylamino)quinazolines As Putative Irreversible Inhibitors of the Epidermal Growth Factor Receptor (Egfr) and Human Epidermal Growth Factor Receptor (Her-2) Tyrosine Kinases with Enhanced Antitumor Activity", 1. Med. Chem. 44: 2719-2734 (2001).

Vema et al., "Design of EGFR Kinase Inhibitors: A Ligand-Based Approach and Its Confirmation with Structure-Based Studies," Bioorg. Med. Chem. 11: 4643-4653 (2003).

Wright et al., "Allosteric inhibition of fructose-1,6-bisphosphatase by anilinoquinazolines", Bioorg Med. Chem. Lett. 11(1): 17-21 (2001).

Xue et al., "ErbB3-dependent motility and intravasation in breast cancer metastasis", Cancer Research 66(3): 1418-1426 (2006).

* cited by examiner

Differential scanning calorimetry and thermogravimetric analysis of Compound (I) free form

Powder X-ray diffraction pattern of Compound (I) difumarate Form A

Thermogravimetric analysis of Compound (I) difumarate Form A

Powder X-ray diffraction pattern of Compound (I) difumarate Form B

Powder X-ray diffraction pattern of Compound (I) difumarate Form H

Powder X-ray diffraction pattern of Compound (I) difumarate Form J

Powder X-ray diffraction pattern of Compound (I) difumarate Form L

Powder X-ray diffraction pattern of Compound (I) difumarate Form M

Powder X-ray diffraction pattern of Compound (I) difumarate Form N

Powder X-ray diffraction pattern of Compound (I) difumarate Form O

Powder X-ray diffraction pattern of Compound (I) difumarate Form P

Powder X-ray diffraction pattern of Compound (I) difumarate Form Q

CRYSTALLINE 4-(3-CHLORO-2-FLUOROANILINO)-7 METHOXY-6-{[1-(N-METHYLCARBAMOYL METHYL)PIPERIDIN-4-YL]OXY} QUINAZOLINE DIFUMARATE FORM A

CROSS-REFERENCE TO RELATED APPLICATIONS

The present application is a continuation of U.S. application Ser. No. 12/463,624, filed May 11, 2009, now U.S. Pat. No. 8,088,782 which claims benefit under 35 U.S.C. §119(e) of U.S. Provisional Application Ser. No. 61/052,706 filed on May 13, 2008 and U.S. Provisional Application Ser. No. 61/110,637 filed on Nov. 3, 2008, the contents of which are herein incorporated by reference in its entirety.

BACKGROUND

The erbB family of receptor tyrosine kinases, which include EGFR, erbB2, erbB3 and erbB4, are frequently involved in driving the proliferation and survival of tumour cells and as such the erbB family of receptors is implicated in a number of epithelial cancers (reviewed in Olayioye et al., *EMBO J.*, 2000, 19, 3159), including for example breast cancer (Sainsbury et al., *Brit. J. Cancer*, 1988, 58, 458; Guerin et al., *Oncogene Res.*, 1988, 3, 21; Slamon et al., *Science*, 1989, 244, 707; Klijn et al., *Breast Cancer Res. Treat.*, 1994, 29, 73 and reviewed in Salomon et al., *Crit. Rev. Oncol. Hematol.*, 1995, 19, 183), non-small cell lung cancers (NSCLCs) including adenocarcinomas (Cerny et al., *Brit. J. Cancer*, 1986, 54, 265; Reubi et al., *Int. J. Cancer*, 1990, 45, 269; Rusch et al., *Cancer Research*, 1993, 53, 2379; Brabender et al, *Clin. Cancer Res.*, 2001, 7, 1850) as well as other cancers of the lung (Hendler et al., *Cancer Cells*, 1989, 7, 347; Ohsaki et al., *Oncol. Rep.*, 2000, 7, 603), bladder cancer (Neal et al., *Lancet*, 1985, 366; Chow et al., *Clin. Cancer Res.*, 2001, 7, 1957, Zhau et al., *Mol Carcinog.*, 3, 254), oesophageal cancer (Mukaida et al., *Cancer*, 1991, 68, 142), gastrointestinal cancer such as colon, rectal or stomach cancer (Bolen et al., *Oncogene Res.*, 1987, 1, 149; Kapitanovic et al., *Gastroenterology*, 2000, 112, 1103; Ross et al., *Cancer Invest.*, 2001, 19, 554), cancer of the prostate (Visakorpi et al., *Histochem. J.*, 1992, 24, 481; Kumar et al., 2000, 32, 73; Scher et al., *J. Natl. Cancer Inst.*, 2000, 92, 1866), leukaemia (Konaka et al, *Cell*, 1984, 37, 1035, Martin-Subero et al., *Cancer Genet Cytogenet.*, 2001, 127, 174), ovarian (Hellstrom et al., *Cancer Res.*, 2001, 61, 2420), head and neck (Shiga et al., *Head Neck*, 2000, 22, 599) or pancreatic cancer (Ovotny et al., *Neoplasma*, 2001, 48, 188).

Accordingly it has been recognised that an inhibitor of erbB receptor tyrosine kinases should be of value as a selective inhibitor of the growth of certain carcinomas. A number of erbB tyrosine kinase inhibitors have demonstrated clinical benefit and a number of erbB tyrosine kinase inhibitors have been approved for use in the treatment of cancer. For example, the EGFR tyrosine kinase inhibitors gefitinib and erlotinib for the treatment of advanced non-small cell lung cancer and lapatinib, which has erbB2 tyrosine kinase inhibitory activity, for use in metastatic breast cancer. Several other EGFR and erbB2 tyrosine kinase inhibitors are currently in development.

Compound (I) is disclosed in International Patent Application Publication number WO2005/028469 as Example 1 therein and is of the structure:

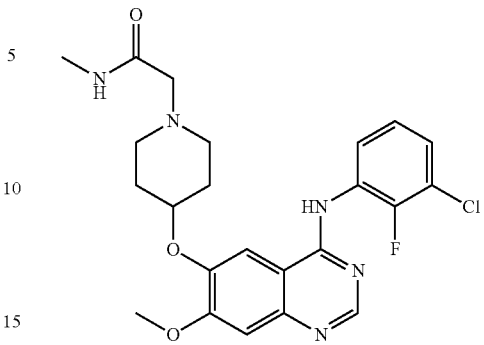

Compound (I)

Compound (I) is an erbB receptor tyrosine kinase inhibitor, in particular Compound (I) is a potent inhibitor of EGFR and erbB2 receptor tyrosine kinases.

There is a growing body of pre- and clinical evidence suggesting that, in addition to signalling via EGFR and erbB2 homodimers, cell signalling mediated by EGFR, erbB2 & erbB3 heterodimers may be an important oncogenic signalling pathway (Sergina et al., Nature, 2007, 445, 437; Ritter et al., Clin Cancer Res. 2007, 13, 4909; Johnston et al., JCO, 2008, 26, 1066). Since erbB3 does not have an intrinsic tyrosine kinase activity, activation of the erbB3 receptor is achieved only through the formation of heterodimeric receptor complexes with other kinase-active receptors including particularly EGFR and erbB2. EGFR and erbB2 heterodimers formed with erbB3 are thought to drive tumour growth in tumours where these receptors are expressed.

We have found in pre-clinical experiments that Compound (I) also inhibits erbB3 mediated signalling through the inhibition of phosphorylation of erbB3 following ligand stimulated EGFR/erbB3 and/or erbB2/erbB3 heterodimerisation. Accordingly, Compound (I) exhibits a unique erbB tyrosine kinase inhibitory effect compared to other erbB tyrosine kinase inhibitors such as gefitinib or erlotinib that act primarily as EGFR tyrosine kinase inhibitors. We have carried out pre-clinical studies which suggest that Compound (I) exhibits improved anti-tumour effects compared to EGFR tyrosine kinase inhibitors such as gefitinib and erlotinib. Without wishing to be bound by theory, it is thought that the improved properties may result from the inhibition of the erbB3 mediated signalling by Compound (I).

WO2005/028469 indicates that the compounds disclosed therein may be prepared in the form of a pharmaceutically acceptable salt, for example, an acid-addition salt of a compound of the Formula I, with an inorganic or organic acid such as hydrochloric, hydrobromic, sulfuric, trifluoroacetic, citric or maleic acid. Nowhere in WO2005/028469 is there a suggestion of a salt with fumaric acid. Compound (I) is disclosed in Example 1 of WO2005/028469 and is isolated as the free base. There is no disclosure in WO2005/028469 of any specific salt of Compound (I).

We have found that Compound (I) is crystalline with some amorphous character as shown in the XRPD of FIG. 1. Differential scanning calorimetry (FIG. 2A) on Compound (I) shows a broad endotherm with an onset of 76.2° C., which is likely to be due to solvent loss, most likely water, followed by a melting endotherm with an onset of 126.2° C. Thermogravimetric analysis on Compound (I) (FIG. 2B) shows a weight loss of 1.2% between 25° C. and 95° C.

Dynamic Vapour Sorption (FIG. 3) shows moisture uptake of approximately 1.9% w/w at 80% relative humidity, accordingly Compound (I) is moderately hygroscopic.

We have found that Compound (I) has a relatively low intrinsic dissolution rate, particularly at pH below 6.0 and has a high cellular permeability. The low solubility and high permeability suggest a BCS classification of Class II for Compound (I). Therefore, the dissolution characteristics of the compound may be critical in controlling drug absorption and inter patient variability, especially at higher doses. These findings together with the facts that Compound (I) is partially amorphous and is hygroscopic has resulted in the need to find alternative forms of Compound (I) with improved properties.

We have surprisingly found that the difumarate salt of Compound (I) has favourable properties compared to Compound (I). Compound (I) difumarate has a favourable dissolution profile exhibiting, high aqueous solubility and a good intrinsic dissolution rate. Furthermore, the Compound (I) difumarate exhibits favourable solid-state properties, for example high crystallinity, low hygroscopicity and/or favourable thermal properties, such as a high melting point.

SUMMARY

The present invention relates to a salt of 4-(3-chloro-2-fluoroanilino)-7-methoxy-6-{[1-(N-methylcarbamoylmethyl)piperidin-4-yl]oxy}quinazoline hereafter "Compound (I)", more particularly to the difumarate salt of Compound (I). The salt is expected to be useful for the treatment or prophylaxis of conditions mediated alone or in part by erbB receptor signalling, particularly proliferative diseases such as cancer. The invention also relates to a pharmaceutical composition comprising the salt and to the use thereof in the manufacture of a medicament for use in the treatment or prophylaxis of cancer, such as breast cancer.

DETAILED DESCRIPTION

Accordingly a first aspect of the present invention provides Compound (I) difumarate.

Suitably the Compound (I) difumarate is crystalline. Therefore according to a further aspect of the present invention there is provided crystalline Compound (I) difumarate.

The Compound (I) difumarate may exist in solvated as well as unsolvated forms such as, for example, hydrated forms. It is to be understood that the invention encompasses all such solvated and unsolvated forms of Compound (I) difumarate.

Figure 4:
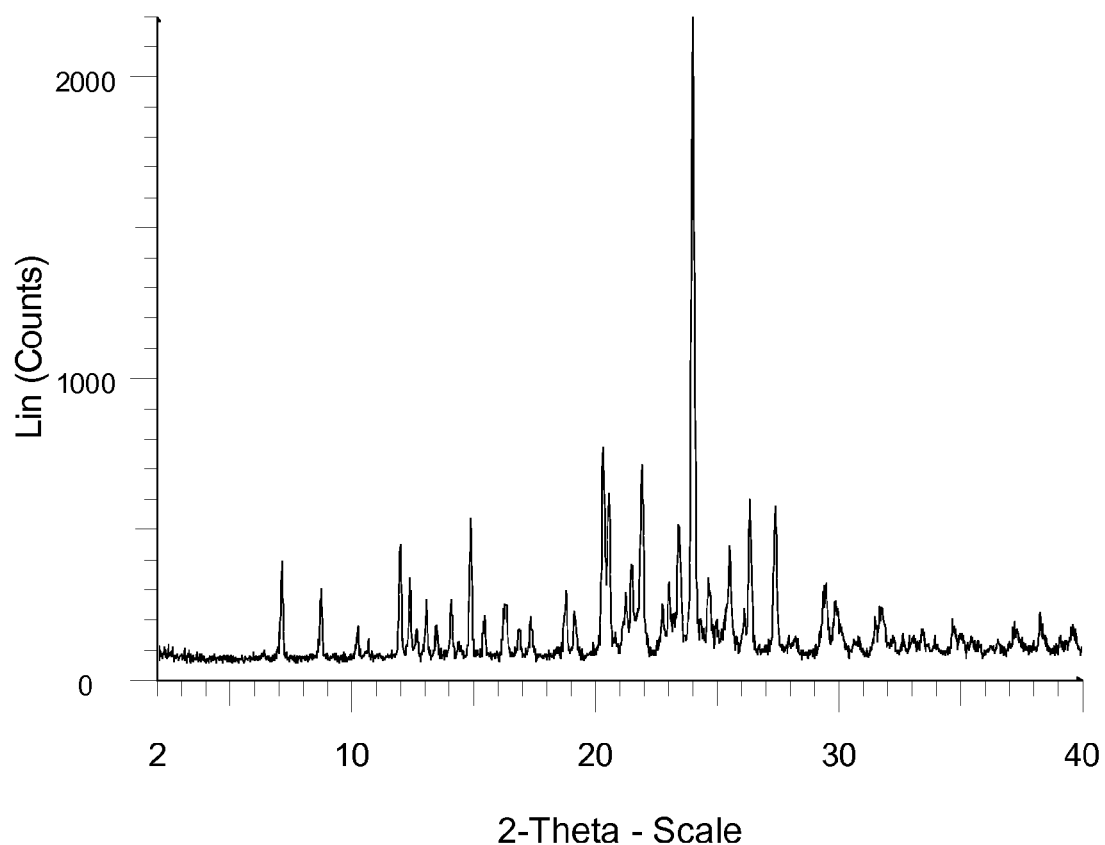
FIG. 4 shows an X-ray powder diffraction pattern (XRPD) for Compound (I) difumarate Form A. The x-axis shows the 2-theta value and the y-axis the counts.

We have found that a particular crystalline form of Compound (I) difumarate, hereafter "Form A" is characterised in that it provides an X-ray powder diffraction pattern substantially as shown in FIG. 4. The most prominent peaks of Form A are shown in Table 1.

TABLE 1

The most prominent X-Ray Powder Diffraction peaks for Form A

| Angle 2-Theta° (2θ) | Intensity Count |
| --- | --- |
| 6.3 | W |
| 7.1 | S |
| 8.7 | S |
| 10.2 | M |
| 10.6 | M |
| 11.9 | S |
| 12.4 | S |
| 12.6 | M |
| 13.0 | S |
| 13.4 | M |
| 14.1 | S |
| 14.4 | M |
| 14.9 | S |
| 15.4 | M |
| 16.3 | M |
| 16.9 | M |
| 17.3 | M |
| 18.8 | S |
| 19.2 | M |
| 20.3 | VS |
| 20.5 | VS |
| 21.2 | S |
| 21.5 | S |
| 21.9 | VS |
| 22.7 | M |
| 23.0 | S |
| 23.5 | S |
| 24.0 | VS |
| 24.7 | S |
| 25.5 | S |
| 26.1 | M |
| 26.4 | VS |
| 27.4 | S |
| 28.2 | M |
| 29.5 | S |
| 29.9 | S |
| 30.8 | M |
| 31.5 | M |
| 31.8 | M |
| 32.2 | M |
| 32.7 | M |
| 33.0 | M |
| 33.5 | M |
| 34.0 | M |
| 34.7 | M |
| 35.1 | M |
| 35.5 | M |
| 35.8 | M |
| 36.6 | M |
| 37.3 | M |
| 38.3 | M |
| 39.2 | M |
| 39.7 | M |

In Table 1 the following abbreviations are used: VS=very strong; S=strong; M=medium and W=weak.

According to a further aspect of the invention there is provided Form A, wherein said Form A has an X-ray powder diffraction pattern with at least one specific peak at about 2-theta=26.4°.

According to a further aspect of the invention there is provided Form A, wherein said Form A Agent has an X-ray powder diffraction pattern with at least one specific peak at about 2-theta=26.4°, 14.9° or 7.1°.

According to a further aspect of the invention there is provided Form A, wherein said Form A has an X-ray powder diffraction pattern with specific peaks at about 2-theta=26.4°, 14.9° and 7.1°.

According to a further aspect of the invention there is provided Form A, wherein said Form A has an X-ray powder diffraction pattern with at least one specific peak at about 2-theta=26.4°, 24.0°, 14.9°, 12.4° or 7.1°.

According to a further aspect of the invention there is provided Form A, wherein said Form A has an X-ray powder diffraction pattern with specific peaks at about 2-theta=26.4°, 24.0°, 14.9°, 12.4° and 7.1°.

According to a further aspect of the invention there is provided Form A, wherein said Form A has an X-ray powder diffraction pattern with at least one specific peak at about 2-theta=26.4°, 24.0°, 23.0°, 21.2°, 17.3°, 15.4°, 14.9°, 13.0, 12.4° or 7.1°.

According to a further aspect of the invention there is provided Form A, wherein said Form A has an X-ray powder diffraction pattern with specific peaks at about 2-theta=26.4°, 24.0°, 23.0°, 21.2°, 17.3°, 15.4°, 14.9°, 13.0°, 12.4° and 7.1°.

According to another aspect of the invention there is provided Form A, wherein said Form A has an X-ray powder diffraction pattern substantially the same as the X-ray powder diffraction pattern shown in FIG. 4.

Suitably Form A is substantially free of other forms of Compound (I) difumarate. For example, at least 80% of the Compound (I) difumarate is in the form of Form A, particularly at least 90%, more particularly, at least 95% and still more particularly at least 99% of the Compound (I) difumarate is in the form of Form A. In a particular embodiment at least 98% of the Compound (I) difumarate is in the form of Form A. Reference herein to, for example, 80% of the Compound (I) difumarate being in the form of Form A, refer to the % by weight of the Compound (I) difumarate.

Figure 5:
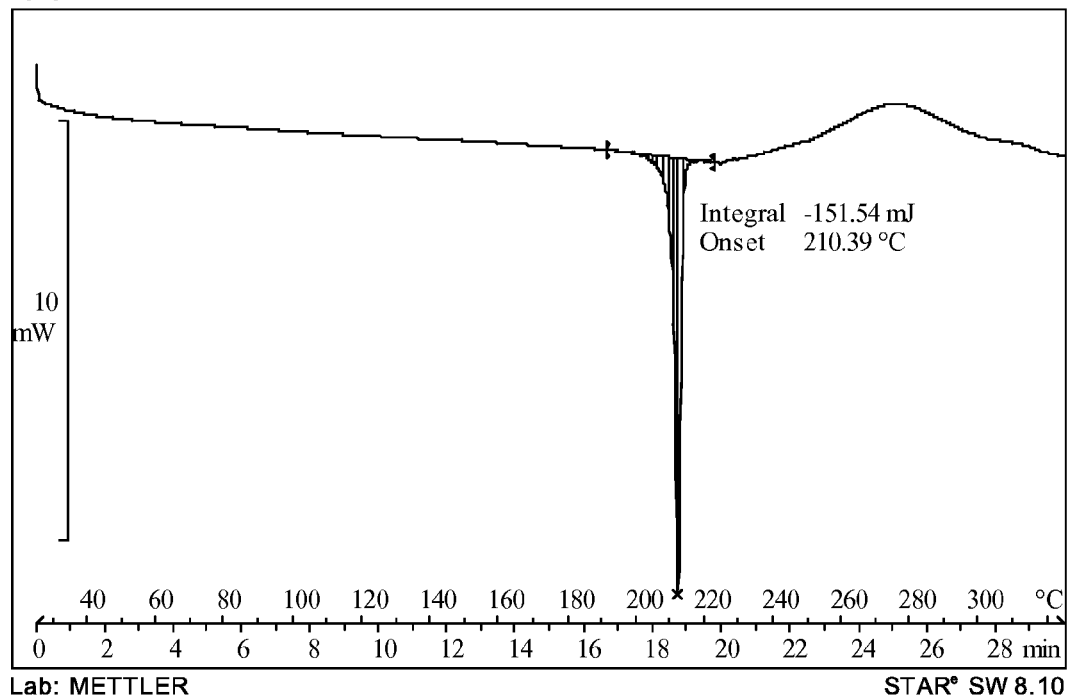
FIG. 5 shows a differential scanning calorimetry trace on Compound (I) difumarate Form A. The x-axis shows the temperature and time, the y-axis shows power in mW. The text on the figure shows the onset temperature of the melting endotherm and the integral (mJ) of the curve.

The DSC thermogram for Form A is shown in FIG. 5 hereinafter. Form A, shows a sharp melting endotherm with an onset temperature of about 210.4° C., as determined by differential scanning calorimetry (DSC) analysis using a Mettler DSC820e apparatus as described in the Examples. Accordingly Form A has a melting point of about 210° C.

We have found that Compound (I) difumarate may exist in other crystalline forms, for example the Forms B to Q described in the Examples herein. According to a further aspect of the invention there is provided crystalline Compound (I) difumarate selected from any one of Form B to Form Q described herein. Suitably each of the crystalline Compound (I) difumarate forms described is substantially free of other forms of Compound (I) difumarate. For example, at least 80% of the Compound (I) difumarate is in the desired form, particularly at least 90%, more particularly, at least 95% and still more particularly at least 99% of the Compound (I) difumarate is in the desired crystalline form of the difumarate.

The crystalline forms of Compound (I) difumarate described herein are crystalline. Suitably the degree of crystallinity as determined by X-ray powder diffraction data is for example greater than about 60%, such as greater than about 80%, particularly greater than about 90% and more particularly greater than about 95%. In embodiments of the invention, the degree of crystallinity as determined by X-ray powder diffraction data is greater than about 98%, wherein the % crystallinity refers to the % by weight of the total sample mass which is crystalline.

In the preceding paragraphs defining the X-ray powder diffraction peaks for the crystalline forms of Compound (I), the term "at about" is used in the expression " . . . at about 2-theta= . . ." to indicate that the precise position of peaks (i.e. the recited 2-theta angle values) should not be construed as being absolute values because, as will be appreciated by those skilled in the art, the precise position of the peaks may vary slightly between one measurement apparatus and another, from one sample to another, or as a result of slight variations in measurement conditions utilised. It is also stated in the preceding paragraphs that the Compound (I) difumarate Form A provides X-ray powder diffraction patterns 'substantially' the same as the X-ray powder diffraction patterns shown in FIG. 4, and has substantially the most prominent peaks (2-theta angle values) shown in Table 1. It is to be understood that the use of the term 'substantially' in this context is also intended to indicate that the 2-theta angle values of the X-ray powder diffraction patterns may vary slightly from one apparatus to another, from one sample to another, or as a result of slight variations in measurement conditions utilised, so the peak positions shown in the Figures or quoted in the Tables are again not to be construed as absolute values.

In this regard, it is known in the art that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions and sample preparation. For example, persons skilled in the art of X-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute (for further information see Jenkins, R & Snyder, R. L. 'Introduction to X-Ray Powder Diffractometry' John Wiley & Sons, 1996). Therefore, it shall be understood that the crystalline forms of Compound (I) difumarate described herein are not limited to the crystals that provide X-ray powder diffraction patterns identical to the X-ray powder diffraction pattern shown in FIG. 4, and any crystals providing X-ray powder diffraction patterns substantially the same as those shown in FIG. 4 fall within the scope of the present invention. A person skilled in the art of X-ray powder diffraction is able to judge the substantial identity of X-ray powder diffraction patterns.

Figure 1:
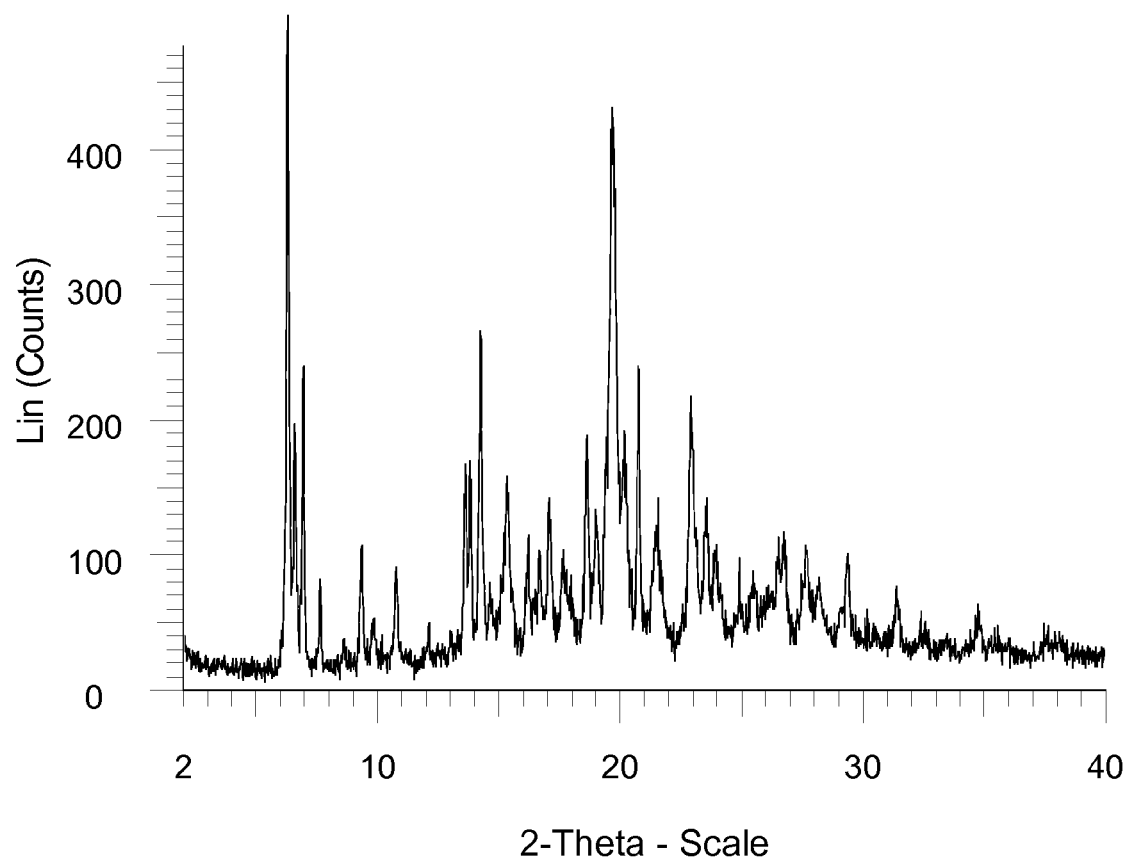
FIG. 1 shows an X-ray powder diffraction pattern (XRPD) for Compound (I) free form. The x-axis shows the 2-theta value and the y-axis the counts.
Figure 2A:
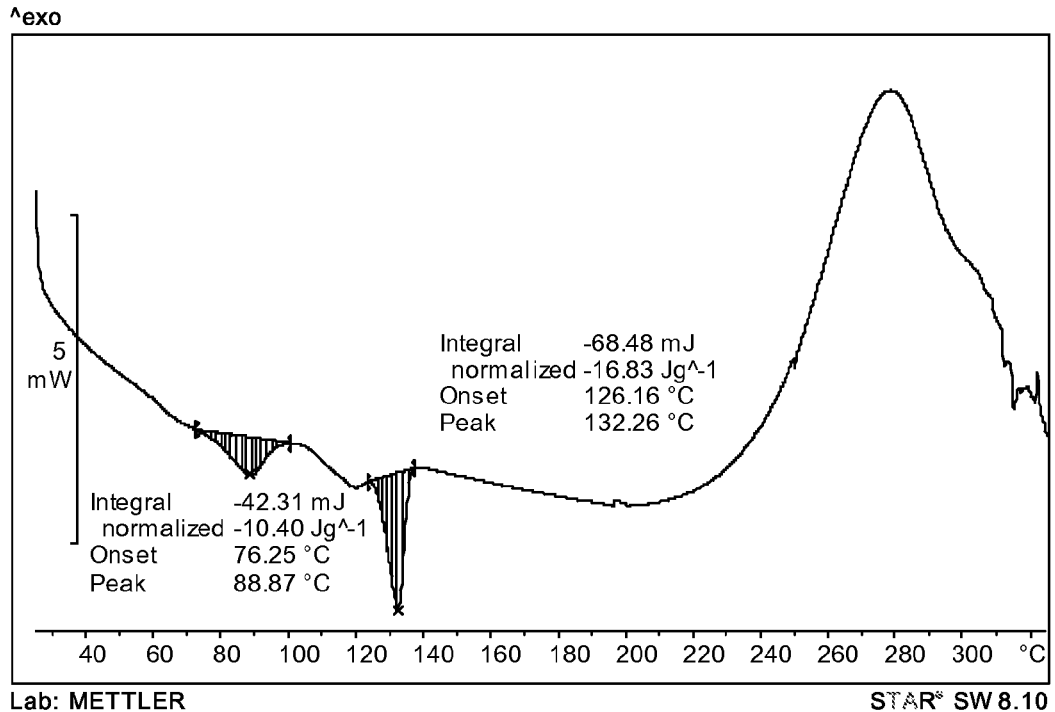
FIG. 2A shows a differential scanning calorimetry trace on Compound (I) free form. The x-axis shows the temperature and time, the y-axis shows power in mW. The text on the figure shows the onset temperature of the endotherms and the integral (mJ) of the curves.
Figure 2B:
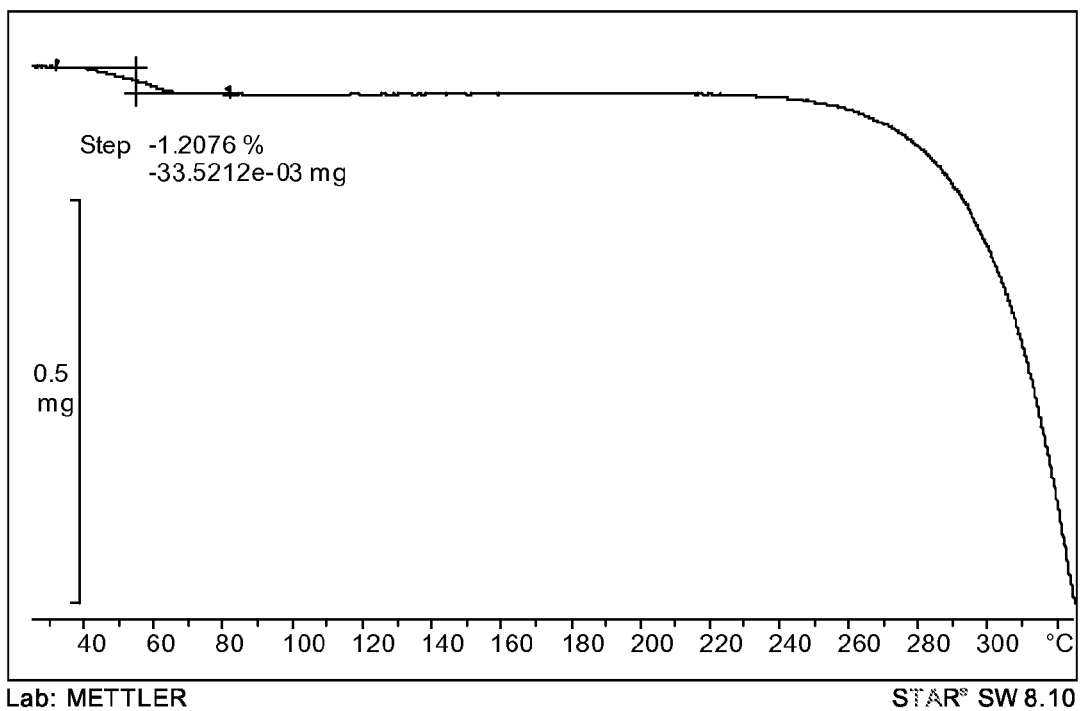
FIG. 2B is a thermogravimetric trace for Compound (I) free form. The x-axis shows temperature and time, the y-axis shows weight in mg. The text in this graph shows the % weight loss and absolute weight loss from the sample for the event between about 30 and 80° C.
Figure 3:
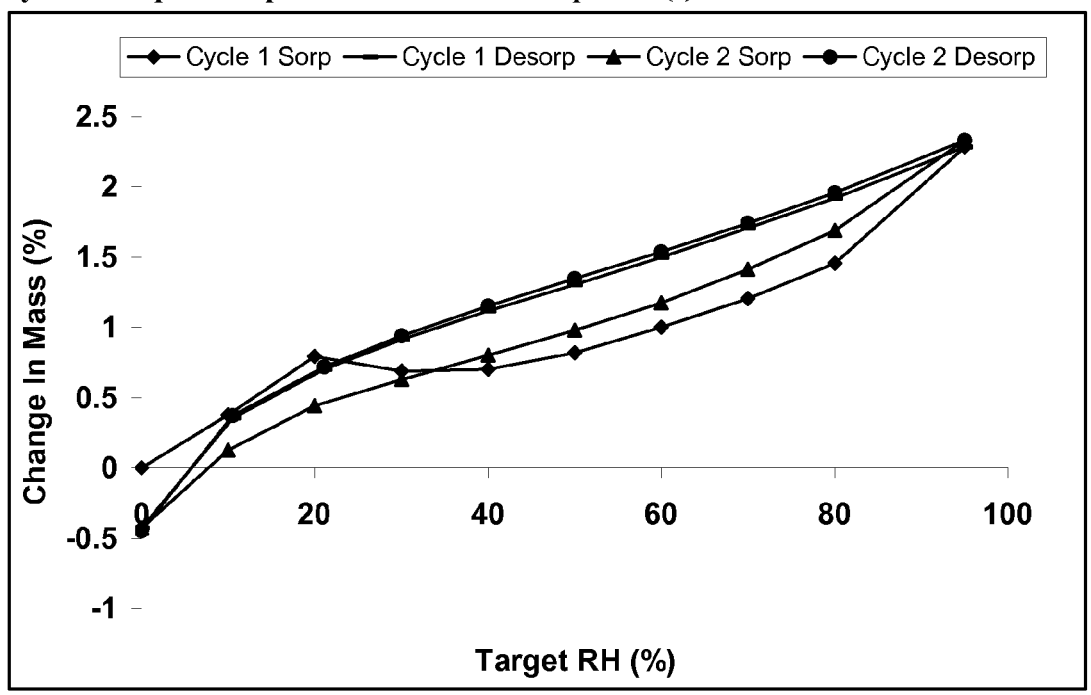
FIG. 3 shows a dynamic vapour sorption isotherm plot for Compound (I) free form. The x-axis shows the % relative humidity, the y-axis shows the % change in mass of the sample. "sorp" refers to an adsorption cycle and "desorp" to a desorption cycle.

Generally, a measurement error of a diffraction angle in an X-ray powder diffractogram is about 2-theta=0.5° or less, and such degree of a measurement error should be taken into account when considering the X-ray powder diffraction patterns in FIGS. 1 and 4, and when interpreting the peak positions referred to in the text above and in Table 1.

The melting points and DSC data described herein were determined using a Mettler DSC820e apparatus, the use of which is described in more detail hereinafter. A person skilled in the art will appreciate that slight variations in the melting point measured by DSC may occur as a result of variations in sample purity, sample preparation and the measurement conditions (e.g. heating rate). It will be appreciated that alternative readings of melting point may be given by other types of equipment or by using conditions different those described hereinafter. Hence the melting point and endotherm figures quoted herein are not to be taken as absolute values and such measurement errors are to be taken into account when interpreting DSC data. Typically, melting points may vary by ±0.5° C. or less.

The crystalline forms of Compound (I) difumarate, such as Form A according to the invention may also be characterised and/or distinguished from other physical forms using other suitable analytical techniques, for example NIR spectroscopy or solid state nuclear magnetic resonance spectroscopy.

The chemical structure of Compound (I) difumarate of the present invention can be confirmed by routine methods for example proton nuclear magnetic resonance (NMR) analysis.
Synthesis of Compound (I)

Compound (I) may be synthesised using the methods described in WO2005/028469 or as illustrated in the Examples herein.

WO2005/028469 discloses as Example 1 therein the preparation of Compound (I) as follows:

2-Chloro-N-methylacetamide (32 mg, 0.3 mmol) was added to a mixture of 4-(3-chloro-2-fluoroanilino)-7-methoxy-6-[(piperidin-4-yl)oxy]quinazoline (120 mg, 0.3 mmol), potassium iodide (16 mg, 0.1 mmol), and potassium carbonate (50 mg, 0.36 mmol) in acetonitrile (5 ml). The mixture was heated at reflux for one hour. After evaporation of the solvents under vacuum, the residue was taken up in dichloromethane. The organic solution was washed with water and brine, dried over magnesium sulfate. After evaporation of the solvents under vacuum, the residue was purified by chromatography on silica gel (eluant: 1% to 2% 7N methanolic ammonia in dichloromethane) to give Compound (I).

We have found that reaction of 2-chloro-N-methylacetamide directly with 4-(3-chloro-2-fluoroanilino)-7-methoxy-6-[(piperidin-4-yl)oxy]quinazoline avoids the use of potassium iodide. Furthermore, crystallisation of Compound (I) from certain solvents provides Compound (I) in high purity. The new process is therefore expected to be suitable for large-scale manufacture of Compound (I).

Accordingly as a further aspect of the present invention there is provided a method for preparing Compound (I) comprising:

(i) reacting 2-chloro-N-methylacetamide with 4-(3-chloro-2-fluoroanilino)-7-methoxy-6-[(piperidin-4-yl)oxy]quinazoline dihydrochloride in the presence of a suitable base;

(ii) adding a solvent selected from ethanol, water and methanol, or a mixture thereof to the reaction mixture from step (i) to effect crystallisation of Compound (I); and (iii) isolating the Compound (I).

The reaction in Step (i) is conveniently carried out is a suitable inert solvent such as those described in Process (c) on page 30 of WO2005/028469. For example, the reaction may be carried out using acetonitrile as the solvent. The reaction is carried out in the presence of a suitable base, for example one of the bases described in Process (c) on page 30 of WO2005/028469, such as triethylamine. Suitably the reaction is carried out at an elevated temperature, for example at about 75° C.

In one embodiment in Step (ii) of the process the solvent is water. Suitably in this embodiment when Step (i) is carried out in acetonitrile the volume ratio of water:acetonitrile is approximately 1:3.

In another embodiment of the invention in Step (ii) of the process the solvent is ethanol. Suitably in this embodiment when Step (i) is carried out in acetonitrile the volume ratio of ethanol:acetonitrile is approximately 3.5:7.

In a further embodiment of the invention in Step (ii) of the process the solvent is a mixture of ethanol and water. Suitably in this embodiment the volume ratio of ethanol to water is about 20:1 to about 30:1, for example about 21.9:1 to 25:1.

When Step (i) is carried out in acetonitrile suitably approximately 3.5 volumes of ethanol and 0.15 volumes of water are added to 7 volumes of acetonitrile to effect crystallisation.

As will be understood reference to a volume ratio of for example of water:acetonitrile being 1:3 means that 1 volume of water is added to 3 volumes of the acetonitrile present in the reaction vessel following the completion of Step (i) of the process.

In one embodiment, in Step (ii) of the process the reaction mixture from Step (i) is cooled to about 70° C. and ethanol is added. The reaction mixture is then cooled to about 45° C. and the water is added to effect crystallisation of the Compound (I). If required the reaction mixture may be seeded with Compound (I) to help initiate the crystallisation. The reaction mixture is then cooled to about 20° C. to complete the crystallisation.

The isolation of the Compound (I) in Step (iii) may be carried out using conventional methods, for example filtration and drying of the Compound (I).

The 4-(3-chloro-2-fluoroanilino)-7-methoxy-6-[(piperidin-4-yl)oxy]quinazoline dihydrochloride used as the starting material may be prepared as described in the Examples herein. For example, by adding hydrochloric acid to 6-{[(1-tert-butoxycarbonyl)piperidin-4-yl]oxy}-4-(3-chloro-2-fluoroanilino)-7-methoxyquinazoline. Conveniently the reaction is carried out in a suitable solvent, for example ethanol, acetonitrile, tetrahydrofuran, 2-methyltetrahydrofuran, n-propanol, methanol, 1-butanol, ethyl acetate, tert-butyl acetate, isopropanol or industrial methylated spirit. A particular solvent is ethanol or more particularly industrial methylated spirit.

The 6-{[(1-tert-butoxycarbonyl)piperidin-4-yl]oxy}-4-(3-chloro-2-fluoroanilino)-7-methoxyquinazoline may be prepared using the method described in Example 1 of WO2005/028469 by reacting 4-(3-Chloro-2-fluoroanilino)-6-hydroxy-7-methoxyquinazoline with tert-Butyl (4-methanesulfonyloxy)piperidine-1-carboxylate, wherein the reaction is carried out in the presence of cesium fluoride using DMA as a solvent and at a temperature of 85° C.

This reaction may also be carried out in the presence of N-methylpyrrolidone (NMP) in the presence of a suitable base such as potassium carbonate. This reaction is suitably performed at an elevated temperature as described in the Examples herein.

However, we have found that by carrying the reaction out in the presence of certain solvents provides the product in good form. Furthermore some of these solvents are expected to be suitable for large-scale manufacture of the product.

Accordingly, as a further aspect of the present invention there is provided a process for the preparation of 6-{[(1-tert-butoxycarbonyl)piperidin-4-yl]oxy}-4-(3-chloro-2-fluoroanilino)-7-methoxyquinazoline comprising:

(i) reacting 4-(3-chloro-2-fluoroanilino)-6-hydroxy-7-methoxyquinazoline with tert-butyl (4-methanesulfonyloxy)piperidine-1-carboxylate in the presence of a suitable base, wherein the reaction is carried out in a solvent selected from N-methylpyrrolidone or an alcohol selected from methanol, ethanol, isopropyl alcohol, n-propanol and industrial methylated spirit; and (ii) crystallising the 6-{[(1-tert-butoxycarbonyl)piperidin-4-yl]oxy}-4-(3-chloro-2-fluoroanilino)-7-methoxyquinazoline.

Step (i) of this process is carried out in the presence of a suitable base, for example those described in WO2005/028469, such as potassium carbonate. The reaction is suitably carried out at elevated temperature conveniently at the reflux temperature.

If required water can be added to the solvents used in Step (i) to aid processing, for example to increase the mobility of the reaction mixture. In one embodiment Step (i) of the reaction is carried out in an alcohol selected from methanol, ethanol, isopropyl alcohol, n-propanol and industrial methylated spirit, optionally in the presence of water. In a further embodiment the reaction Step (i) is carried out in a mixture of ethanol and water. When a mixture of ethanol and water is used, the volume ratio of ethanol to water in Step (i) is not critical, for example a volume ratio of ethanol to water may be up to about 10:2 is suitable, such as about 10:1.

The crystallisation in Step (ii) of the process is conveniently carried out by cooling the reaction mixture from Step (i) (for example cooling to about 70° C.) and adding water to the mixture to effect crystallisation. The product may then be isolated by conventional methods such as those described in the Examples.

Compound (I) may also be prepared according to the process illustrated in Reaction Scheme 1:

Reaction Scheme 1

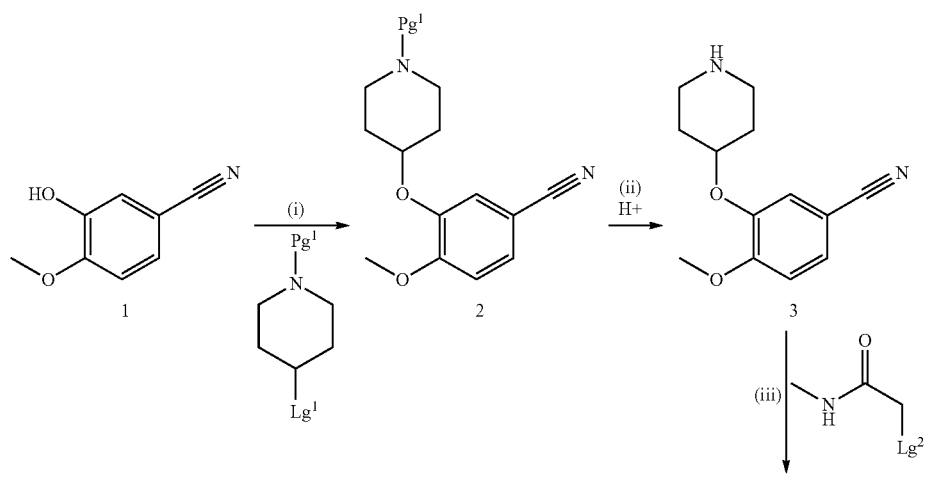

-continued

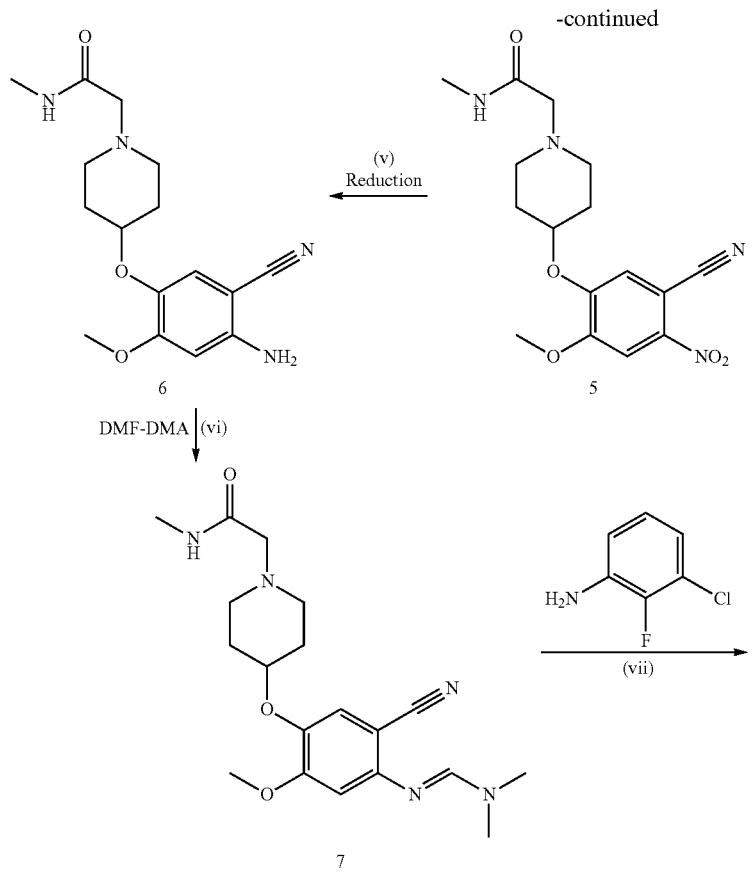
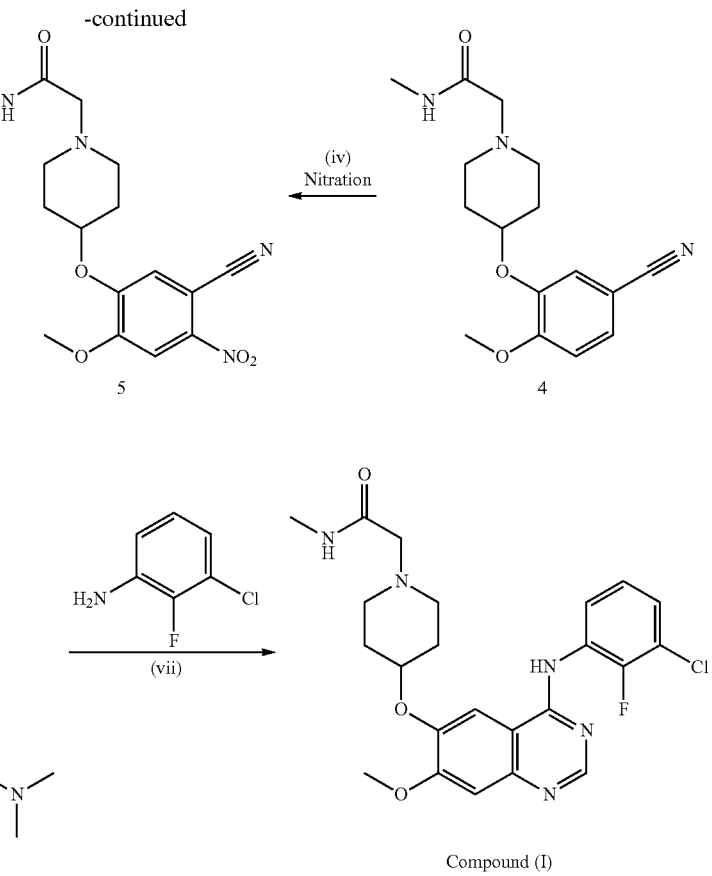

Notes on Reaction Scheme 1:

Step (i): $Lg^1$ is a suitable leaving group, for example, a halogeno, alkanesulfonyloxy or arylsulfonyloxy group, for example a chloro, bromo, methanesulfonyloxy, 4-nitrobenzenesulfonyloxy or toluene-4-sulfonyloxy group (suitably a methanesulfonyloxy, 4-nitrobenzenesulfonyloxy or toluene-4-sulfonyloxy group, for example $Lg^1$ is methanesulfonyloxy).

$Pg^1$ is a suitable amine protecting group. Such groups are well known, for example as described in one of the many general texts on the subject, such as, 'Protective Groups in Organic Synthesis' by Theodora Green (publisher: John Wiley & Sons). Examples of amino protecting groups include an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. A particular example of $Pg^1$ is tert-butoxycarbonyl.

The reaction is suitably carried out in the presence of a base, for example a carbonate such as potassium carbonate. The reaction is conveniently carried out in the presence of a suitable inert solvent, for example an alcohol such as isopropanol. The reaction is suitably carried out at elevated temperature, conveniently at the reflux temperature of the solvent.

Step (ii): The protecting group $Pg^1$ is removed using conventional methods. For example when $Pg^1$ is tert-butoxycarbonyl it may be removed by treatment with a suitable acid as hydrochloric, sulfuric or phosphoric acid or trifluoroacetic acid.

Step (iii): $Lg^2$ is a suitable leaving group, for example, a halogeno, such as chloro. The reaction is suitably carried out in the presence of a suitable base such as a carbonate, an organic amine or an alkoxide. Suitable bases include potassium carbonate or triethanolamine. The reaction is conveniently carried out in the presence of an inert solvent such as acetonitrile or an alcohol such as ethanol. The reaction is suitably performed at an elevated temperature, conveniently the reflux temperature of the solvent.

Step (iv): Nitration may be effected using well known methods for the nitration of aromatic rings, for example by treating the 2-[4-(5-Cyano-2-methoxyphenoxy)piperidin-1-yl]-N-methylacetamide (4) with nitric acid in the presence of sulfuric acid using well known conditions for such reactions and as illustrated in the Examples.

Step (v): Reduction reactions suitable for reducing nitro groups to amines are well known, for example by reduction in the presence of a suitable reducing agent such as sodium dithionite. This reaction is suitably carried out in the presence of an aqueous solvent, for example aqueous methanol. The reaction is conveniently performed at elevated temperature for example 40 to 60° C. Alternatively, reduction may be effected by hydrogenation, for example by catalytic hydrogenation with using a suitable catalyst such as a palladium on carbon catalyst, for example a 10% palladium on carbon catalyst. The hydrogenation is conveniently carried out in a suitable solvent such as methanol.

Step (vi): 2-[4-(4-Amino-5-cyano-2-methoxyphenoxy)piperidin-1-yl]-N-methylacetamide (6) is reacted with N,N-dimethylformamide dimethyl acetal. The reaction is conveniently carried out in the presence of a suitable solvent such as an ether, for example, 2-methyltetrahydrofuran or an aromatic hydrocarbon such as toluene. The reaction is suitably performed at an elevated temperature, for example at about 70 to 105° C., suitably about 76° C.

Step (vii) The reaction is suitably carried out in the presence of a suitable acid, such as one or more acids selected from acetic, propanoic, succinic, fumaric and citric acid. In one example the acid is acetic acid. The reaction is suitably carried out in the presence of an inert solvent, for example an aromatic hydrocarbon solvent such as methoxybenzene. The reaction is suitably carried out at elevated temperature, for example from about 90 to about 120° C., suitably at about 90° C.

The process described in Reaction Scheme 1 forms a further aspect of the present invention. Accordingly, there is provided a method for preparing Compound (I) comprising reacting 2-[4-(5-cyano-4-{[(dimethylamino)methylene]amino}-2-methoxyphenoxy)piperidin-1-yl]-N-methylacetamide (7) with 3-chloro-2-fluoroaniline in the presence of a suitable acid.

Suitable reaction conditions are as hereinbefore described in relation to Step (vii) of Reaction Scheme 1.

Certain intermediates shown in Reaction Scheme 1 are novel and form a further aspect of the present invention. Accordingly another aspect of the invention provides a compound selected from any one of compounds 2, 3, 4, 5, 6 and 7 in Reaction Scheme 1, or a salt thereof; wherein $Pg^1$ is as hereinbefore defined (for example tert-butoxycarbonyl). Some of the intermediates such as compound (7) in Reaction Scheme 1 may have geometric isomeric centres (E- and Z-isomers). It is to be understood that the present invention encompasses all such geometric isomers and mixtures thereof.

Synthesis of Compound (I) Difumarate Form A

According to a further aspect of the present invention there is provided a process for the preparation of Compound (I) difumarate (Form A) comprising:

(i) reacting Compound (I) with a sufficient quantity of fumaric acid to form the difumarate salt;

(ii) crystallising the Form A; and (iii) isolating the Form A.

Notes on Step (i)

Conveniently the reaction with the fumaric acid is carried out in a suitable solvent, for example, selected from methanol, ethanol, 1-butanol, 2-butanol and diacetone alcohol. The reaction may also be carried out in a mixture of suitable solvents, for example a mixture selected from methyl ethyl ketone and dimethylformamide; methyl ethyl ketone and tetrahydrofuran; methyl ethyl ketone and methanol; methyl ethyl ketone and isopropanol; ethanol and dimethyl sulfoxide; ethanol and tetrahydrofuran; ethanol and isopropanol; 1-butanol and dimethylformamide; 1-butanol and dimethyl sulfoxide; 1-butanol and tetrahydrofuran; 1-butanol and methanol; 1-butanol and isopropanol; ethylacetate and dimethylformamide; ethyl acetate and methanol; ethyl acetate and isopropanol; and methanol and isopropanol.

In one embodiment the reaction in Step (i) is carried out in water.

In one embodiment the reaction in Step (i) is carried out in a mixture of solvents comprising methyl ethyl ketone and a solvent selected from dimethylformamide, tetrahydrofuran, methanol and isopropanol.

In another embodiment the reaction in Step (i) is carried out in a mixture of solvents comprising ethanol and a solvent selected from dimethyl sulfoxide, tetrahydrofuran and isopropanol.

In another embodiment the reaction in Step (i) is carried out in a mixture of solvents comprising 1-butanol and a solvent selected from dimethylformamide, dimethyl sulfoxide, tetrahydrofuran, methanol and isopropanol.

In another embodiment the reaction in Step (i) is carried out in a mixture of solvents comprising ethyl acetate and a solvent selected from dimethyl formamide, methanol and isopropanol.

In another embodiment the reaction in Step (i) is carried out in a mixture of solvents comprising ethyl acetate and isopropanol.

In another embodiment the reaction in Step (i) is carried out in a mixture of solvents comprising methanol and isopropanol.

In those embodiments where Step (i) of the reaction is carried out in a mixture of solvents comprising methanol and isopropanol, the volume ratio of isopropanol to methanol is suitably in the range of about 3.4:1 to about 1.0:1, for example about 1.5:1 to about 1.0:1. This reaction is suitably carried out at an elevated temperature, for example at a temperature in excess of 60° C., suitably from 65° C. to the reflux temperature of the solvent. Conveniently the Compound (I) is dissolved or dispersed in the isopropanol and this mixture is reacted with a solution or dispersion of the fumaric acid in the methanol.

In those embodiments where Step (i) of the reaction is carried out in a mixture of solvents comprising ethyl acetate and isopropanol, the volume ratio of ethyl acetate to isopropanol is suitably in the range of about 5.1:1 to 1.9:1, for example about 3.9:1 to 1.9:1 such as about 2.1:1. This reaction is suitably carried out at a temperature of about 20 to about 73° C., for example at about 40° C. Conveniently the Compound (I) is dissolved or dispersed in the ethyl acetate and this mixture is reacted with a solution or dispersion of the fumaric acid in the isopropanol. Alternatively, Compound (I) may be pre-dissolved in a mixture of ethyl acetate and isopropanol. If required, the isopropanol may by removed following dissolution of the Compound (I) using conventional methods such as distillation.

When preparing the solution or dispersion of fumaric acid in an alcohol such as methanol or isopropyl alcohol, it may be necessary to heat the mixture to effect dissolution of the fumaric acid. However, excessive heating and/or holding the mixture at elevated temperature for prolonged periods of time should be avoided to minimise ester formation.

Generally in Step (i) of the process Compound (I) is reacted with at least 2 molar equivalents of fumaric acid, for example from about 2 to about 3, particularly about 2 to about 2.7 molar equivalents of fumaric acid. However, lower quantities of fumaric acid can be used in certain solvent systems. For example, when the reaction is carried out in a mixture of ethyl acetate and isopropanol we have found that Compound (I) difumarate can be prepared when the molar ratio of fumaric acid to Compound (I) is greater than or equal to 1.725.

Notes on Step (ii)

Crystallisation of the Form A may be effected using known methods for crystallisation of a compound from solution. For example by causing supersaturation of the solution containing the salt. Supersaturation may be achieved by, for example, cooling the solution, evaporating solvent from the solution or by addition of a suitable anti-solvent to the solution.

In one embodiment crystallisation is effected by cooling the solution. For example, when Step (i) of the reaction is carried out in a mixture of methanol and isopropyl alcohol, the reaction mixture is cooled to about 30° C. over a period of about 90 minutes and is held at 30° C. for about 30 minutes. The reaction mixture may then be further cooled over a period of about 2 hours to a temperature of about 0° C. and is held at the temperature for a sufficient time to allow completion of crystallisation, for example about 1 hour.

Alternatively, when Step (i) of the reaction is carried out in a mixture of ethyl acetate and isopropyl alcohol, the reaction mixture is cooled to about 20° C. (for example from about 40° C. to about 20° C. over a period of about 1 hour). The reaction mixture is then held at 20° C. for a sufficient time to effect crystallisation. Suitably, the reaction mixture is held at about 20° C. for at least 10 hours, for example for about 13.5 hours.

In another embodiment when Step (i) of the reaction is carried out in a mixture of methanol and isopropyl alcohol, crystallisation may be effected by removing a proportion of the solvent to cause supersaturation of the remaining reaction mixture. The solvent may be removed by evaporation or distillation. Suitably about 55 to 65% by weight of the solvent is removed, for example about 62%. If required further isopropanol may be added to the mixture followed by distillation of approximately the same weight of solvent. For example approximately 50 to 60% of additional isopropanol may be added to the mixture, wherein the % is the % by weight of the solvent remaining in the reaction vessel following the first distillation. Following addition of the isopropanol a similar weight of solvent is removed by distillation. Crystallisation may be completed by adding further isopropanol and cooling the mixture to about 0° C. over a period of about 8 hours.

Generally the Form A will self crystallise in Step (ii) of the process, but as will be appreciated by a person skilled in the art, seeding with Form A may be used in order to promote crystallisation. If required, seed crystals could be prepared using the method described above and illustrated in the Examples for the preparation of Compound (I) difumarate Form A.

Notes on Step (iii)

Any suitable method known in the art for isolating crystalline materials from a solution may be used in Step (iii) of the process. Suitably, the Form A is collected by filtration. Following isolation of the Form A, the salt may be washed with a suitable solvent, for example cold isopropanol. Following isolation the Form A may be dried using conventional methods, for example vacuum drying.

Accordingly in one embodiment of the invention there is provided a process for the preparation of Compound (I) difumarate (Form A) comprising:

(i) reacting a solution or suspension of Compound (I) in isopropanol with at least 2 molar equivalents fumaric acid in methanol,
  wherein the volume ratio of isopropanol to methanol is from 3.4:1 to about 1.0:1, for example about 1.5:1 to about 1.0:1,
  and wherein the reaction is carried out at a temperature of at least 60° C.;
(ii) crystallising the Form A; and
(iii) isolating the Form A.

Suitable conditions for crystallisation and isolation of the Form A are as hereinbefore defined.

Accordingly in another embodiment of the invention there is provided a process for the preparation of Compound (I) difumarate (Form A) comprising:

(i) reacting a solution or suspension of Compound (I) in ethyl acetate with at least a 1.725 molar equivalents fumaric acid in isopropanol (suitably at least 2 molar equivalents of fumaric acid),
  wherein the volume ratio of ethyl acetate to isopropanol is suitably from about 5:1 to 1:1, for example about 5.1:1 to 1.9:1 such as about 2.1:1 and wherein the reaction is carried out at a temperature of about 20 to about 73° C. (for example about 40° C.);

(ii) cooling the reaction mixture from Step (i) to about 20° C. and holding the mixture at this temperature to effect crystallisation of the Form A; and
(iii) isolating the Compound (I) difumarate Form A.

Suitable conditions for isolation of the Form A are as hereinbefore defined.

In another embodiment of the invention there is provided a process for the preparation of Compound (I) difumarate (Form A) comprising:

(i) reacting Compound (I) in water with at least 2 molar equivalents of fumaric acid (for example at least 2.05, such as about 2.1 molar equivalents of fumaric acid), and wherein the reaction is carried out at about 85° C.;
(ii) cooling the reaction mixture from Step (i) to about 60° C.; and
(iii) isolating the Compound (I) difumarate Form A.

Suitably in Step (ii) the reaction mixture is cooled slowly to about 60° C., for example at a cooling rate of about 1° C./minute. If required crystallisation of the Form A can be induced by adding seed crystals of the Form A during cooling of the mixture. Suitably the Form A seed crystals are added when the reaction mixture has been cooled to about 77° C. Suitable conditions for isolation of the Form A in Step (iii) are as hereinbefore described.

Crystalline Compound (I) difumarate Forms B to P may be prepared by, for example, the methods described herein in the Examples.

Pharmaceutical Compositions

According to a further aspect of the invention there is provided a pharmaceutical composition which comprises Compound (I) difumarate in association with a pharmaceutically-acceptable diluent or carrier. The Compound (I) difumarate may be used in the composition in any of the forms described herein, for example Form A.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

For example Compound (I) difumarate is suitably formulated as a tablet using the following excipients:

Tablet Core:
  Compound (I) difumarate (for example Form A);
  lactose;
  microcrystalline cellulose;
  crospovidone;
  polyvidone (PVP); and
  magnesium stearate The tablet core may be coated with a film-coating, such as an HPMC based film coating, which coating optionally contains one or more colorants and/or light protective agents.

The tablets may be prepared using conventional methods and as illustrated in the Examples. If required the Compound (I) difumarate may be milled prior to formulation into the tablet to provide a uniform particle size distribution of the Compound (I) difumarate in the tablet. For example the Compound (I) difumarate may be milled to provide an average particle size of about 5 μm. Suitable milling methods are well known.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 200 mg, for example from 1 to 30 mg) compounded with an appropriate and convenient amount of excipients which may vary from about 5 to about 98 percent by weight of the total composition.

The size of the dose for therapeutic or prophylactic purposes of Compound (I) difumarate will naturally vary according to the nature and severity of the conditions, the age and sex of the animal or patient and the route of administration, according to well known principles of medicine.

In using Compound (I) difumarate for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. For instance, Compound (I) difumarate could be administered to a warm-blooded animal orally, at a unit dose less than 1 g daily but more than 1 mg. Particularly Compound (I) difumarate could be administered to a warm-blooded animal, at a unit dose of less than 250 mg per day. In another aspect of the invention, Compound (I) difumarate could be administered to a warm-blooded animal, at a unit dose of less than 160 mg per day. In a further aspect of the invention, Compound (I) difumarate could be administered to a warm-blooded animal, at a unit dose of less than 50 mg per day. The dose of Compound (I) difumarate may be administered as a single daily dose or as multiple fractions of the total daily dose. For example, the total daily dose of Compound (I) difumarate may be administered as two doses, which may be the same or different. Suitably however, each fraction of the total daily dose would be approximately equal. By way of example Compound (I) difumarate may be administered as a one or more oral dosage forms such as a tablet or capsule containing 1.5, 3.7, 14.9, 59.6 or 149 mg of Compound (I) difumarate (equivalent to 1, 2.5, 10, 40 or 100 mg of Compound (I) free form). In a further embodiment a dose of Compound (I) difumarate equivalent to 40, 80, 100, 160, 200 or 240 mg of Compound (I) is administered twice a day. In a particular embodiment a dose of Compound (I) difumarate equivalent to 160 mg of Compound (I) is administered twice a day. In a particular embodiment a dose of Compound (I) difumarate equivalent to 200 mg of Compound (I) is administered twice a day. In another particular embodiment a dose of Compound (I) difumarate equivalent to 240 mg of Compound (I) is administered twice a day.

Biological Assays

The inhibitory activities of Compound (I) and Compound (I) difumarate may be measured in the assays described in WO2005/028469 or as described in the Examples herein.

The compounds of the present invention possess anti-proliferative properties such as anti-cancer properties that are believed to arise from their erbB family receptor tyrosine kinase inhibitory activity, and particularly a mixed erbB2/EGF and/or erbB3/EGF profile.

Accordingly, the compounds of the present invention are expected to be useful in the treatment of diseases or medical conditions mediated alone or in part by erbB receptor tyrosine kinases, i.e. the compounds may be used to produce an erbB receptor tyrosine kinase inhibitory effect in a warm-blooded animal in need of such treatment. Thus the compounds of the present invention provide a method for the treatment of malignant cells characterised by inhibition of one or more of the erbB family of receptor tyrosine kinases. Particularly the compounds of the invention may be used to produce an anti-proliferative and/or pro-apoptotic and/or anti-invasive effect mediated alone or in part by the inhibition of erbB receptor tyrosine kinases. Particularly, the compounds of the present invention are expected to be useful in the prevention or treatment of those tumours that are sensitive to inhibition of one or more of the erbB receptor tyrosine kinases, that are involved in the signal transduction steps which drive proliferation and survival of these tumour cells. Accordingly the compounds of the present invention are expected to be useful in the treatment of psoriasis, benign prostatic hyperplasia (BPH), atherosclerosis and restenosis and/or cancer by providing an anti-proliferative effect, particularly in the treatment of erbB receptor tyrosine kinase sensitive cancers. Such benign or malignant tumours may affect any tissue and include non-solid tumours such as leukaemia, multiple myeloma or lymphoma, and also solid tumours, for example bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancers.

Where cancer is referred to, particularly it refers to oesophageal cancer, myeloma, hepatocellular, pancreatic, cervical cancer, Ewing's tumour, neuroblastoma, Kaposi's sarcoma, ovarian cancer, breast cancer, colorectal cancer, prostate cancer, bladder cancer, melanoma, lung cancer—non small cell lung cancer (NSCLC), and small cell lung cancer (SCLC), gastric cancer, head and neck cancer, brain cancer, renal cancer, lymphoma and leukaemia. In one embodiment it refers to breast cancer, for example hormone receptor-positive breast cancer. In another embodiment cancer refers to SCLC, NSCLC, colorectal cancer, ovarian cancer and/or breast cancer. In another embodiment cancer refers to SCLC. In another embodiment cancer refers to gastric cancer. In addition, it refers to NSCLC. In addition, it refers to colorectal cancer. In addition, it refers to ovarian cancer. In addition, more particularly it refers to breast cancer. In addition, more particularly it refers to hormone receptor positive breast cancer, especially to hormone receptor positive breast cancer in post-menopausal women. In one embodiment it refers to early stage non-metastatic hormone receptor positive breast cancer, for example early stage non-metastatic hormone receptor positive breast cancer in post-menopausal women. Still furthermore it refers to early stage non-metastatic estrogen and/or progesterone receptor positive breast cancer, especially to early stage non-metastatic estrogen and/or progesterone receptor positive breast cancer in post-menopausal women. In addition, more particularly it refers to metastatic hormone receptor positive breast cancer, especially to metastatic hormone receptor positive breast cancer in post-menopausal women. Still furthermore it refers to metastatic estrogen and/or progesterone receptor positive breast cancer, especially to metastatic estrogen and/or progesterone receptor positive breast cancer in post-menopausal women. Furthermore, it refers to bladder cancer, oesophageal cancer, gastric cancer, melanoma, cervical cancer and/or renal cancer. In addition it refers to endometrial, liver, stomach, thyroid, rectal and/or brain cancer. In another embodiment of the invention, particularly the cancer is in a non-metastatic state. In another embodiment of the invention, particularly the cancer is in a metastatic state. In a further embodiment of the invention, particularly the cancer is in a metastatic state, and more particularly the cancer produces skin metastases. In a further embodiment of the invention, particularly the cancer is in a metastatic state, and more particularly the cancer produces lymphatic metastases. In a further embodiment of the invention, particularly the cancer is in a metastatic state, and more particularly the cancer produces brain metastases.

Where the treatment of cancer is referred to particularly this is the treatment of cancerous tumours expressing one or more of the erbB family of receptors, for example EFGR, erbB2 and/or erbB3 receptors. The anti-cancer effect of Compound (I) difumarate according to the invention may be measured in terms of one or more of the anti-tumour effect, the extent of the response (for example reduced tumour volume or reduced tumour burden), the response rate, the clinical benefit rate (the sum of complete response, partial response and stable disease) the time to disease progression, progression-free survival and the overall survival rate. Such clinical trial endpoints are well known and are described in for example the FDA publication "Guidance for Industry Clinical Trial Endpoints for the Approval of Cancer Drugs and Biologics" May 2007 (www.fda.gov/CbER/gdlns/clintrialend.htm). The anti-tumour effects of Compound (I) difumarate according to the invention may be for example, one or more of inhibition of tumour growth, tumour growth delay, regression of tumour, shrinkage of tumour, increased time to regrowth of tumour on cessation of treatment or slowing of disease progression.

The use of Compound (I) difumarate may also have a beneficial effect in preventing the onset of cancer in warm-blooded animals, such as man.

According to this aspect of the invention there is provided Compound (I) difumarate, for use as a medicament.

According to a further aspect of the invention there is provided Compound (I) difumarate, for use in the production of an anti-proliferative effect in a warm-blooded animal such as man.

Thus according to this aspect of the invention there is provided the use of Compound (I) difumarate in the manufacture of a medicament for use in the production of an anti-proliferative effect in a warm-blooded animal such as man.

According to a further feature of this aspect of the invention there is provided a method for producing an anti-proliferative effect in a warm-blooded animal, such as man, in need of such treatment which comprises administering to said animal an effective amount of Compound (I) difumarate.

According to a further aspect of the invention there is provided Compound (I) difumarate, for use in the prevention or treatment of those tumours which are sensitive to inhibition of erbB receptor tyrosine kinases, such as a combination of EGFR and erbB2 and/or EGFR and erbB3, that are involved in the signal transduction steps which lead to the proliferation of tumour cells.

According to a further aspect of the invention there is provided the use of Compound (I) difumarate in the manufacture of a medicament for use in the prevention or treatment of those tumours which are sensitive to inhibition of erbB receptor tyrosine kinases, such as a combination of EGFR and erbB2 and/or EGFR and erbB3, that are involved in the signal transduction steps which lead to the proliferation of tumour cells.

According to a further feature of this aspect of the invention there is provided a method for the prevention or treatment of those tumours which are sensitive to inhibition of one or more of the erbB family of receptor tyrosine kinases, such as a combination of EGFR and erbB2 and/or EGFR and erbB3, that are involved in the signal transduction steps which lead to the proliferation and/or survival of tumour cells which comprises administering to said animal an effective amount of Compound (I) difumarate.

According to a further aspect of the invention there is provided the use of Compound (I) difumarate in the manufacture of a medicament for use in providing a combined EGFR and erbB2 tyrosine kinase inhibitory effect.

According to a further feature of this aspect of the invention there is provided a method for providing a combined EGFR and erbB2 tyrosine kinase inhibitory effect which comprises administering to said animal an effective amount of Compound (I) difumarate.

According to a further feature of this aspect of the invention there is provided Compound (I) difumarate, for use in providing a combined EGFR and erbB2 tyrosine kinase inhibitory effect.

According to a further aspect of the invention there is provided the use of Compound (I) difumarate in the manufacture of a medicament for use in providing a tyrosine kinase inhibitory effect on two or more receptors selected from EGFR, erbB2 and erbB3.

According to a further feature of this aspect of the invention there is provided a method for providing a tyrosine kinase inhibitory effect on two or more receptors selected from EGFR, erbB2 and erbB3, which comprises administering to said animal an effective amount of Compound (I) difumarate.

According to a further feature of this aspect of the invention there is provided Compound (I) difumarate, for use in providing a tyrosine kinase inhibitory effect on two or more receptors selected from EGFR, erbB2 and erbB3.

According to a further aspect of the invention there is provided the use of Compound (I) difumarate in the manufacture of a medicament for use in the treatment of a condition (for example a tumour) mediated in whole or part by the phosphorylation of an erbB2/erbB3 heterodimer.

According to a further feature of this aspect of the invention there is provided a method for the treatment of a condition (for example a tumour) mediated in whole or part by the phosphorylation of an erbB2/erbB3 heterodimer, which comprises administering to said animal an effective amount of Compound (I) difumarate.

According to a further feature of this aspect of the invention there is provided Compound (I) difumarate, for use in the treatment of a condition (for example a tumour) mediated in whole or part by the phosphorylation of an erbB2/erbB3 heterodimer.

According to a further aspect of the present invention there is provided the use of Compound (I) difumarate in the manufacture of a medicament for use in the treatment of a cancer (for example a cancer selected from leukaemia, multiple myeloma, lymphoma, bile duct, bone, bladder, brain/CNS, breast, colorectal, endometrial, gastric, head and neck, hepatic, lung (particularly non-small cell lung cancer), neuronal, oesophageal, ovarian, pancreatic, prostate, renal, skin, testicular, thyroid, uterine and vulval cancer and particularly a cancer selected from breast, gastric, colorectal, head and neck, ovarian and lung cancer, more particularly breast cancer).

According to a further feature of this aspect of the invention there is provided a method for treating a cancer (for example a cancer selected from leukaemia, multiple myeloma, lymphoma, bile duct, bone, bladder, brain/CNS, breast, colorectal, endometrial, gastric, head and neck, hepatic, lung (particularly non-small cell lung cancer), neuronal, oesophageal, ovarian, pancreatic, prostate, renal, skin, testicular, thyroid, uterine and vulval cancer and particularly a cancer selected from breast, gastric, colorectal, head and neck, ovarian and lung cancer, more particularly breast cancer in a warm-blooded animal, such as man, in need of such treatment, which comprises administering to said animal an effective amount of Compound (I) difumarate.

According to a further aspect of the invention there is provided Compound (I) difumarate, for use in the treatment of a cancer (for example selected from leukaemia, multiple myeloma, lymphoma, bile duct, bone, bladder, brain/CNS, breast, colorectal, endometrial, gastric, head and neck, hepatic, lung (particularly non-small cell lung cancer), neuronal, oesophageal, ovarian, pancreatic, prostate, renal, skin, testicular, thyroid, uterine and vulval cancer and particularly a cancer selected from breast, gastric, colorectal, head and neck, ovarian and lung cancer, more particularly breast cancer).

As mentioned above the size of the dose required for the therapeutic or prophylactic treatment of a particular disease will necessarily be varied depending upon, amongst other things, the host treated, the route of administration and the severity of the illness being treated.

According to a further aspect of the invention there is provided a pharmaceutical composition which comprises Compound (I) difumarate, in association with a pharmaceutically acceptable diluent or carrier for use in the treatment of a cancer For the avoidance of doubt, where the treatment of cancer is indicated, it is to be understood that this also refers to the prevention of metastases and the treatment of metastases, i.e. cancer spread. Therefore Compound (I) and Compound (I) difumarate of the present invention could be used to treat a patient who has no metastases to stop them occurring, or to lengthen the time period before they occur, and to a patient who already has metastases to treat the metastases themselves. Furthermore the treatment of cancer also refers to treatment of an established primary tumour or tumours and developing primary tumour or tumours. In one aspect of the invention the treatment of cancer relates to the prevention of metastases. In another aspect of the invention the treatment of cancer relates to the treatment of metastases. In another aspect of the invention the treatment of cancer relates to treatment of an established primary tumour or tumours or developing primary tumour or tumours. In one embodiment the treatment of cancer relates to an adjuvant treatment. In another embodiment the treatment of cancer refers to the neo-adjuvant treatment of cancer. Accordingly in an embodiment of the invention the Compound (I) difumarate according to the invention is used as an adjuvant treatment of hormone sensitive breast cancer, particularly as an adjuvant treatment of estrogen receptor positive breast cancer in post-menopausal women. In another embodiment of the invention the Compound (I) difumarate according to the invention is used as a neo-adjuvant treatment of hormone sensitive breast cancer, particularly as a neo-adjuvant treatment of estrogen and/or progesterone receptor breast cancer in post-menopausal women. In another embodiment the Compound (I) difumarate is used to treat advanced (metastatic) hormone sensitive (estrogen and/or progesterone receptor positive) breast cancer, particularly advanced estrogen receptor positive cancer in post-menopausal women.

In a further embodiment the Compound (I) difumarate according to the invention may be used as a neo-adjuvant therapy in the treatment of hormone sensitive breast cancer in patients. In another embodiment the Compound (I) difumarate according to the invention is not used as a neo-adjuvant treatment.

The term "adjuvant therapy" refers to a treatment given following removal of the primary tumour. Where the cancer is breast cancer, removal of the primary tumour may be effected by, for example, surgery (for example lumpectomy or mastectomy) and/or radiotherapy.

The term "neo-adjuvant therapy" refers to a treatment given prior to removal of the primary tumour by surgery or radiotherapy.

Herein, the treatment of cancer also refers to the prevention of cancer per se.

In one embodiment of the invention the Compound (I) difumarate is used in combination with an endocrine agent suitable for use in the treatment of breast cancer. For example, a combination of Compound (I) difumarate and an endocrine agent selected from an aromatase inhibitor, a selective estrogen receptor modulator, an LHRH agonist and an estrogen receptor down-regulator. For example, a combination of Compound (I) difumarate and an aromatase inhibitor. For example a combination of Compound (I) difumarate and tamoxifen. For example a combination of Compound (I) difumarate and anastrozole. For example a combination of Compound (I) difumarate and letrozole. For example a combination of Compound (I) difumarate and exemestane. The combination of Compound (I) difumarate and an endocrine therapy may be particularly suitable for use in the treatment of breast cancer as described herein. For example, the combination may be useful in the treatment of metastatic estrogen and/or progesterone positive breast cancer. Alternatively the combination may be useful as an adjuvant treatment of breast cancer, particularly as an adjuvant treatment of estrogen and/or progesterone positive breast cancer. The combination may also be useful in the treatment of estrogen and/or progesterone positive breast cancer in patients that have not received prior endocrine therapy (for example a selective estrogen receptor modulator such as tamoxifen, an aromatase inhibitor such as anastrozole or an estrogen receptor down-regulator).

Accordingly, in one embodiment of the invention there is provided a method for the treatment of advanced (metastatic) estrogen and/or progesterone positive breast cancer in a warm-blooded animal, such as man, in need of such treatment, which comprises administering to said animal an effective amount of Compound (I) difumarate in combination with an effective amount of an aromatase inhibitor such as anastrozole, wherein said animal has not previously been treated with an endocrine therapy such as for example, a selective estrogen receptor modulator such as tamoxifen, an aromatase inhibitor such as anastrozole or an estrogen receptor down-regulator.

In another embodiment of the invention there is provided a method for the treatment of non-metastatic estrogen and/or progesterone positive breast cancer in a warm-blooded animal, such as man, in need of such treatment, which comprises administering to said animal an effective amount of Compound (I) difumarate in combination with an effective amount of an aromatase inhibitor such as anastrozole, wherein said animal has not previously been treated with an endocrine therapy such as for example, a selective estrogen receptor modulator such as tamoxifen, an aromatase inhibitor such as anastrozole or an estrogen receptor down-regulator. In this embodiment the combination is suitably administered as an adjuvant treatment.

In the above two embodiments for the treatment of breast cancer, the warm-blooded animal is suitably a post-menopausal woman. The term "post-menopausal" includes women that are naturally post-menopausal and women where the menopause has been induced, by for example, treatment with an LHRH agonist such as goserelin. It is to be understood that where herein it is stated that a patient "not previously been treated with an endocrine therapy", it is intended that the treatment of a patient with an LHRH agonist to induce early menopause in the patient is not considered to be "previously treated with an endocrine therapy". Accordingly, patients that have been treated with an LHRH agonist to induce early menopause are not excluded from those embodiments that are described herein as not being "treated with an endocrine therapy".

In another embodiment the Compound (I) difumarate is used in combination with a taxane such as paclitaxel or docetaxel. This combination may be useful in the treatment of breast cancer. For example, in the treatment of a breast cancer (particularly advanced/metastatic breast cancer) which has a low over-expression of erbB2. The term "low over-expression of erbB2" refers to tumours that are Her2 fluorescent in-situ hybridization (FISH) negative. Particular tumours that are "low over-expression of erbB2" those that are:

(i) Her2+ by immunohistochemistry (IHC); and/or
(ii) Her2++ by IHC and Her2 fluorescent in-situ hybridization (FISH) negative.

Accordingly in a particular embodiment of the invention the Compound (I) difumarate is used in combination with a taxane such as paclitaxel or docetaxel in the treatment of a cancer with low over-expression of erbB2 selected from one or more of:

(a) a breast cancer which is Her2 FISH negative;
(b) a breast cancer which is Her2+ by IHC; and
(c) a breast cancer which is Her2++ by IHC and Her2 FISH negative.

According to a further aspect of the present invention there is provided a method for the treatment of breast cancer with low over-expression of erbB2 in a warm-blooded animal, such as man, in need of such treatment, which comprises administering to said animal an effective amount of Compound (I) difumarate in combination with an effective amount of a taxane such as paclitaxel or docetaxel.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

As will be understood the references to the use of Compound (I) difumarate described in the methods, uses and pharmaceutical compositions described herein, refer to any of the difumarates described herein, for example Form A.

EXAMPLES

The invention is further illustrated by way of the following examples, which are intended to elaborate several embodiments of the invention. These examples are not intended to, nor are they to be construed to, limit the scope of the invention. It will be clear that the invention may be practiced otherwise than as particularly described herein. Numerous modifications and variations of the present invention are possible in view of the teachings herein and, therefore, are within the scope of the invention.

In the Examples unless otherwise stated:

(i) yields are given for illustration only and are not necessarily the maximum attainable;

(ii) melting points were determined by DSC analysis using a Mettler DSC820e apparatus; 1-2 mg samples were accurately weighed and analysed in a vented sample pan; heating was carried out at 10° C./minute from 25° C. to 325° C.; unless states otherwise melting points herein refer to the onset temperature of the melting endotherm measured using DSC;

(iii) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is $(MH)^-$ which refers to the protonated mass ion; reference to $M^+$ is to the mass ion generated by loss of an electron; and reference to $M-H^+$ is to the mass ion generated by loss of a proton;

(iv) when given, NMR data is in the form of delta values for major diagnostic protons, given in parts per million (ppm) relative to tetramethylsilane (TMS) as an internal standard, determined at 500 MHz using perdeuterio dimethyl sulfoxide (DMSO-$d_6$) as solvent unless otherwise indicated; the following abbreviations have been used: s, singlet; d, doublet; t, triplet; q, quartet; m, multiplet; br, broad;

(v) chemical symbols have their usual meanings; SI units and symbols are used;

(vi) solvent ratios are given in volume:volume (v/v) terms;

(vii) thermogravimetric analysis was carried out using Mettler TG851 equipment [1-5 mg samples were accurately weighed and analysed in an open pan; heating was carried out at 10° C./minute from 25° C. to 325° C.

(viii) X-Ray Powder Diffraction analysis was carried out using a Siemens D5000 powder X-ray diffractometer fitted with a scintillation detector; the X-Ray source was Cu $K_\alpha$, giving a wavelength of 1.54 Å; data were collected over the range 2-theta 2-40°, in increments of 2-theta 0.02°, with 1 second per increment and was categorised into the categories identified in Table 2 below:

TABLE 2

| % Relative Intensity* | Definition |
| --- | --- |
| 25-100 | vs (very strong) |
| 10-25 | s (strong) |
| 3-10 | m (medium) |
| 1-3 | w (weak) |

*The relative intensities are derived from diffractograms measured with fixed slits

[As previously stated, persons skilled in the art of X-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values (see Jenkins, R & Snyder, R. L. 'Introduction to X-Ray Powder Diffractometry' John Wiley & Sons, 1996, for further information)];

(ix) dynamic vapour sorption was measured using a SMS DVS (Surface Measurement Systems Limited, UK). Samples were analysed at 25° C. using a gas flow of 200 cubic centimeters per minute. The relative humidity (RH) was increased from 0% RH in steps of 10% RH to 80% RH with the final step of 95% RH. The sample was then desorbed using the same RH step pattern as the sorption; this procedure was then repeated in a second sorption/desorption cycle. Equilibration at each humidity step is set such that the rate of change of weight with time (minute) was 0.002%.

(x) intrinsic dissolution rate was measured in a dissolution bath coupled to a fibre optic uv detector.

(xi) solubility in water was measured using HPLC UV.

(xii) in the examples given below the number of moles and the yield stated refer to the raw materials and reagents at 100% w/w, thereby taking account of the purity of the materials used.

Example A

Preparation of 4-(3-Chloro-2-fluoroanilino)-7-methoxy-6-{[1-(N-methylcarbamoylmethyl)piperidin-4-yl]oxy}quinazoline (Compound (I))

2-Chloro-N-methylacetamide (3.720 kg, 34.60 mol) and 4-(3-chloro-2-fluoroanilino)-7-methoxy-6-[(piperidin-4-yl)oxy]quinazoline dihydrochloride (13.70 kg, 27.25 mol), were dissolved in acetonitrile (79.2 kg). To the stirred suspension, at ambient temperature, was added triethylamine (17.40 kg, 172.11 mol). The resulting clear solution was heated to reflux and held for 3 hours. The solution was cooled to 20° C. (product crystallized at 50° C.). Water (54.2 kg) was added to the reactor and the suspension was stirred for a further 2 hours at 20° C. The product was filtered and washed with water (34 kg) followed by cold (0° C.) acetonitrile (13.0 kg). The product was recrystallised from acetonitrile (94.6 kg), isolated by filtration and washed with cold (0° C.) acetonitrile (13.2 kg). A further recrystallisation of this product was then carried out as above from acetonitrile (75.2 kg). The solid was then dried under vacuum to give the title product as a white solid (6.50 kg, 50%); $^1$H NMR Spectrum: (CDCl$_3$) 1.98 (m, 2H), 2.08 (m, 2H), 2.46 (-m, 2H), 2.85 (m, 2H), 2.87 (d, 3H), 3.07 (s, 2H), 4.02 (s, 3H), 4.49 (m, 1H), 7.16 (m, 4H), 7.31 (m, 2H), 8.49 (m, 1H), 8.71 (s, 1H); Mass spectrum: MH$^-$ 474.

The 4-(3-Chloro-2-fluoroanilino)-7-methoxy-6-[(piperidin-4-yl)oxy]quinazoline used as the starting material was prepared as follows:

Step 1: 6-Acetoxy-4-(3-chloro-2-fluoroanilino)-7-methoxyquinazoline hydrochloride 6-Acetoxy-7-methoxyquinazolin-4-one (International Patent Application WO 96/15118, Example 39 thereof; 21.4 kg, 89.3 mol) was suspended in toluene (150 kg). To this was added N-ethyldiisopropylamine (13.3 kg, 103 mol). The brown suspension was heated to 70° C. then phosphorus oxychloride (36.0 kg, 228 mol) was charged. The reaction mixture was stirred at 70° C. for 5 hours. Further toluene (84.0 kg) was added followed by 3-chloro-2-fluoroaniline (14.88 kg, 102 mol). The reaction mixture was stirred at 70° C. for 2 hours during which time a solid precipitated. The suspension was cooled to 25° C. and held at this temperature for 93 hours. The reaction mixture was filtered and the filter cake washed with toluene (2×55.5 kg). The cake was further washed with a mixture of ethanol (24.5 kg) and water (32.0 kg) twice, then ethanol (50.5 kg) twice and the solid then dried under vacuum to give the title product as a beige solid (33.4 kg, 78%); $^1$H NMR: 2.37 (s, 3H), 4.00 (s, 3H), 7.34 (ddd, 1H), 7.48 (s, 1H), 7.52 (ddd, 1H), 7.61 (ddd, 1H), 8.62 (s, 1H), 8.86 (s, 1H); Mass Spectrum: 362.4, 364.4.

Step 2: 4-(3-Chloro-2-fluoroanilino)-6-hydroxy-7-methoxyquinazoline

6-Acetoxy-4-(3-chloro-2-fluoroanilino)-7-methoxyquinazoline hydrochloride from step 1 (33.5 kg, 69.6 mol) was suspended in methanol (198 kg). To the stirred suspension at 25° C. was added water (86 kg) and sodium hydroxide (31.5 kg, 32%). The resulting solution was stirred at 60° C. for 4.5 hours and then cooled to 25° C. Acetic acid (approximately 16.0 kg) was added until a pH of 5.5-6.0 was achieved at which point the product precipitates from solution. After the addition of further methanol (5.5 kg) the suspension was stirred for 90 minutes. The product was filtered then washed with 25% aqueous methanol (39.0 kg MeOH+17.0 kg Water) and then methanol (55.5 kg). The crude solid was dried under vacuum at 40° C. The crude solid was slurried with water (145 kg) and stirred for 2 hours at 65° C. The slurry was cooled to 20° C. and filtered. The filter cake was washed with methanol (2×21.5 kg), then dried under vacuum at 40° C. to give a the title product as a light brown solid (21.85 kg, 98%); $^1$H NMR: 3.95 (s, 3H), 7.19 (s, 1H), 7.23 (dd, 1H), 7.42 (dd, 1H), 7.50 (dd, 1H), 7.64 (s, 1H), 8.32 (s, 1H), 9.43 (s, 1H), 9.67 (br.s, 1H); Mass Spectrum: 320.4, 322.4.

Step 3: 6-{[1-tert-Butoxycarbonyl)piperidin-4-yl]oxy}-4-(3-chloro-2-fluoroanilino)-7-methoxy quinazoline 4-(3-Chloro-2-fluoroanilino)-6-hydroxy-7-methoxyquinazoline from Step 2 (15.591 kg, 48.44 mol), tert-Butyl (4-methanesulfonyloxy)piperidine-1-carboxylate (prepared as in Chemical & Pharmaceutical Bulletin 2001, 49(7), 822-829; 16.20 kg, 57.99 mol) and potassium carbonate (7.978 kg, 57.73 mol) were dissolved in N-methylpyrrolidinone (114.2 kg), and the mixture was heated to 100° C. with stirring. Heating was continued at 100° C. (95° C.-105° C.) for 5 hours. The mixture was then cooled to 80° C. and quenched by the addition of water (216.6 kg).

The batch was stirred at 80° C. for a further 60 minutes then cooled to 20° C. over 2 hours, during which time the product crystallized. The product was isolated by filtration. The product was dissolved in hot (reflux) methanol (200 L). To this mixture was added water (20 L), which induced crystallization. The suspension was cooled to 0° C. and filtered. Vacuum drying at 50° C. afforded the title product, 18.80 kg (77%); $^1$H NMR: 1.40 (s, 9H), 1.60-1.65 (m, 2H), 1.95-2.00 (m, 2H), 3.20-3.25 (m, 2H), 3.65-3.70 (m, 2H), 3.92 (s, 3H), 4.68 (m, 1H), 7.21 (s, 1H), 7.27 (dd, 1H), 7.47 (ddd, 1H), 7.51 (dd, 1H), 7.85 (s, 1H), 8.36 (s, 1H), 9.53 (s, 1H); Mass Spectrum: 503.5, 505.5.

Step 4: 4-(3-chloro-2-fluoroanilino)-7-methoxy-6-[(piperidin-4-yl)oxy]quinazoline dihydrochloride 6-{[(1-tert-Butoxycarbonyl)piperidin-4-yl]oxy}-4-(3-chloro-2-fluoroanilino)-7-methoxyquinazoline from step 3 (18.80 kg, 37.38 mol) was suspended in isopropanol (139.8 kg), and heated to 40° C. with stirring. Hydrochloric acid (15.40 kg, 156.3 mol) was charged to the vessel over 50 minutes, allowing an exotherm of approximately 9° C. to occur. During the charging of the acid, the suspension dissolved to give a clear solution. The solution was heated slowly to reflux over approximately 90 minutes, and then held at reflux for a further 3 hours. The product crystallised out during this reflux period. The thick suspension was cooled to 0° C. and filtered. The filter cake was washed twice with cold (0° C.) isopropanol (2×20.6 kg). The product was dried under vacuum at 50° C. to give the title product, 13.60 kg (73%); $^1$H NMR: 1.53-1.64 (m, 2H), 2.00-2.05 (m, 2H), 2.64-2.72 (m, 2H), 3.00-3.07 (m, 2H), 3.92 (s, 3H), 4.60 (m, 1H), 7.20 (s, 1H), 7.26 (dd, 1H), 7.47 (dd, 1H), 7.50 (dd, 1H), 7.82 (s, 1H), 8.34 (s, 1H), 9.56 (s, 1H); Mass Spectrum: 403.2, 405.2.

Example B Preparation of 4-(3-Chloro-2-fluoroanilino)-7-methoxy-6-{[1-(N-methylcarbamoylmethyl)piperidin-4-yl]oxy}quinazoline (Compound (I))

2-Chloro-N-methylacetamide (24.22 g, 223.1 mmol) and 4-(3-chloro-2-fluoroanilino)-7-methoxy-6-[(piperidin-4-yl)oxy]quinazoline dihydrochloride (86.00 g, 160.9 mmol), were slurried in acetonitrile (537 ml). To the stirred suspension, at ambient temperature, was added triethylamine (101 ml, 723.9 mmol). The reaction was heated to 75° C. held for 5 hours. The solution was cooled to 70° C. and ethanol (268 ml) added. The reaction was cooled to 45° C. and water (9.6 ml) added. Compound (I) (0.42 g) was added to establish crystallisation and then the slurry cooled to 20° C. over 2 hours. After stirring for a further 12 hours the product was isolated by filtration. The filter cake was washed twice with acetonitrile (102 ml): ethanol (51 ml): water (1.8 ml) and then with water (153 ml). The product was dried in vacuo at 60° C. to give the title compound as a white solid (45.9 g, 60%); 1H NMR (400 MHz, DMSO-$d_6$) δ ppm 1.76-1.87 (m, 2H) 2.01-2.11 (m, 2H) 2.35-2.44 (m, 2H) 2.64 (d, J=4.74 Hz, 3H) 2.72-2.80 (m, 2H) 2.95 (s, 2H) 3.95 (s, 3H) 4.51-4.63 (m, 1H) 7.23 (s, 1H) 7.29 (td, J=8.08, 1.29 Hz, 1H) 7.46-7.58 (m, 2 H) 7.75 (q, J=4.60 Hz, 1H) 7.83 (s, 1H) 8.38 (s, 1H) 9.59 (s, 1H) Mass spectrum: MH$^+$474.

The 4-(3-chloro-2-fluoroanilino)-7-methoxy-6-[(piperidin-4-yl)oxy]quinazoline dihydrochloride used as the starting material was prepared as follows:

Step 1: 6-{[(1-tert-Butoxycarbonyl)piperidin-4-yl]oxy}-4-(3-chloro-2-fluoroanilino)-7-methoxy quinazoline 4-(3-Chloro-2-fluoroanilino)-6-hydroxy-7-methoxyquinazoline (prepared as described in Step 2 of Example A; 60.00 g, 0.1828 mol), tert-Butyl (4-methanesulfonyloxy)piperidine-1-carboxylate (88.04 g, 0.3107 mol) and potassium carbonate (30.31 g, 0.2193 mol) were suspended in ethanol (584 ml) and water (58 ml), and the mixture was heated to reflux with stirring. Heating was continued at reflux for 16.5 hours. The mixture was then cooled to 70° C. and water (234 ml) was added over 60 minutes.

The batch was stirred at 65° C. for a further 2 hours to establish crystallisation. The slurry was cooled to 20° C. over 6 hours. The product was isolated by filtration. The filter cake was slurried with aqueous ethanol (ethanol 117 ml, water 58 ml) and then displacement washed with aqueous ethanol (ethanol 117 ml, water 58 ml). The filter cake was then slurried with water (175 ml) and then displacement washed with water (175 ml). The product was dried in vacuo at 40° C. to give the title compound (81.5 g, 84%); 1H NMR (500 MHz, DMSO-$d_6$) δ ppm 1.42 (s, 9H) 1.60-1.70 (m, 2H) 1.96-2.04 (m, 2H) 3.23-3.30 (m, 2H) 3.65-3.75 (m, 2H) 3.95 (s, 3H) 4.68-4.75 (m, 1H) 7.24 (s, 1H) 7.29 (t, J=8.06 Hz, 1H) 7.49 (t, J=7.50 Hz, 1H) 7.54 (t, J=7.19 Hz, 1H) 7.88 (s, 1H) 8.39 (s, 1H) 9.57 (s, 1H); Mass Spectrum: 503.5, 505.5.

Step 2: 4-(3-chloro-2-fluoroanilino)-7-methoxy-6-[(piperidin-4-yl)oxy]quinazoline dihydrochloride 6-{[(1-tert-Butoxycarbonyl)piperidin-4-yl]oxy}-4-(3-chloro-2-fluoroanilino)-7-methoxyquinazoline (10.00 g, 0.1879 mol) was suspended in industrial methylated spirits (95 ml), and heated to 35° C. with stirring. Hydrochloric acid (6.59 ml, approximately 0.7891 mol) was charged to the vessel allowing an exotherm of approximately 5.5° C. to occur. During the charging of the acid, the suspension dissolved to give a clear solution. The solution was heated slowly to 70° C. over approximately 90 minutes, and then held at 70° C. for a further 1 hour. The reaction is then cooled to 0° C. over 4 hours during which time the product crystallises. The product was isolated by filtration and then filter cake was washed twice with industrial methylated spirits (2×14 ml). The product was dried in vacuo at 50° C. to give the title product (9.04 g, 88%); 1H NMR (400 MHz, DMSO-$d_6$) δ ppm 1.91-2.01 (m, 2H) 2.27-2.35 (m, 2H) 3.15-3.26 (m, 2H) 3.26-3.35 (m, 2H) 4.02 (s, 3H) 5.07-5.15 (m, 1H) 7.35 (td, J=8.08, 1.29 Hz, 1H) 7.46 (s, 1H) 7.52 (ddd, J=8.03, 5.23 Hz, 1H) 7.63 (ddd, J=8.22, 6.76, 1.62 Hz, 1H) 8.83 (s, 1H) 8.91 (s, 1H) 9.02-9.13 (m, 1H) 9.20-9.31 (m, 1H) 12.51 (br. s., 1H)); Mass Spectrum: 403.2, 405.2.

Example C Preparation of 4-(3-Chloro-2-fluoroanilino)-7-methoxy-6-{[1-(N-methylcarbamoylmethyl)piperidin-4-yl]oxy}quinazoline (Compound (I))

Compound (I) was prepared according to the scheme shown below:

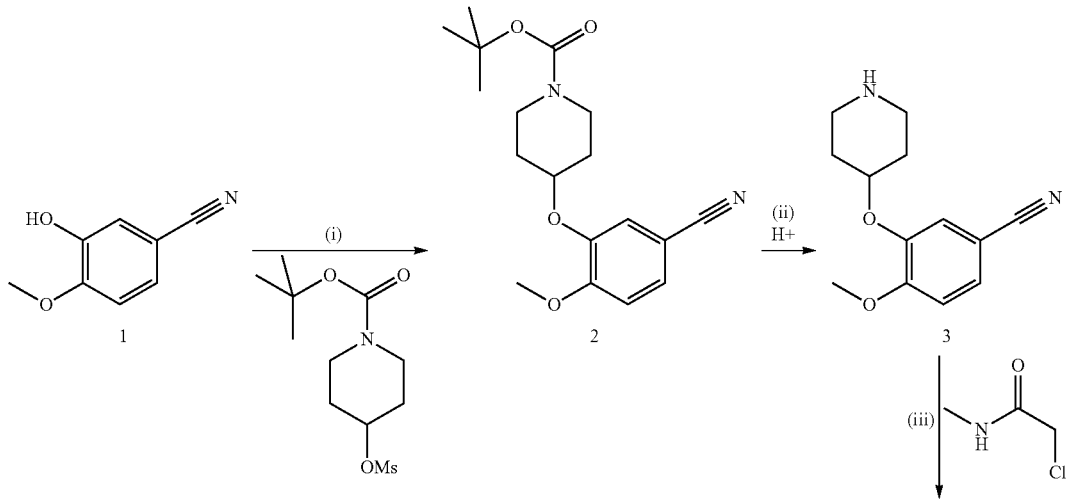

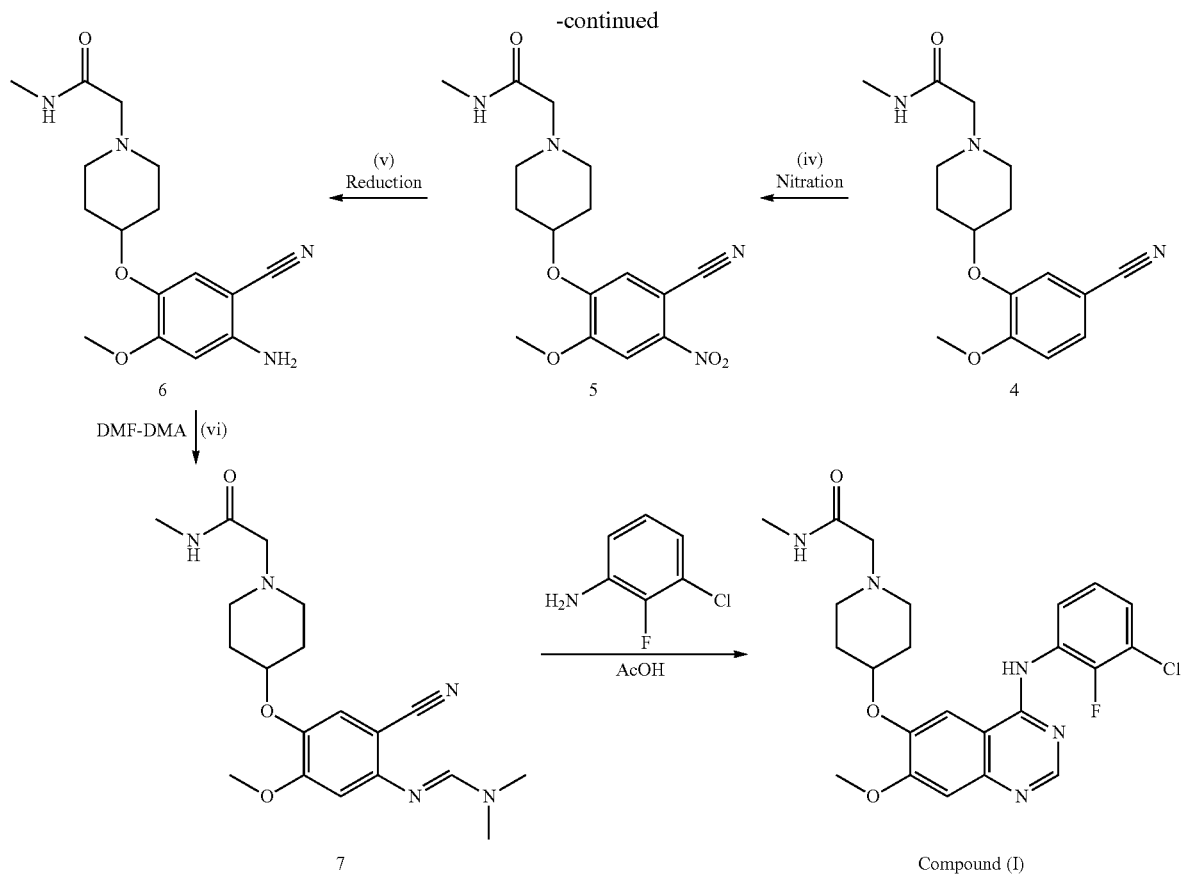

2-[4-(5-cyano-4-{[(dimethylamino)methylene]amino}-2-methoxyphenoxy)piperidin-1-yl]-N-methylacetamide (7, 7.00 g, 17.71 mmoles), was suspended in methoxybenzene (35.8 g). Acetic acid (16.6 g) was charged and to the resulting solution was added 3-chloro-2-fluoroaniline (2.71 g, 18.07 mmoles). The reaction mixture was heated at 90° C. for 20 hours then cooled to 20° C. Water (37.04 g) was charged to the reaction mixture, and the organic layer discarded. To the resulting aqueous mixture was charged isopropanol (39.00 g), followed by aqueous ammonia (20.79 g, 25%). The reaction mixture was heated to 30° C. and seeded with Compound (I), which induced crystallisation. The reaction was then cooled to 0° C. and the product isolated by filtration. The filter cake was washed twice with a mixture of water (7.28 g) and isopropanol (4.68 g), then dried to afford the Compound (I) (5.65 g, 55% yield); $^1$H NMR (400 MHz, DMSO-$d_6$) δ ppm 1.79 (m, 2H) 2.04 (m, 2H) 2.38 (m, 2H) 2.62 (d, J=4.5 Hz, 3H) 2.74 (m, 2H) 2.94 (s, 2H) 3.93 (s, 3H) 4.56 (tt, J=8.1, 3.8 Hz, 1H) 7.21 (s, 1H) 7.28 (m, 1H) 7.50 (m, 2H) 7.73 (q, J=4.5 Hz, 1H) 7.81 (s, 1H) 8.36 (s, 1H) 9.56 (br.s, 1H); Mass Spectrum: m/z (M+H)$^+$ 474.2, 476.2.

The 2-[4-(5-cyano-4-{[(dimethylamino)methylene]amino}-2-methoxyphenoxy)piperidin-1-yl]-N-methylacetamide (7), used as the starting material was prepared as follows:

Step 1. Preparation of tert-butyl 4-(5-cyano-2-methoxyphenoxy)piperidine-1-carboxylate (2)

3-hydroxy-4-methoxybenzonitrile (1, 6.00 g, 39.62 mmole), tert-butyl (4-methanesulfonyloxy)piperidine-1-carboxylate (16.6 g, 59.44 mmoles) (Chemical & Pharmaceutical Bulletin 2001, 49(7), 822-829); and potassium carbonate (6.71 g, 47.55 mmoles) were suspended in isopropanol (78.98 g) and the mixture was heated at reflux with stirring. Additional tert-butyl (4-methanesulfonyloxy)piperidine-1-carboxylate (2.08 g, 7.43 mmoles) was added to push the reaction to completion. The mixture was then cooled and quenched by the addition of water (100.47 g). Seeding with tert-butyl 4-(5-cyano-2-methoxyphenoxy)piperidine-1-carboxylate (2) followed by cooling to 0° C. resulted in a crystalline product, which was isolated by filtration. The filter cake was washed with a mixture of water (8.86 g) and isopropanol (6.97 g), followed by water (23.64 g) and then dried to give the title compound (10.75 g, 80% yield); $^1$H NMR (400 MHz, DMSO-$d_6$) δ ppm 1.39 (s, 9H) 1.48 (m, 2H) 1.88 (m, 2H) 3.13 (m, 2H) 3.67 (m, 2 H) 3.83 (s, 3H) 4.56 (tt, J=8.1, 3.8 Hz, 1H) 7.13 (d, J=8.4 Hz, 1H) 7.42 (dd, J=8.4, 1.9 Hz, 1H) 7.51 (d, J=1.9 Hz, 1H); Mass Spectrum: m/z (M+H)$^+$ 333.1.

Step 2. Preparation of 4-methoxy-3-(piperidin-4-yloxy)benzonitrile (3)

Tert-butyl 4-(5-cyano-2-methoxyphenoxy)piperidine-1-carboxylate (2, 39.31 g, 118.26 mmoles) was suspended in ethanol (155.53 g) and heated to 40° C. To this slurry was slowly added HCl (46.61 g, 573.04 mmoles). The mixture was heated to 60° C. and held for 3 hours. The reaction mixture was cooled to 20° C. and seed was charged initiating crystallisation. The resulting solid was isolated by filtration at 0° C., washed twice with ethanol (62.21 g) and then dried to give the title compound as the hydrochloride salt (29.84 g, 77% yield); $^1$H NMR (400 MHz, DMSO-d$_6$) δ ppm 1.84 (m, 2H) 2.09 (m, 2H) 3.02 (ddd, J=12.7, 8.9, 3.4 Hz, 2H) 3.20 (m, 2H) 3.84 (s, 3H) 4.63 (tt, J=7.7, 3.6 Hz, 1 H) 7.15 (d, J=8.5 Hz, 1H) 7.45 (dd, J=8.5, 1.9 Hz, 1H) 7.56 (d, J=1.9 Hz, 1H) 9.16 (br. s, 2H); Mass Spectrum: m/z (M+H)$^+$ 233.2.

Step 3. Preparation of 2-[4-(5-cyano-2-methoxyphenoxy)piperidin-1-yl]-N-methylacetamide (4)

4-Methoxy-3-(piperidin-4-yloxy)benzonitrile hydrochloride salt (3, 28.36 g, 95.82 mmoles), 2-chloro-N-methylacetamide (12.37 g, 114.98 mmoles) and potassium carbonate (33.11 g, 239.55 mmoles) were suspended in acetonitrile (161.36 g). The reaction mixture was heated at reflux for 3 hours. The reaction mixture was cooled to 20° C. and water (386.26 g) was charged. The reaction was heated to 75° C. and the volume reduced by distillation. Upon cooling crystallisation occurred. The resulting solid was isolated by filtration, washed twice with water (77.25 g and 128.75 g) and then dried to give the title compound (27.95 g, 94% yield); $^1$H NMR (400 MHz, DMSO-d$_6$) δ ppm 1.68 (m, 2H) 1.91 (m, 2H) 2.29 (m, 2H) 2.61 (d, J=4.7 Hz, 3H) 2.67 (m, 2H) 2.88 (s, 2H) 3.83 (s, 3H) 4.41 (tt, J=8.3, 4.0 Hz, 1H) 7.11 (d, J=8.4 Hz, 1H) 7.40 (dd, J=8.4, 1.9 Hz, 1 h) 7.47 (d, J=1.9 Hz, 1H) 7.68 (q, J=4.7 Hz, 1H); Mass Spectrum: m/z (M+H)$^+$ 304.2.

Step 4. Preparation of 2-[4-(5-cyano-2-methoxy-4-nitrophenoxy)piperidin-1-yl]-N-methylacetamide (5)

2-[4-(5-Cyano-2-methoxyphenoxy)piperidin-1-yl]-N-methylacetamide (4, 8.78 g, 26.11 mmoles) was suspended in acetic acid (22.82 g, 364.87 mmoles) and the resulting reaction mixture cooled to 5° C. To this was added sulfuric acid (23.64 g, 234.95 mmoles) maintaining the reaction temperature below 30° C. To the resulting solution was added nitric acid (2.40 g, 26.63 mmoles). The reaction mixture was then heated to 35° C. and held for 3 hours. Additional nitric acid (117 mg, 1.31 mmoles) and sulphuric acid (1.31 g 13.1 mmoles) were charged and the reaction mixture was heated at 35° C. for 30 minutes. The solution was cooled to 20° C. and quenched with aqueous ammonia (92.45 g 1.36 moles), resulting in an increase in temperature to 50° C. To the resulting slurry was added, propionitrile (61.58 g 1.12 moles) and water (19 g). The reaction mixture was heated to 80° C. resulting in a clear solution, which upon settling gave two layers. The bottom layer was removed. The reaction mixture was cooled to 20° C. resulting in a thick slurry. The solid was isolated by filtration, washed with propionitrile (6.16 g 112.0 mmoles) and dried to afford the title compound (7.44 g, 82% yield); $^1$H NMR (400 MHz, DMSO-d$_6$) δ ppm 1.72 (m, 2H) 1.97 (m, 2H) 2.35 (m, 2H) 2.61 (d, J=4.7 Hz, 3H) 2.66 (m, 2H) 2.90 (s, 2 H) 3.96 (s, 3H) 4.73 (tt, J=8.4, 4.0 Hz, 1H) 7.71 (q, J=4.7 Hz, 1H) 7.82 (s, 1H) 7.86 (s, 1 H). Mass Spectrum: m/z (M+H)$^+$ 349.2

Step 5. Preparation of 2-[4-(4-amino-5-cyano-2-methoxyphenoxy)piperidin-1-yl]-N-methylacetamide (6)

2-[4-(5-Cyano-2-methoxy-4-nitrophenoxy)piperidin-1-yl]-N-methylacetamide (5, 7.42 g, 19.38 mmoles) was suspended in water (44.52 g) and methanol (5.35 g). To this was added sodium dithionite (11.91 g, 58.15 mmoles) and the resulting reaction mixture was heated to 60° C. To the reaction mixture was added hydrochloric acid (46.98 g, 463.89 mmoles)), resulting in a solution, which was held at 60° C. for 3 hours. The reaction mixture was then allowed to cool to 20° C. Aqueous sodium hydroxide (15.51 g 182.2 mmoles) was charged followed by 2-methyltetrahydrofuran (58.0 g). The reaction mixture was heated to 60° C., which upon settling gave two layers and the lower aqueous layer was discarded. The volume of the reaction mixture was reduced by vacuum distillation and methyl tert-butyl ether (18.54 g) was added to give a slurry which was cooled to 10° C. and then the solid was collected by filtration. The solid was washed with 2-methyltetrahydrofuran (5.8 g) and dried to give the title compound (5.4 g, 78% yield); $^1$H NMR (400 MHz, DMSO-d$_6$) δ ppm 1.62 (m, 2H) 1.82 (m, 2H) 2.20 (m, 2H) 2.60 (d, J=4.7 Hz, 3H) 2.65 (m, 2H) 2.86 (s, 2H) 3.72 (s, 3H) 4.00 (tt, J=8.3, 4.0 Hz, 1H) 5.66 (br. s, 2H) 6.39 (s, 1H) 6.94 (s, 1H) 7.65 (q, J=4.7 Hz, 1H)

Mass Spectrum: m/z (M+H)$^+$ 319.2

Step 6. Preparation of 2-[4-(5-cyano-4-{[(dimethylamino)methylene]amino}-2-methoxyphenoxy)piperidin-1-yl]-N-methylacetamide (7)

2-[4-(4-Amino-5-cyano-2-methoxyphenoxy)piperidin-1-yl]-N-methylacetamide (6, 18.21 g, 52.05 mmoles) was suspended in 2-methyltetrahydrofuran (99.62 g). To this was added acetic acid (162.79 mg), and N,N-dimethylformamide dimethyl acetal (DMF-DMA) (8.63 g, 70.27 mmoles) and the resulting reaction mixture was heated at 76° C. for 16 hrs. Additional N,N-dimethylformamide dimethyl acetal (639.41 mg, 5.20 mmoles) was added to the reaction mixture to ensure the reaction completed. The reaction mixture was cooled to 30° C. during which time crystallisation occurred. The resulting solid was isolated by filtration, washed with 2-methyltetrahydrofuran (14.23 g) and dried to afford the title compound (19.53 g, 97% yield); $^1$H NMR (400 MHz, DMSO-d$_6$) δ ppm 1.65 (m, 2H) 1.86 (m, 2H) 2.24 (m, 2H) 2.60 (d, J=4.7 Hz, 3H) 2.66 (m, 2H) 2.87 (s, 2H) 2.95 (s, 3H) 3.04 (s, 3H) 3.81 (s, 3H) 4.19 (tt, J=8.2, 3.8 Hz, 1H) 6.72 (s, 1H) 7.15 (s, 1H) 7.67 (q, J=4.7 Hz, 1H) 7.90 (s, 1H); Mass Spectrum: m/z (M+H)$^+$ 374.2.

Biological Activity

The activity of Compound (I) was to assessed to test its ability to:

a) inhibit the activation (phosphorylation) of EGFR, ErbB2 and ErbB3 in ligand-stimulated cells; and b) inhibit the basal and ligand-stimulated proliferation of MCF-7 cells.

(a) Compound (I) in Ligand Driven Assays

Methods:

KB cells and MCF-7 cells were obtained from the American Type Culture Collection (ATCC) and routinely cultured in RPMI 1640 (Phenol red free)+10% Foetal Bovine Serum+2 mM L-Glutamine.

Treatment and Lysis of Cells:

KB cells were seeded at 5000 cells/well and MCF-7 cells at 4000 cells/well in 96 well plates in RPMI 1640 media containing 10% FBS. Cells were incubated for 72 hours before replacing the media with serum-free RPMI 1640 media for 24 hours. Cells were then treated with Compound (I) for 90 minutes at concentrations ranging from 0-10 μM. Immediately before cell lysis, MCF-7 and KB cells were incubated for 5 minutes with ligand (heregulin ("HRG") for the MCF-7 cells and epidermal growth factor ("EGF") for the KB cells) at concentrations required to increase receptor phosphorylation to 90% of max (ED$_{90}$) to allow inter-assay comparison.

Measurement of p-EGFR, p-ErbB2 and p-ErbB3:

The p-EGFR status of KB cells was measured using the Human phospho-EGFR Duoset ELISA kit (R&D systems total EGFR #DYC1854, pEGFR #DYC1095). The p-ErbB2 and p-ErbB3 content of MCF-7 cells were measured using the Human phospho-ErbB2 Duoset ELISA kit (R&D systems, DYC1768) and Human phospho-ErbB3 Duoset ELISA kit (R&D systems, DYC1769) respectively. The kits measured whole cell tyrosine phosphorylation of EGFR, ErbB2 or ErbB3. Assays were performed according to the manufacturers instructions, with 50 µl lysate added per well.
Results:
The results are summarised in Table 3

TABLE 3

Compound (I) activity against p-EGFR (in KB cells) and p-ErbB2 and p-ErbB3 (in MCF-7 cells)

| Compound | p-EGFR Geo Mean $IC_{50}$ (95% CIR*) | p-ErbB2 Geo Mean $IC_{50}$ (95% CIR) | p-ErbB3 Geo Mean $IC_{50}$ (95% CIR) |
|---|---|---|---|
| Compound (I) | 0.004 (1.377) | 0.003 (1.817) | 0.004 (1.89) |

*Confidence Interval Ratio

Table 3 shows that Compound (I) is a potent inhibitor of phospho-EGFR, phospho-ErbB2 and phospho-ErbB3 in these cells.

b) Compound (I) in Basal or HRG-Stimulated MCF-7 Cell Proliferation Assay
Methods:
MCF-7 cells were routinely cultured in DMEM (Phenol red free)+10% Foetal Bovine Serum+2 mM L-Glutamine.
Cells were seeded at 4000 cells per well in 96 well plates in DMEM media containing 1% charcoal/dextran-treated FBS and 2 mM glutamine and allowed to settle for 4 hours prior to treatment with Compound (I) at concentrations ranging from 0-3 µM and 0-10 µg/ml respectively. Two hours following treatment, cells were incubated with 10 ng/ml HRG, a concentration required to increase MCF-7 cell proliferation to 90% of max ($ED_{90}$). Basal wells were unstimulated with ligand. After incubation for 4 days, cell viability was assessed using a 3-(4,5-dimethylthiazol-2-yl)-5-(3-carboxymethoxyphenyl)-2-(4-sulfophenyl)-2H-tetrazolium (MTS) assay.
Prior to $IC_{50}$ determination of HRG-stimulated compound-treated cells, mean basal growth at 96 hours was subtracted from each of the readouts so that proliferation driven through HRG-signalling was assessed. Basal $IC_{50}$ values are expressed as $GI_{50}$ i.e. the day 0 plate cell number (baseline reading) was subtracted from the readout at 96 hours later.
Results:
The results are summarised in Tables 4 and 5.

TABLE 4

HRG-stimulated proliferation $IC_{50}$ value

| Compound | Geo Mean $IC_{50}$ | 95% CIR |
|---|---|---|
| Compound (I) | 0.061 µM | 2.421 |

TABLE 5

Basal proliferation $GI_{50}$ values

| Compound | Geo Mean $GI_{50}$ | 95% CIR |
|---|---|---|
| Compound (I) | 1.094 µM | 4.423 |

In the KB cells, stimulation with EGF, which specifically binds to EGFR, causes phosphorylation and therefore activation of this receptor. Similarly in the MCF-7 cells HRG, which binds specifically to ErbB3 causes it to form heterodimers with ErbB2 and both receptors become phosphorylated and activated. Tables 4 shows that Compound (I) is a potent inhibitor of HRG-stimulated MCF-7 proliferation. These effects on proliferation are believed to be due to the activities of these compounds on ErbB2/ErbB3 heterodimers, with Compound (I) being a much more potent inhibitor of this heterodimer.

The MCF-7 basal assays represent a situation where there no increased stimulation or activation of erbB2/erbB3 heterodimerisation. Table 5 shows that even in such conditions Compound (I) inhibits MCF-7.

Example 1

Preparation of Compound (I) Difumarate Form A: 2-[4-({4-[(3-Chloro-2-fluorophenyl)amino]-7-methoxyquinazolin-6-yl}oxy)piperidin-1-yl]-N-methylacetamide di-[(2E)-but-2-enedioate] Form A A solution of fumaric acid (2.7 g, 23.22 mmol) in methanol (95 ml) was added to a mixture of 2-[4-({4-[(3-Chloro-2-fluorophenyl)amino]-7-methoxyquinazolin-6-yl}oxy)piperidin-1-yl]-N-methylacetamide (Compound (I)) (5.62 g at 89% w/w, 10.55 mmol) in isopropanol (100 ml) maintaining the temperature >65° C. The mixture was heated at reflux for one hour before clarification. The reaction mixture was cooled to 30° C. over 90 minutes and held for 30 minutes to establish crystallisation. The reaction was cooled to 0° C. over 2 hours and held for 1 hour before isolation by filtration. The filter cake was washed twice with cold isopropanol (2×10 ml) and dried in vacuo at 50° C. to give the title compound as a white solid (5.84 g, 78%); $^1$H NMR Spectrum: (DMSO) 1.85 (m, 1H), 2.08 (m, 1H), 2.50 (m, 1H), 2.66 (d, 3H), 2.83 (m, 1H), 3.05 (s, 2H), 3.96 (s, 3H), 4.58 (m, 1H), 6.64 (s, 4H), 7.23 (s, 1H), 7.28 (m, 1H), 7.46 (ddd, 1H), 7.55 (m, 1H), 7.70 (broad q, 1H), 7.85 (s, 1H), 8.38 (s, 1H).

Example 2

Preparation of Compound (I) Difumarate Form A: 2-[4-({4-[(3-Chloro-2-fluorophenyl)amino]-7-methoxyquinazolin-6-yl}oxy)piperidin-1-yl]-N-methylacetamide di-[(2E)-but-2-enedioate] Form A A solution of fumaric acid (1.4 kg, 12.1 mol) in methanol (26.6 kg) was added to a mixture of 2-[4-({4-[(3-chloro-2-fluorophenyl)amino]-7-methoxyquinazolin-6-yl}oxy)piperidin-1-yl]-N-methylacetamide (2.93 kg, 84.8% w/w, 5.24 mol) in isopropanol (39 kg) maintaining the temperature >65° C. A line wash of methanol (3.6 kg) was charged. The mixture was heated at reflux for one hour before clarification, followed by a line wash of methanol (7 kg). The reaction mixture was distilled at atmospheric pressure to remove 47 kg of distillates. Isopropanol (15.8 kg was added and the reaction mixture distilled to remove 15.6 kg of distillates. Crystallisation occurred during the distillation. Isopropanol (21 kg) was added and the reaction cooled to 0° C. over 8 hours and held for 1 hour before isolation by filtration. The filter cake was washed with cold 50:50 isopropanol:MeOH (4 kg) followed by cold isopropanol (4 kg) and dried in vacuo at 50° C. to give the title compound as a white solid (3.64 kg, 98%); $^1$H NMR Spectrum: (DMSO) 1.85 (m, 1H), 2.08 (m, 1H), 2.50 (m, 1H), 2.66 (d, 3H), 2.83 (m, 1H), 3.05 (s, 2H), 3.96 (s, 3H), 4.58 (m, 1H), 6.64 (s, 4H), 7.23 (s, 1H), 7.28 (m, 1H), 7.46 (ddd, 1H), 7.55 (m, 1H), 7.70 (broad q, 1H), 7.85 (s, 1H), 8.38 (s, 1H).

Example 3

Preparation of Compound (I) Difumarate Form A: 2-[4-({4-[(3-Chloro-2-fluorophenyl)amino]-7-methoxyquinazolin-6-yl}oxy)piperidin-1-yl]-N-methylacetamide di-[(2E)-but-2-enedioate] Form A 2-[4-({4-[(3-Chloro-2-fluorophenyl)amino]-7-methoxyquinazolin-6-yl}oxy)piperidin-1-yl]-N-methylacetamide (Compound (I)) (60.19 g at 88% w/w, 111.8 mmol) was dissolved in ethyl acetate (1550 ml). The solution was clarified by filtration and the filter washed with ethyl acetate (53 ml). The solution was cooled to 40° C. A clarified solution of fumaric acid (26.60 g, 257.0 mmol) in isopropanol (408 ml) was then added over 1 hour. The filter used to clarify the fumaric acid solution was then washed with isopropanol (37 ml). After holding for 1 hour at 40° C. the reaction was cooled to 20° C. over 1 hour. The reaction mixture was held for 13.5 hours before isolating the product by filtration. The filter cake was washed twice with ethyl acetate (82 ml): isopropanol (24 ml) and then dried in vacuo at 40° C. to give the title compound as a white solid (72.32 g, 90%); $^1$H NMR Spectrum: (DMSO) 1.85 (m, 1H), 2.08 (m, 1H), 2.50 (m, 1H), 2.66 (d, 3H), 2.83 (m, 1H), 3.05 (s, 2H), 3.96 (s, 3H), 4.58 (m, 1H), 6.64 (s, 4H), 7.23 (s, 1H), 7.28 (m, 1H), 7.46 (ddd, 1H), 7.55 (m, 1H), 7.70 (broad q, 1H), 7.85 (s, 1H), 8.38 (s, 1H).

Example 4

Preparation of Compound (I) Difumarate Form A: 2-[4-({4-[(3-Chloro-2-fluorophenyl)amino]-7-methoxyquinazolin-6-yl}oxy)piperidin-1-yl]-N-methylacetamide di-[(2E)-but-2-enedioate] Form A 2-[4-({4-[(3-Chloro-2-fluorophenyl)amino]-7-methoxyquinazolin-6-yl}oxy)piperidin-1-yl]-N-methylacetamide (Compound (I)) (2.75 g at assumed 100% w/w, 5.80 mmol) was dissolved in ethyl acetate (94 ml) and isopropanol (14 ml). The solution was distilled such that 25.2 ml of distillates were collected. The solution was cooled to 40° C. A clarified solution of fumaric acid (1.38 g, 11.90 mmol) in isopropanol (21 ml) was then added over 1 hour. Compound (I) difumarate Form A seed was added (3.7 mg, 5.3 µmol). The filter used to clarify the fumaric acid solution was then washed with isopropanol (2 ml). After holding for 1 hour at 40° C. the reaction was cooled to 20° C. over 2 hours. The reaction mixture was held for 15 hours before isolating the product by filtration. The filter cake was washed twice with ethyl acetate (4.3 ml): isopropanol (1.2 ml) and then dried in vacuo at 40° C. to give the title compound as a white solid (72.32 g, 90%); $^1$H NMR Spectrum: (DMSO) 1.85 (m, 1H), 2.08 (m, 1H), 2.50 (m, 1H), 2.66 (d, 3H), 2.83 (m, 1H), 3.05 (s, 2H), 3.96 (s, 3H), 4.58 (m, 1H), 6.64 (s, 4H), 7.23 (s, 1H), 7.28 (m, 1H), 7.46 (ddd, 1H), 7.55 (m, 1H), 7.70 (broad q, 1H), 7.85 (s, 1H), 8.38 (s, 1H).

Example 5

Preparation of Compound (I) Difumarate Form A: 2-[4-({4-[(3-Chloro-2-fluorophenyl)amino]-7-methoxyquinazolin-6-yl}oxy)piperidin-1-yl]-N-methylacetamide di-[(2E)-but-2-enedioate] Form A 2-[4-({4-[(3-Chloro-2-fluorophenyl)amino]-7-methoxyquinazolin-6-yl}oxy)piperidin-1-yl]-N-methylacetamide (Compound (I)) (1 g, 1.86 mmoles) and fumaric acid (0.44 g, 3.81 mmoles) were suspended in water (4.4 g) and heated to 85° C. The reaction mixture was cooled to 60° C. at 1° C./minute and Compound (I) Form A seed was added when the temperature was 77° C. The resulting solid was isolated by filtration, washed twice with acetone (0.70 g per wash) and dried in a vacuum oven at 40° C. to afford the title compound (0.89 g, 68% yield), 1H NMR (400 MHz, DMSO-d6) d ppm 1.84 (m, 2H) 2.08 (m, 2H) 2.55 (m, 2H) 2.63 (d, J=4.7 Hz, 3H) 2.86 (m, 2H) 3.12 (s, 2H) 3.93 (s, 3H) 4.59 (tt, J=7.8, 3.7 Hz, 1H) 6.62 (s, 4H) 7.21 (s, 1H) 7.27 (td, J=8.1, 1.3 Hz, 1H) 7.49 (m, 2H) 7.86 (m, 2H) 8.36 (s, 1H) 9.63 (br. s., 1H).

Compound (I) Difumarate Form A Properties

Figure 6:
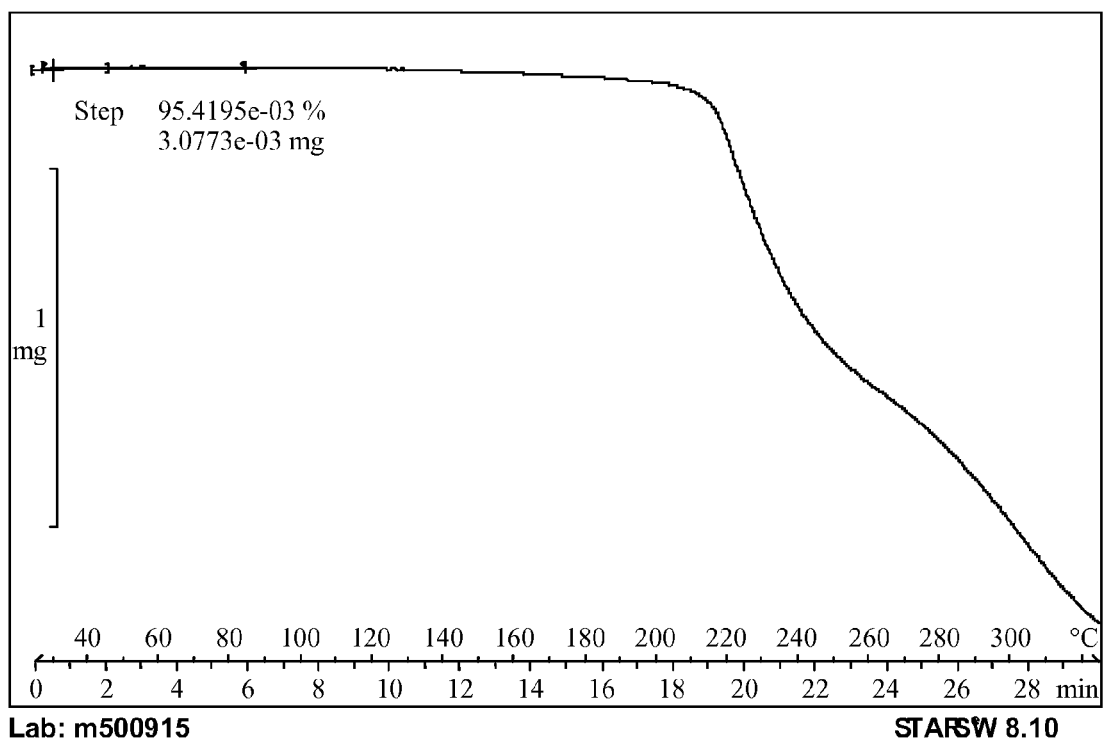
FIG. 6 shows a thermogravimetric trace for Compound (I) difumarate Form A. The x-axis shows temperature and time, the y-axis shows weight in mg. The text in this graph shows the % weight loss and absolute weight loss from the sample between about 30 and 80° C.
Figure 7:
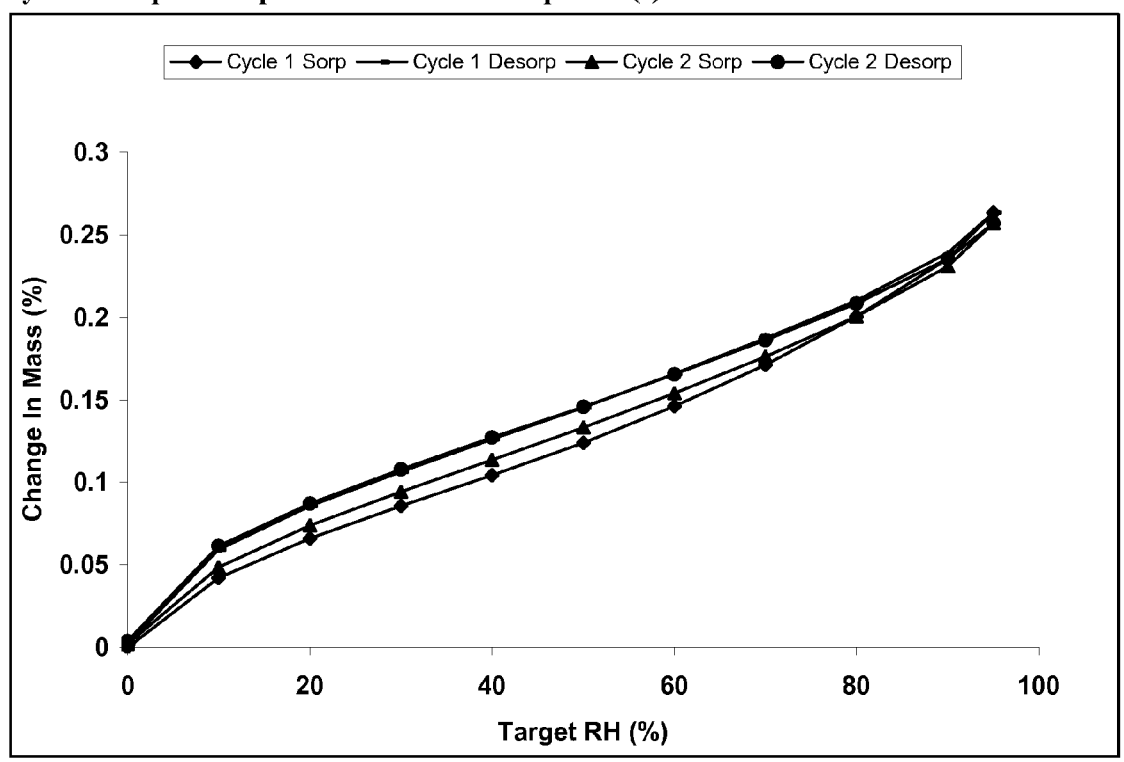
FIG. 7 shows a dynamic vapour sorption isotherm plot for Compound (I) difumarate Form A. The x-axis shows the % relative humidity, the y-axis shows the % change in mass of the sample. "sorp" refers to an adsorption cycle and "desorp" to a desorption cycle.

Compound (I) difumarate Form A is a free flowing powder. X-ray powder diffraction of Compound (I) difumarate (FIG. 4) indicates that the material is crystalline. The most prominent peaks from the XRPD pattern of Form A are described hereinbefore and listed in Table 1. Differential Scanning calorimetry shows a single melting endotherm with an onset at 210.4° C. (FIG. 5). No appreciable weight losses are observed by Thermogravimetric analysis (FIG. 6). Dynamic Vapour Sorption demonstrates the compound to be non-hygroscopic absorbing <0.5% moisture up to 95% relative humidity with no evidence of hysteresis (FIG. 7).

Comparison of Aqueous Solubility of Compound (I) and Compound (I) Difumarate Form A The solubility (48 hours, 25° C.) of Compound (I) in a range of aqueous buffers is detailed in Table 4. Compound (I) exhibits pH dependent solubility in aqueous buffers with high solubility at low pH (27.2 mg/ml, pH 2.7) and low solubility at high pH (1 µg/ml, pH 7.9). Significant increases in solubility of Compound (I) occur at pH 6 and below. Therefore, at low pH values the dissolution rate of Compound (I) would be anticipated to be fast whereas at pH above 6 dissolution rates would be anticipated to be slow.

The solubility (48 hours, 25° C.) of Compound (I) in water is 1 µg/ml (pH 7.0). In comparison, the solubility of Compound (I) difumarate Form A in water (48 hours) is 22.5 mg/ml (pH 3.5). The intrinsic dissolution rates of Compound (I) difumarate Form A and Compound (I) was also been measured in a range of aqueous buffers. Compound (I) difumarate Form A has a significantly higher intrinsic dissolution rate in pH 6.5 phosphate buffer as shown in Table 6.

TABLE 6

Intrinsic Dissolution Rate of Compound (I) and Compound (I) difumarate Form A in aqueous buffers at 37° C.

| Compound | Intrinsic Dissolution Rate (mgmin$^{-1}$cm$^{-2}$)[1] | |
|---|---|---|
| | pH 6.5 | SGF |
| Compound (I) | 0.01 | 19.2 |
| Compound (I) difumarate Form A | 2.51 | 15.9 |

[1]Measured using fibre-optic probe, λ = 335 nm, disc size 4 mm, temp 37° C.
SGF = Simulated Gastric Fluid Pharmacokinetic Studies in Dogs to Comparing Compound (I) and Compound (I) Difumarate Form A Both compounds were dosed to dogs as direct compression tablets containing 100 mg Compound (I) free base, or the equivalent thereof for the tablets containing the di-fumarate salt) with the following composition:

25% w/w Compound (I) (or equivalent thereof of the difumarate salt);
10% w/w microcrystalline cellulose (Avicel 102);
4% w/w croscarmellose sodium (AcDiSol);

1% w/w sodium lauryl sulfate;
Lactose to 99% w/w
Magnesium Stearate to 100% w/w.
Per tablet this equated to:
151 mg Compound (I);
60.4 mg Avicel;
24.16 mg AcDiSol;
6.04 mg sodium lauryl sulfate;
356.36 mg Lactose; and
6.04 mg Magnesium Stearate.
Total tablet weight was 604 mg.

The performance of the solid dosage forms was evaluated in vitro prior to the in-vivo dog study commencing. Dissolution of solid dosage forms in pH 4.5 media (closest to sink conditions), at 100 mg (free base equivalents) Compound (I) loading, showed >90% release after 45 minutes (Table 7) indicating the suitability of these dosage forms for use in the dog PK study.

TABLE 7

% Dissolution of Compound (I) and Compound (I) Difumarate Form A in pH 4.5 citrate buffer.

| Compound | % Dissolution at 45 minutes |
|---|---|
| Compound (I) | 93.6 |
| Compound (I) difumarate Form A | 100.3 |

The performance of the tablet compositions administered orally to the dogs was compared to an intravenous injection of a 20 mg dose of compound (I) comprising 4 mg.mL$^{-1}$ dissolved and made up to volume with 25% w/v hydroxypropyl-beta-cyclodextrin (HP-beta-CD) in water for injection pH adjusted to 4 using 1M HCl.

The results of the dog study are shown in Table 8.

TABLE 8

Summary of Pharmacokinetic Parameters for Compound (I) and Compound (I) difumarate Form A administered orally and Compound (I) administered intravenously in Male Beagle Dogs (n = 4, mean ± SE)

| | Study 0383KD - Compound (I) Formulation/Route (Dose) | | |
|---|---|---|---|
| Parameter | IV (20 mg) | Free form[1] (100 mg) | Difumarate Form A[1] (equivalent to 100 mg free form) |
| $C_{max}$ (µmol/L) | 9.0 ± 1.1 | 14.0 ± 1.7 | 32.6 ± 3.6 |
| $T_{max}$ (h) | 0.2 ± 0.0 | 1.6 ± 0.8 | 1.1 ± 0.3 |
| Half-life (h) | 5.3 ± 0.2 | 8.2 ± 0.6 | 16.9 ± 4.0 |
| $AUC_{(0-48)}$ (µmol · h/L) | 33.4 ± 7.7 | 103.9 ± 25.3 | 190.3 ± 46.9 |
| Cl (ml/min/kg) | 1.9 ± 0.5 | — | — |
| Hbf (ml/min) | 39 | — | — |
| Vss (L/kg) | 0.6 ± 0.1 | — | — |
| Bioavailability$_{(0-48 h)}$ (%) | — | 63.5 ± 7.0 | 112.5 ± 8.1 |

[1]dosed as direct compressed tablet;
$C_{max}$ = Peak plasma concentration
$T_{max}$ = Time to maximum plasma concentration.
AUC = Area under curve
Cl = Clearance
Hbf = Hepatic blood flow
Vss = Volume of distribution at steady state Table 8 shows that bioavailability and peak plasma concentration ($C_{max}$) of Compound (I) difumarate Form A are significantly better than those obtained for Compound (I) (113% compared to 64% bioavailability) as determined in a paired t-test (n=4) at a 95% confidence level.

Examples 6 to 21 Crystalline Compound (I) Difumarate Forms B to Q

XRPD Analysis

XRPD patterns were collected using a Bruker D-8 Discover diffractometer and Bruker's General Detector System (GADDS, v. 4.1.20). An incident microbeam of Cu Kα radiation was produced using a fine-focus tube (40 kV, 40 mA), a Göbel mirror, and a 0.5 mm double-pinhole collimator. Prior to the analysis, a silicon standard (NIST SRM 640c) was analysed to verify the Si 111 peak position. The sample was packed between 3 µm thick films to form a portable, disc-shaped specimen. The prepared specimen was loaded in a holder secured to a translation stage. A video camera and laser were used to position the area of interest to intersect the incident beam in transmission geometry. The incident beam was scanned and rastered to optimize orientation statistics. A beam-stop was used to minimize air scatter from the incident beam. Diffraction patterns were collected using a Hi-Star area detector located 15 cm from the sample and processed using GADDS. The intensity in the GADDS image of the diffraction pattern was integrated using a step size of 0.04° 2θ. The integrated patterns display diffraction intensity as a function of 2θ.

Variable Temperature—XRPD

Variable-temperature XRPD patterns (VT-XRPD) were collected using a Shimadzu XRD-6000 X-ray powder diffractometer equipped with an Anton Paar HTK 1200 high-temperature stage. Prior to the analysis, a silicon standard (NIST SRM 640c) was analysed to verify the Si 111 peak position, and vanillin and sulfapyridine standards were analysed to verify the stage temperature. The sample was packed in a ceramic holder and analysed from 2.5 to 40° 2θ at 3°/minute (0.4 sec/0.02° step).

XRPD—Microplate Analysis

XRPD patterns were collected with a Bruker D-8 Discover diffractometer and Bruker's General Area Diffraction Detection System (GADDS, v. 4.1.20). An incident beam of Cu Kα radiation was produced using a fine-focus tube (40 kV, 40 mA), a Gael mirror, and a 0.5 mm double-pinhole collimator. The samples were positioned for analysis by securing the well plate to a translation stage and moving each sample to intersect the incident beam. The samples were analysed using a transmission geometry. The incident beam was scanned and rastered over the sample during the analysis to optimize orientation statistics. A beam-stop was used to minimize air scatter from the incident beam at low angles. Diffraction patterns were collected using a Hi-Star area detector located 15 cm from the sample and processed using GADDS. The intensity in the GADDS image of the diffraction pattern was integrated using a step size of 0.04° 2θ. The integrated patterns display diffraction intensity as a function of 2θ. Prior to the analysis a silicon standard was analysed to verify the Si 111 peak position.

Example 6

Preparation of Compound (I) Difumarate Form B

A slurry was prepared by adding enough Compound (I) difumarate Form A to water so that excess solid was present. The mixture was then agitated in a sealed vial at 4° C. for 7 days. Solids were isolated by vacuum filtration and analysed.

Figure 8:
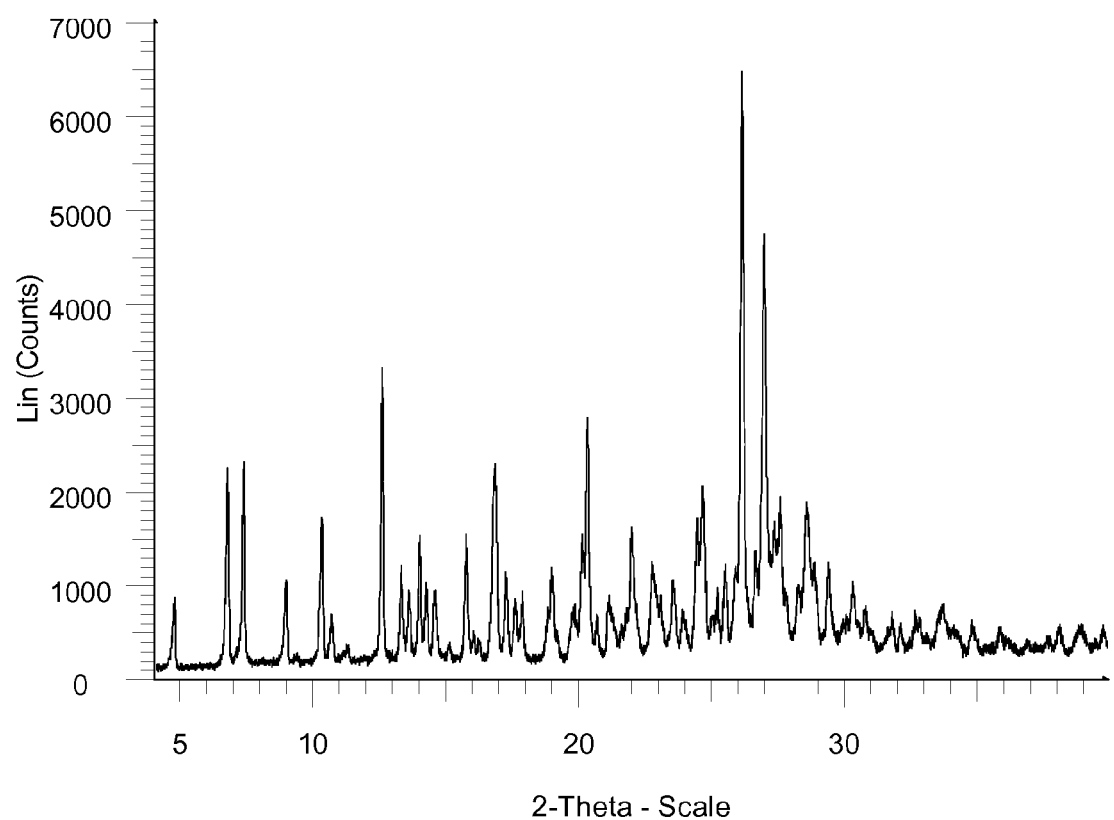
FIG. 8 shows an X-ray powder diffraction pattern for Compound (I) difumarate Form B. The x-axis shows the 2-theta value and the y-axis the counts.

The XRPD pattern for the resulting Form B is shown in FIG. 8. The most prominent X-Ray Powder Diffraction peaks for Form B are shown in Table 9:

TABLE 9

| Angle 2-Theta ° | Intensity Count |
| --- | --- |
| 4.7 | 362 |
| 6.8 | 984 |
| 7.4 | 977 |
| 9.0 | 457 |
| 10.3 | 751 |
| 12.6 | 1446 |
| 13.3 | 473 |
| 13.6 | 375 |
| 14.0 | 656 |
| 14.3 | 414 |
| 14.6 | 377 |
| 15.8 | 579 |
| 16.8 | 963 |
| 17.3 | 454 |
| 17.6 | 352 |
| 17.9 | 338 |
| 19.0 | 519 |
| 20.1 | 672 |
| 20.3 | 1165 |
| 21.1 | 388 |
| 22.0 | 704 |
| 22.1 | 561 |
| 22.8 | 531 |
| 23.1 | 355 |
| 23.6 | 459 |
| 24.5 | 694 |
| 24.7 | 870 |
| 25.2 | 388 |
| 25.5 | 530 |
| 25.9 | 497 |
| 26.2 | 2683 |
| 26.7 | 593 |
| 27.0 | 2034 |
| 27.4 | 697 |
| 27.6 | 788 |
| 27.8 | 374 |
| 28.3 | 419 |
| 28.6 | 792 |
| 28.7 | 721 |
| 28.9 | 510 |
| 29.4 | 538 |
| 30.4 | 407 |

Form B is thought to be a hydrate, possibly a tetra or penta hydrate.

Example 7

Preparation of Compound (I) Difumarate Form C

Figure 9:
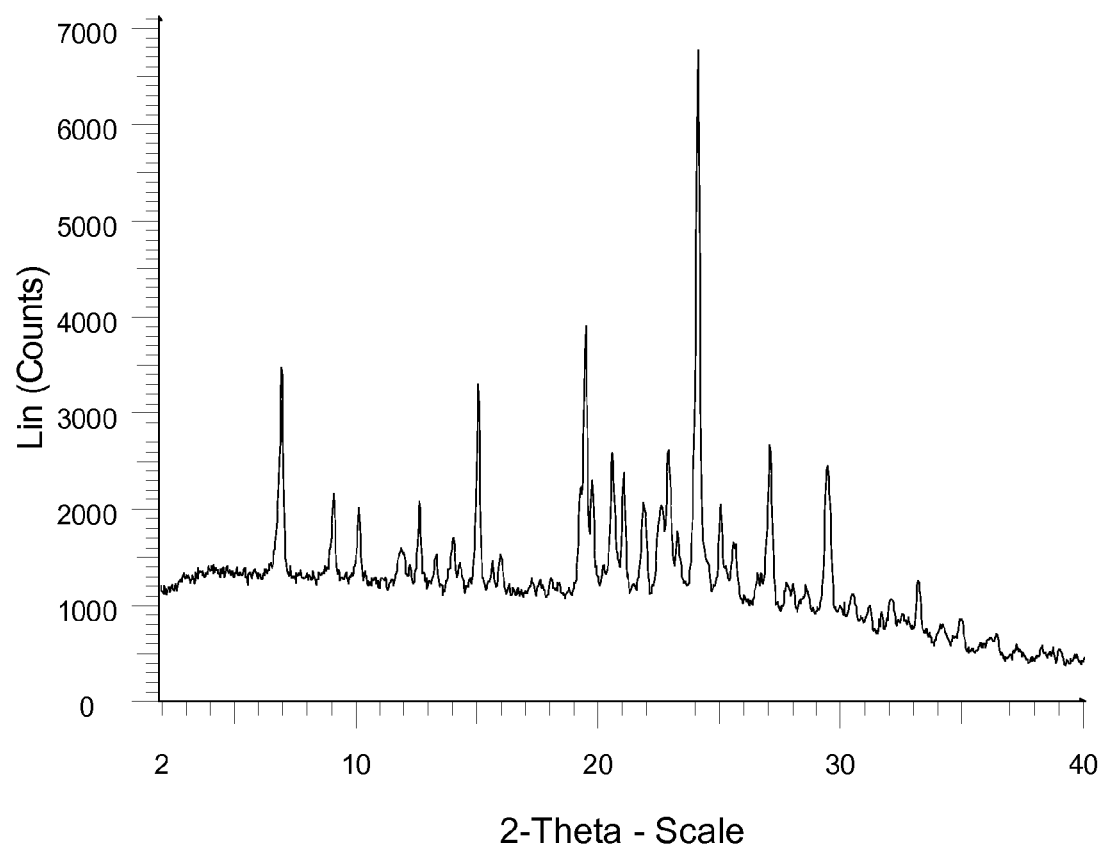
FIG. 9 shows an X-ray powder diffraction pattern for Compound (I) difumarate Form C. The x-axis shows the 2-theta value and the y-axis the counts.

A slurry was prepared by adding enough Compound (I) difumarate Form A to IPA/water (90/10 v/v), so that excess solid was present. The mixture was then agitated in a sealed vial at 15° C. for 6 days. Solids were isolated by vacuum filtration and analysed. The XRPD pattern for the resulting Form C is shown in FIG. 9. The most prominent X-Ray Powder Diffraction peaks for Form C are shown in Table 10:

TABLE 10

| Angle 2-Theta ° | Intensity Count |
| --- | --- |
| 3.5 | 1014 |
| 5.3 | 1016 |
| 6.9 | 3144 |
| 9.1 | 1820 |

TABLE 10-continued

| Angle 2-Theta ° | Intensity Count |
| --- | --- |
| 10.1 | 1648 |
| 10.7 | 919 |
| 11.1 | 917 |
| 11.9 | 1221 |
| 12.6 | 1733 |
| 13.3 | 1185 |
| 14.0 | 1316 |
| 14.3 | 1081 |
| 15.0 | 2958 |
| 15.6 | 1009 |
| 16.0 | 1161 |
| 17.3 | 886 |
| 17.6 | 897 |
| 18.1 | 941 |
| 18.3 | 871 |
| 19.2 | 1791 |
| 19.5 | 3574 |
| 19.7 | 1957 |
| 20.2 | 1066 |
| 20.6 | 2120 |
| 21.0 | 2043 |
| 21.9 | 1661 |
| 22.6 | 1643 |
| 22.9 | 2277 |
| 23.3 | 1424 |
| 24.1 | 6452 |
| 24.5 | 1094 |
| 25.1 | 1701 |
| 25.6 | 1249 |
| 26.7 | 917 |
| 27.1 | 2265 |
| 27.8 | 884 |
| 28.0 | 874 |
| 28.6 | 826 |
| 29.5 | 2106 |
| 33.2 | 912 |

Form C is believed to be a mixed hydrate/solvate form.

Example 8

Preparation of Compound (I) Difumarate Form D

Figure 10:
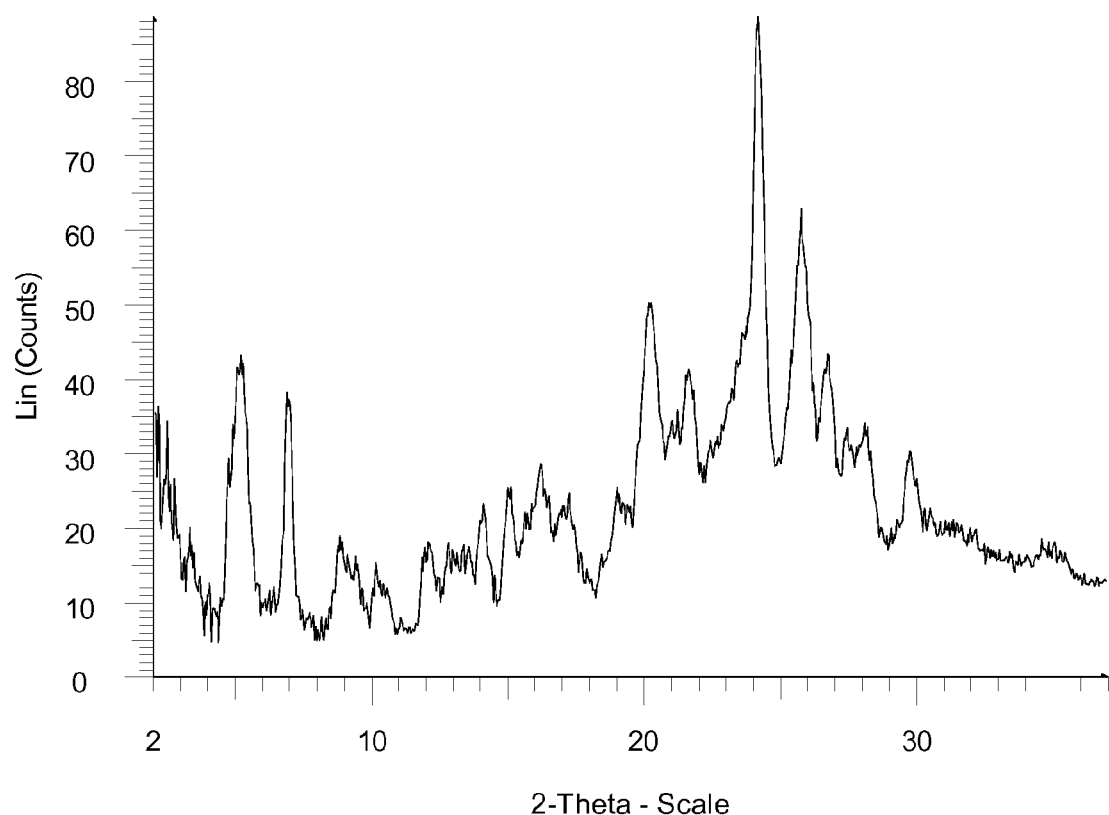
FIG. 10 shows an X-ray powder diffraction pattern for Compound (I) difumarate Form D. The x-axis shows the 2-theta value and the y-axis the counts.

A solution of Compound (I) difumarate was prepared in acetonitrile/water 50/50 and an aliquot was added to a microplate well. The solvent was evaporated and 2-propanol/water (90/10, v/v) was added to the well. The plate was sonicated and then the to solvent was evaporated under vacuum. The XRPD pattern for the resulting Form D is shown in FIG. 10. The most prominent X-Ray Powder Diffraction peaks for Form D are shown in Table 11:

TABLE 11

| Angle 2-Theta ° | Intensity Count |
| --- | --- |
| 3.3 | 14.1 |
| 5.1 | 39.1 |
| 6.9 | 35 |
| 8.8 | 14.9 |
| 10.2 | 10.5 |
| 12.0 | 13.6 |
| 14.0 | 18.9 |
| 15.0 | 22.5 |
| 16.2 | 26.3 |
| 17.1 | 19.1 |
| 19.0 | 21.4 |
| 20.2 | 47.6 |
| 21.6 | 39.2 |
| 24.2 | 85.2 |
| 25.8 | 61 |

TABLE 11-continued

| Angle 2-Theta ° | Intensity Count |
|---|---|
| 26.7 | 39.6 |
| 28.1 | 30.3 |
| 29.8 | 28.1 |

Example 9

Preparation of Compound (I) Difumarate Form E

Figure 11:
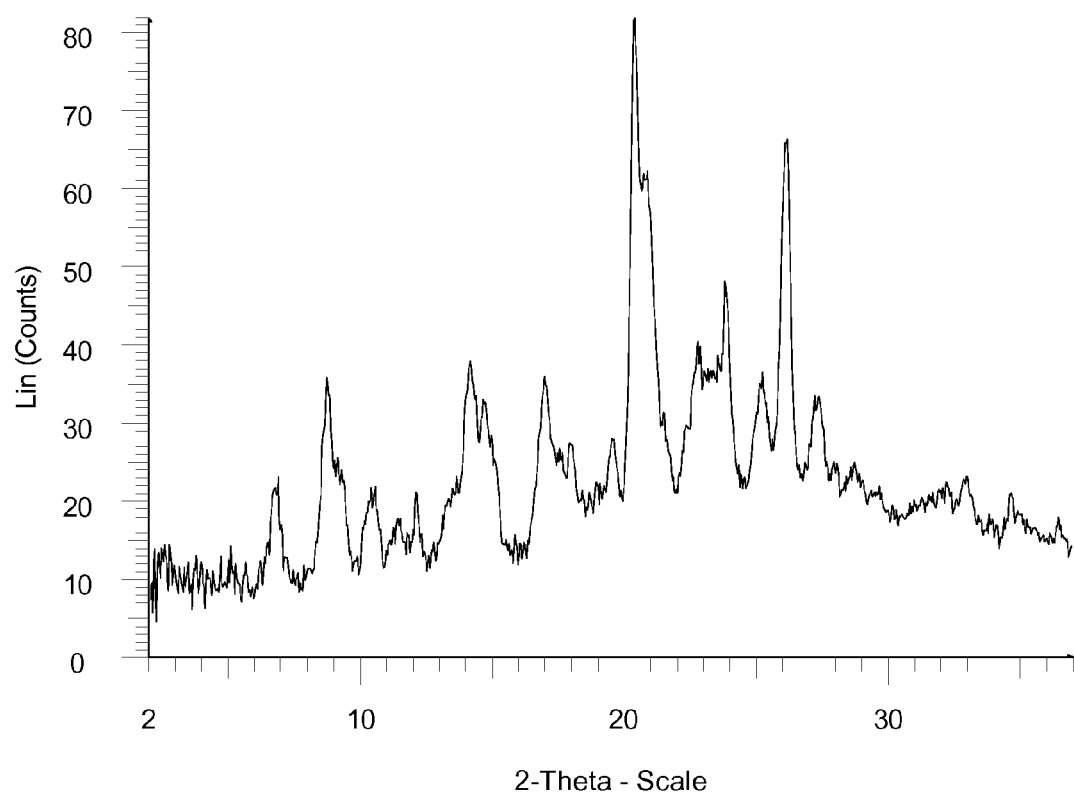
FIG. 11 shows an X-ray powder diffraction pattern for Compound (I) difumarate Form E. The x-axis shows the 2-theta value and the y-axis the counts.

A solution of Compound (I) Difumarate was prepared in acetonitrile/water 50/50 (v/v) and an aliquot was added to a microplate well. The solvent was evaporated and tetrahydrofuran was added to the well. The plate was sonicated and then the solvent was evaporated under vacuum. The XRPD pattern for the resulting Form E is shown in FIG. 11. The most prominent X-Ray Powder Diffraction peaks for Form E are shown in Table 12:

TABLE 12

| Angle 2-Theta ° | Intensity Count |
|---|---|
| 5 | 1.12 |
| 6.7 | 13.3 |
| 8.7 | 26.7 |
| 10.4 | 13.3 |
| 14.2 | 28.7 |
| 17.0 | 26.4 |
| 20.5 | 61.5 |
| 22.9 | 31.4 |
| 23.8 | 39.8 |
| 25.2 | 26 |
| 26.1 | 57.5 |
| 27.3 | 23.2 |

Example 10

Preparation of Compound (I) Difumarate Form F

Figure 12:
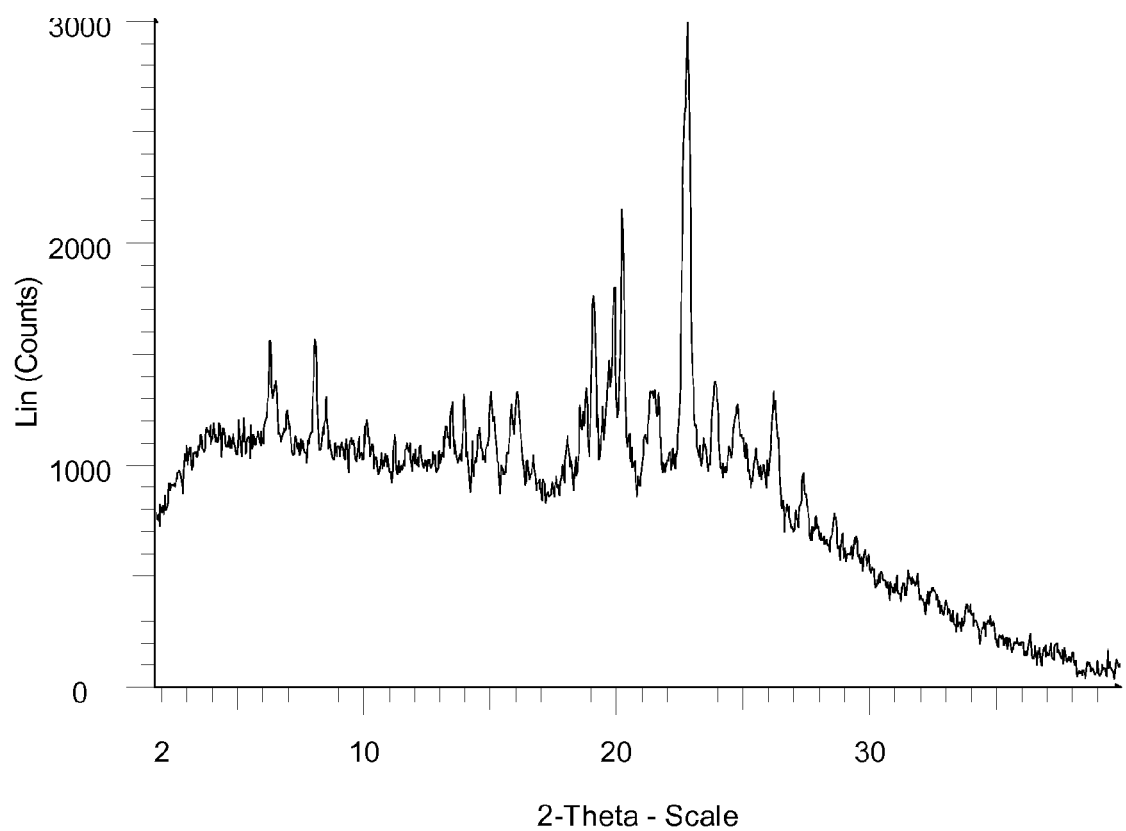
FIG. 12 shows an X-ray powder diffraction pattern for Compound (I) difumarate Form F. The x-axis shows the 2-theta value and the y-axis the counts.

A saturated solution of Compound (I) difumarate was prepared in tetrahydrofuran at elevated temperature and filtered through a 0.2 µm nylon filter into a pre-warmed vials while still warm. The vials were covered and allowed to cool slowly to room temperature. The presence or absence of solids was noted. If there were no solids present, or if the amount of solids was judged too small for XRPD analysis, the vial was placed in a refrigerator. Again, the presence or absence of solids was noted and if there were none, the vial was placed in a freezer. Solids that formed were isolated by filtration and allowed to dry prior to analysis. The XRPD pattern for the resulting Form F is shown in FIG. 12. The most prominent X-Ray Powder Diffraction peaks for Form F are shown in Table 13.

TABLE 13

| Angle 2-Theta ° | Intensity Count |
|---|---|
| 6.3 | 1491 |
| 8.0 | 1591 |
| 13.5 | 1764 |
| 13.9 | 1759 |
| 15.0 | 1349 |

TABLE 13-continued

| Angle 2-Theta ° | Intensity Count |
|---|---|
| 16.0 | 1301 |
| 19.1 | 1743 |
| 20.1 | 1547 |
| 21.5 | 1327 |
| 22.8 | 2683 |
| 23.9 | 1397 |
| 24.8 | 1295 |
| 26.2 | 1276 |
| 27.4 | 970 |

Example 11

Preparation of Compound (I) Difumarate Form G

Figure 13:
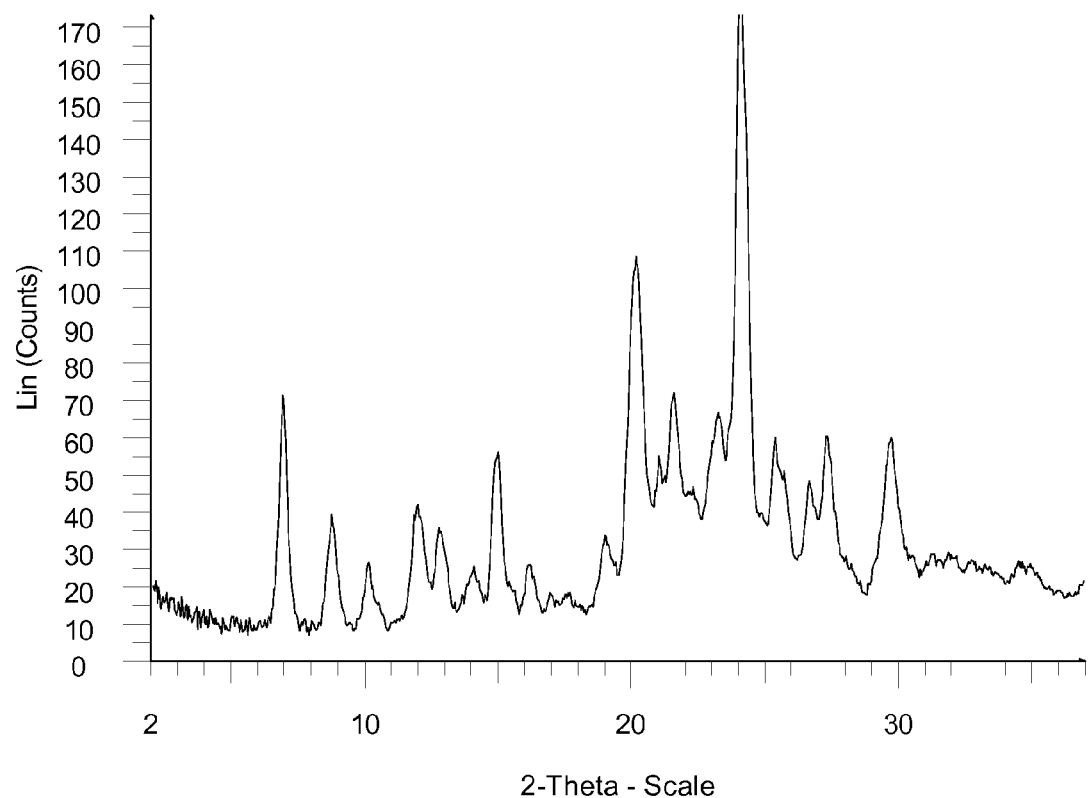
FIG. 13 shows an X-ray powder diffraction pattern for Compound (I) difumarate Form G. The x-axis shows the 2-theta value and the y-axis the counts.

A solution of Compound (I) difumarate was prepared in acetonitrile/water 50/50 and an aliquot was added to a microplate well. The solvent was evaporated and 2-propanol/water 90/10, was added to the well. The plate was sonicated and then the solvent was evaporated under vacuum. The XRPD pattern for the resulting Form G is shown in FIG. 13. The most prominent X-Ray Powder Diffraction peaks for Form G are shown in Table 14.

TABLE 14

| Angle 2-Theta ° | Intensity Count |
|---|---|
| 6.9 | 919 |
| 8.7 | 446 |
| 10.1 | 259 |
| 12.0 | 488 |
| 12.8 | 394 |
| 14.0 | 223 |
| 14.9 | 695 |
| 16.2 | 244 |
| 19.0 | 366 |
| 20.2 | 1461 |
| 21.6 | 925 |
| 23.2 | 848 |
| 24.1 | 2532 |
| 25.4 | 753 |
| 26.7 | 579 |
| 27.4 | 756 |
| 29.7 | 749 |

Example 12

Preparation of Compound (I) Difumarate Form H

Figure 14:
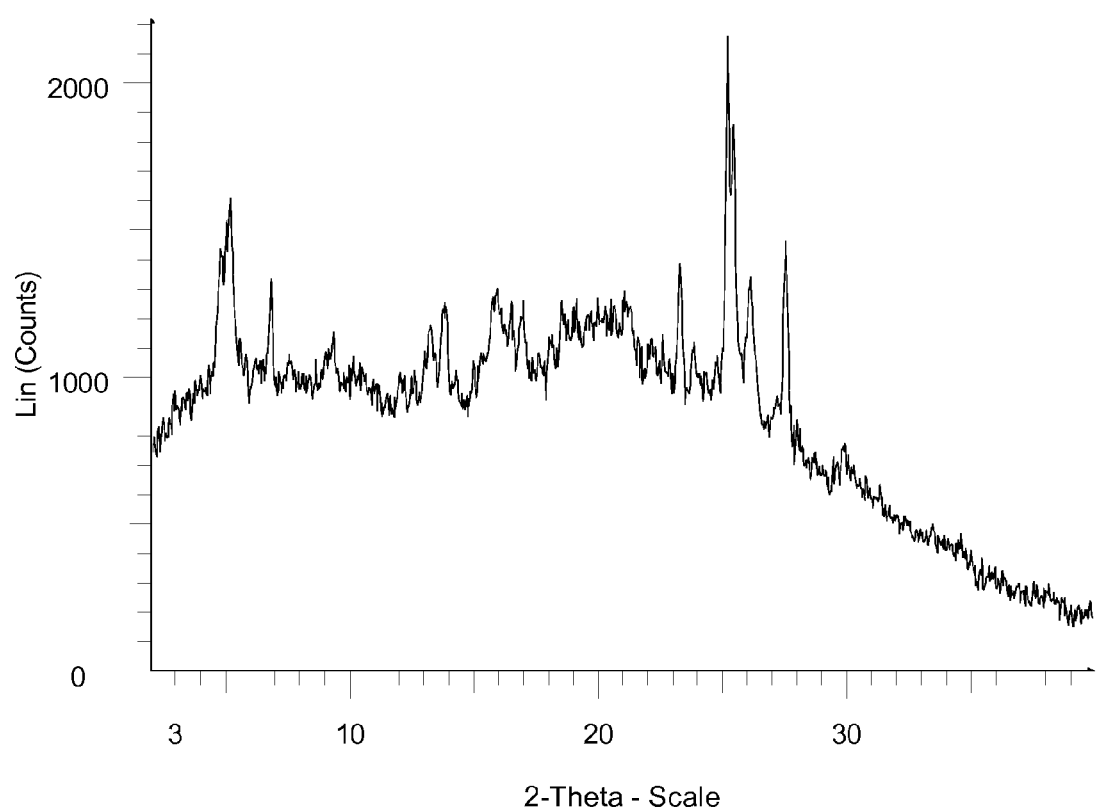
FIG. 14 shows an X-ray powder diffraction pattern for Compound (I) difumarate Form H. The x-axis shows the 2-theta value and the y-axis the counts.

A solution of Compound (I) difumarate was prepared in acetone/water (95/5, v/v), and sonicated between aliquot additions to assist in dissolution. Once the mixture reached complete dissolution, as judged by visual observation, the solution was filtered through a 0.2 µm nylon filter. The filtered solution was allowed to evaporate under ambient conditions in an uncapped vial. The solids that formed were isolated and analysed. The XRPD pattern for the resulting Form H is shown in FIG. 14. The most prominent X-Ray Powder Diffraction peaks for Form H are shown in Table 15:

TABLE 15

| Angle 2-Theta ° | Intensity Count |
| --- | --- |
| 4.8 | 1837 |
| 5.2 | 2010 |
| 6.8 | 1639 |
| 13.2 | 1563 |
| 13.8 | 1603 |
| 15.8 | 1625 |
| 16.5 | 1658 |
| 16.9 | 1603 |
| 23.3 | 1786 |
| 25.2 | 2564 |
| 25.4 | 2231 |
| 26.1 | 1698 |
| 27.6 | 1864 |

Example 13

Preparation of Compound (I) Difumarate Form I

Figure 15:
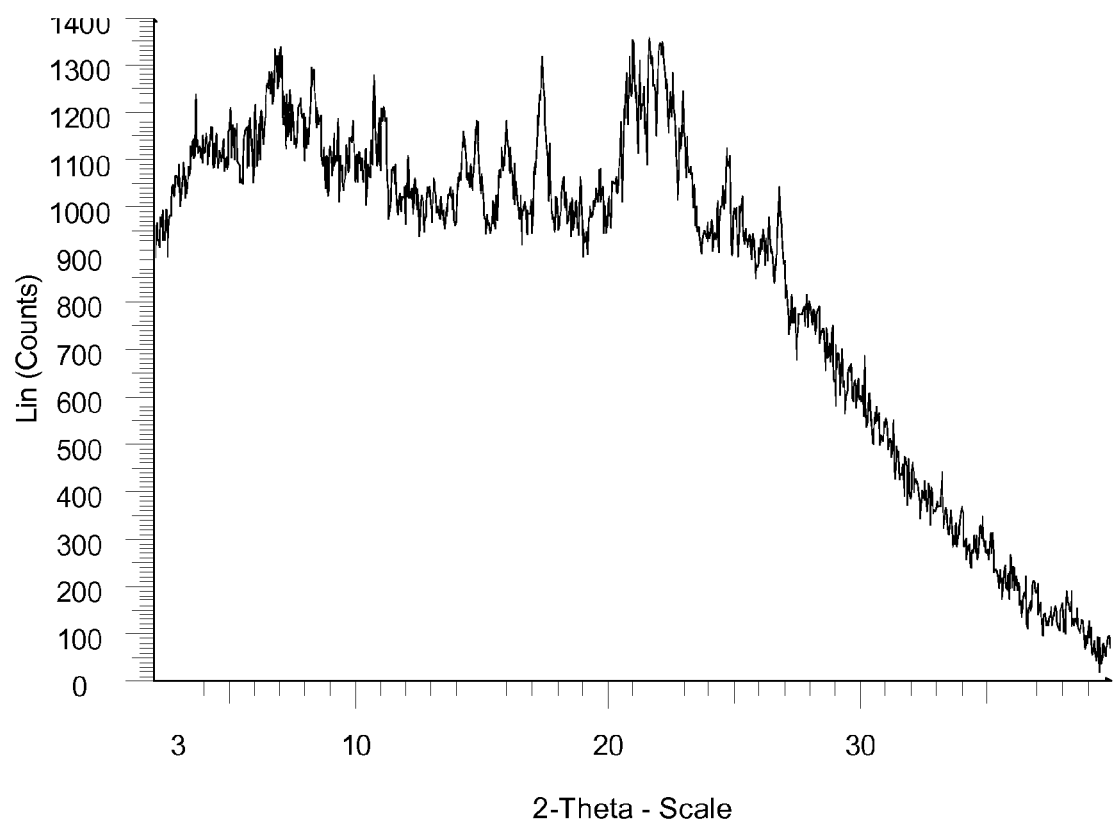
FIG. 15 shows an X-ray powder diffraction pattern for Compound (I) difumarate Form I. The x-axis shows the 2-theta value and the y-axis the counts.

A solution of Compound (I) difumarate was prepared in methanol at ambient temperature. The solution was then filtered into toluene at ambient temperature. The resulting solid was isolated by filtration and dried prior to analysis. The XRPD pattern for the resulting Form I is shown in FIG. 15. The most prominent X-Ray Powder Diffraction peaks for Form I are shown in Table 16:

TABLE 16

| Angle 2-Theta ° | Intensity Count |
| --- | --- |
| 10.7 | 2170 |
| 11.1 | 1793 |
| 14.3 | 1728 |
| 14.8 | 2080 |
| 16.0 | 2165 |
| 17.4 | 1868 |
| 21.7 | 1947 |
| 22.1 | 2130 |
| 24.8 | 1688 |
| 26.8 | 1643 |

Example 14

Preparation of Compound (I) Difumarate Form J

Figure 16:
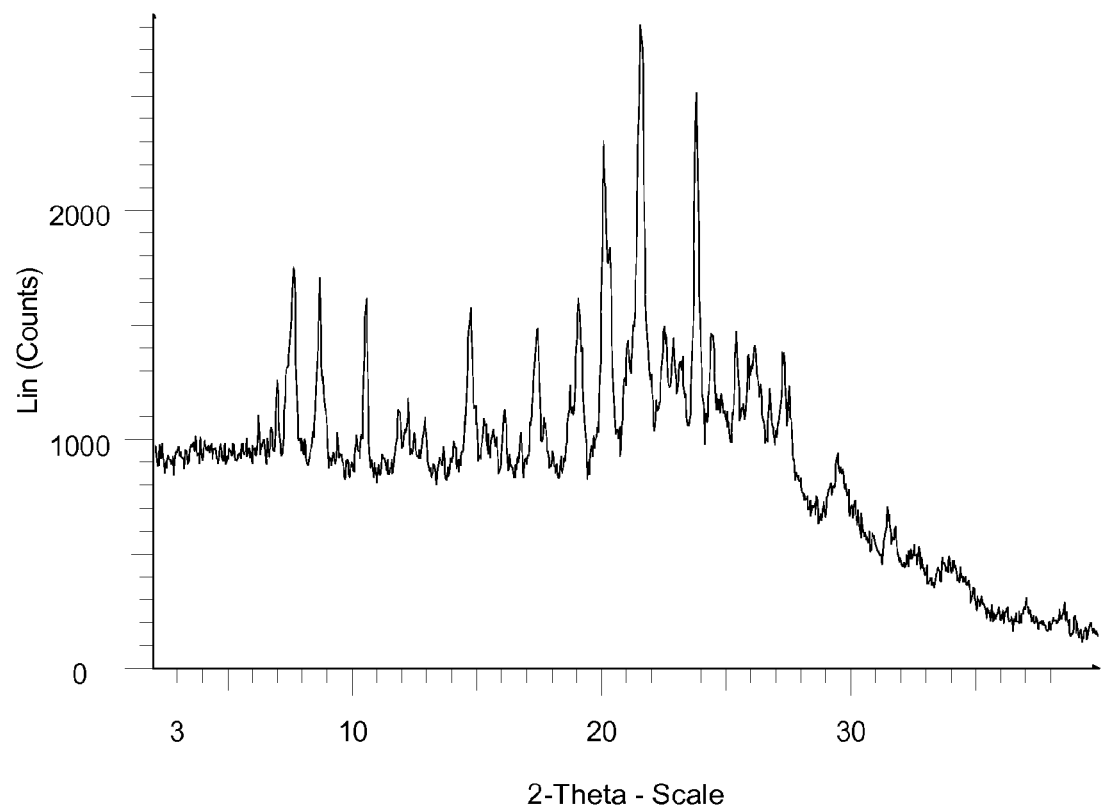
FIG. 16 shows an X-ray powder diffraction pattern for Compound (I) difumarate Form J. The x-axis shows the 2-theta value and the y-axis the counts.

A solution of Compound (I) difumarate was prepared in methanol at ambient temperature. The solution was then filtered into an excess of heptane at ambient temperature. The resulting solid was isolated by filtration and dried prior to analysis. The XRPD pattern for the resulting Form J is shown in FIG. 16. The most prominent X-Ray Powder Diffraction peaks for Form J are shown in Table 17:

TABLE 17

| Angle 2-Theta ° | Intensity Count |
| --- | --- |
| 7.0 | 1804 |
| 7.6 | 2353 |
| 8.7 | 2306 |
| 10.5 | 2129 |
| 11.9 | 1719 |
| 12.2 | 1802 |
| 12.9 | 1696 |
| 14.7 | 2171 |
| 16.1 | 1728 |
| 17.4 | 2079 |
| 19.1 | 2165 |
| 20.1 | 2723 |
| 21.6 | 3417 |
| 22.5 | 2094 |
| 23.8 | 3119 |
| 24.4 | 2048 |
| 25.4 | 2041 |
| 27.3 | 1978 |
| 29.5 | 1501 |

Example 15

Preparation of Compound (I) Difumarate Form K

Figure 17:
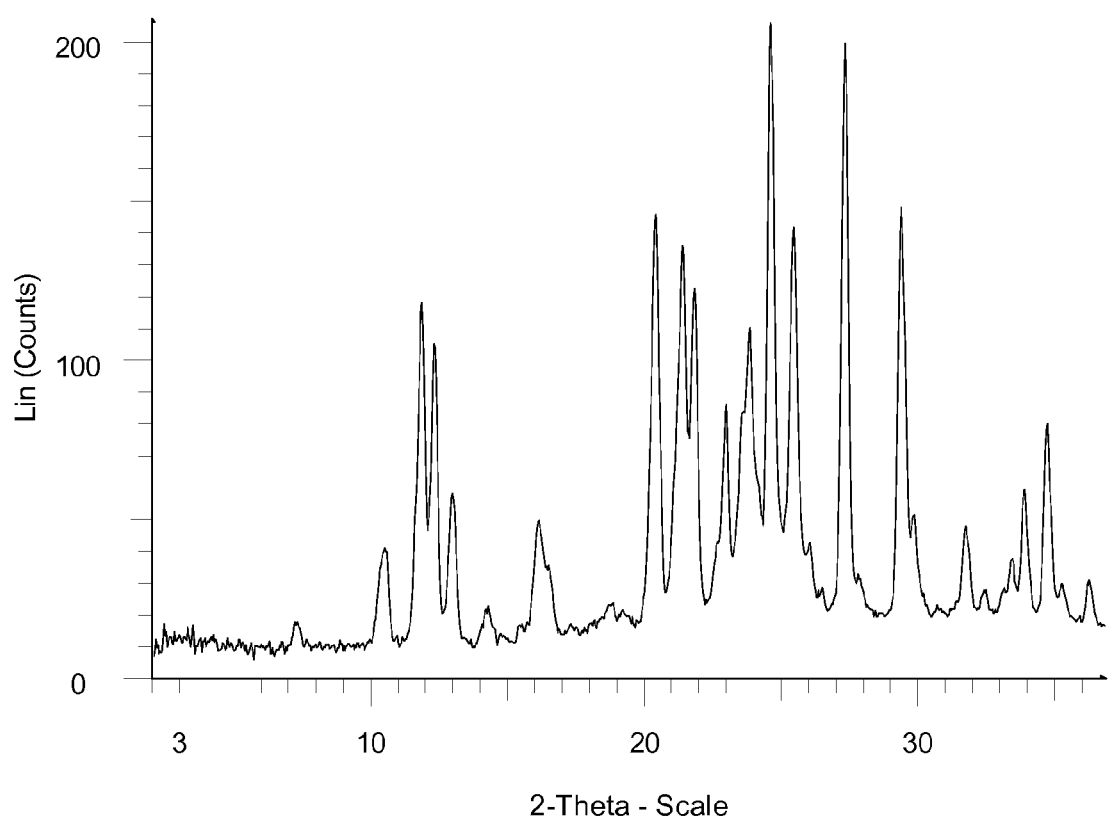
FIG. 17 shows an X-ray powder diffraction pattern for Compound (I) difumarate Form K. The x-axis shows the 2-theta value and the y-axis the counts.

A solution of Compound (I) difumarate was prepared in acetonitrile/water (50/50 v/v) and an aliquot was added to a microplate well. The solvent was evaporated and fluorobenzene was added to the well. The plate was sonicated and then the solvent was evaporated under ambient conditions. The XRPD pattern for the resulting Form K is shown in FIG. 17. The most prominent X-Ray Powder Diffraction peaks for Form K are shown in Table 18:

TABLE 18

| Angle 2-Theta ° | Intensity Count |
| --- | --- |
| 10.5 | 32.3 |
| 11.8 | 109 |
| 12.3 | 96.7 |
| 13.0 | 49.4 |
| 14.2 | 11.8 |
| 16.1 | 41 |
| 20.4 | 137 |
| 21.4 | 128 |
| 21.8 | 112 |
| 23.0 | 76.3 |
| 23.9 | 101 |
| 24.6 | 198 |
| 25.5 | 133 |
| 27.4 | 191 |
| 29.4 | 140 |
| 31.8 | 39.3 |
| 33.9 | 50.6 |
| 34.8 | 69.6 |

Example 16

Preparation of Compound (I) Difumarate Form L

Figure 18:
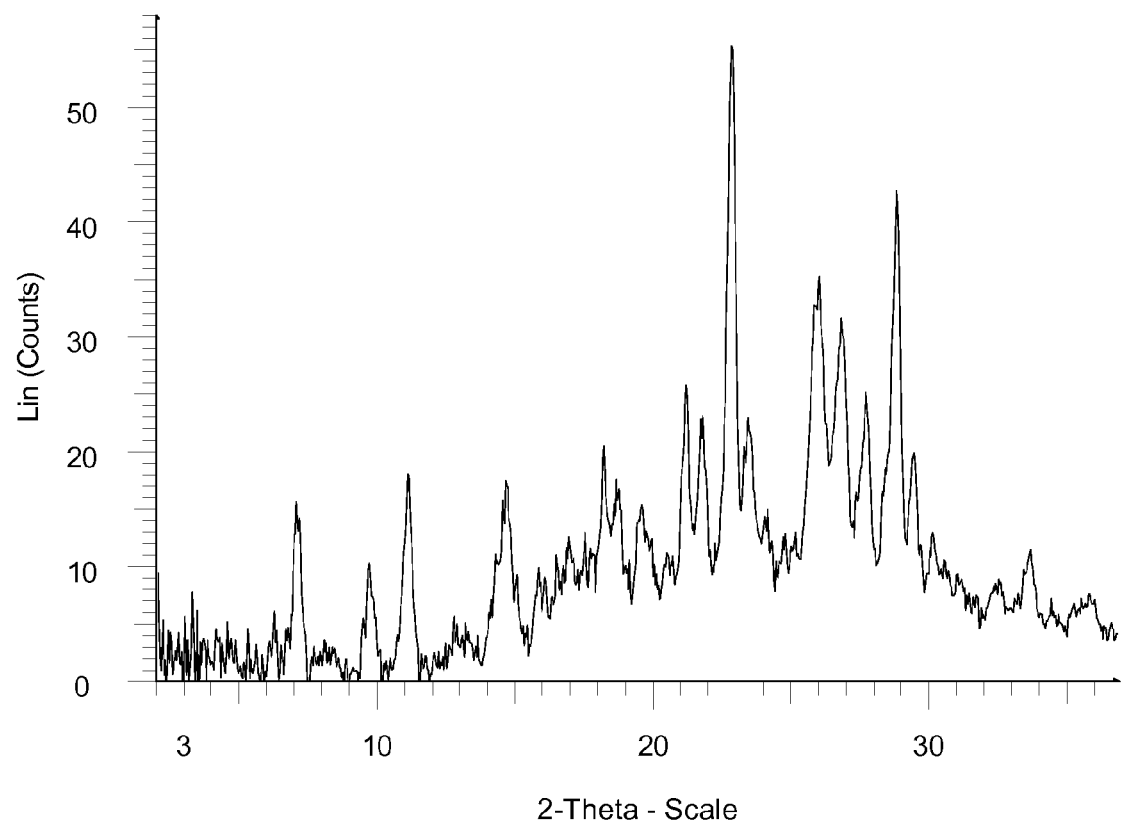
FIG. 18 shows an X-ray powder diffraction pattern for Compound (I) difumarate Form L. The x-axis shows the 2-theta value and the y-axis the counts.

A solution of Compound (I) difumarate was prepared in acetonitrile/water 50/50 (v/v) and an aliquot was added to a microplate well. The solvent was evaporated and 1,1,1,3,3,3 hexafluoro-2-propanol was added to the well. The plate was sonicated and then the solvent was evaporated under ambient conditions. The XRPD pattern for the resulting Form L is shown in FIG. 18. The most prominent X-Ray Powder Diffraction peaks for Form L are shown in Table 19:

TABLE 19

| Angle 2-Theta ° | Intensity Count |
|---|---|
| 7.1 | 13.7 |
| 9.7 | 10.1 |
| 11.1 | 17.9 |
| 14.7 | 17 |
| 18.2 | 20.4 |
| 18.7 | 15.7 |
| 19.6 | 14.8 |
| 21.2 | 25.8 |
| 21.8 | 21.1 |
| 22.9 | 55.4 |
| 23.5 | 21.8 |
| 26.0 | 34.7 |
| 26.9 | 30.4 |
| 27.7 | 24.1 |
| 28.9 | 42.7 |
| 29.5 | 19.8 |
| 33.7 | 11.4 |

Example 17

Preparation of Compound (I) Difumarate Form M

Figure 19:
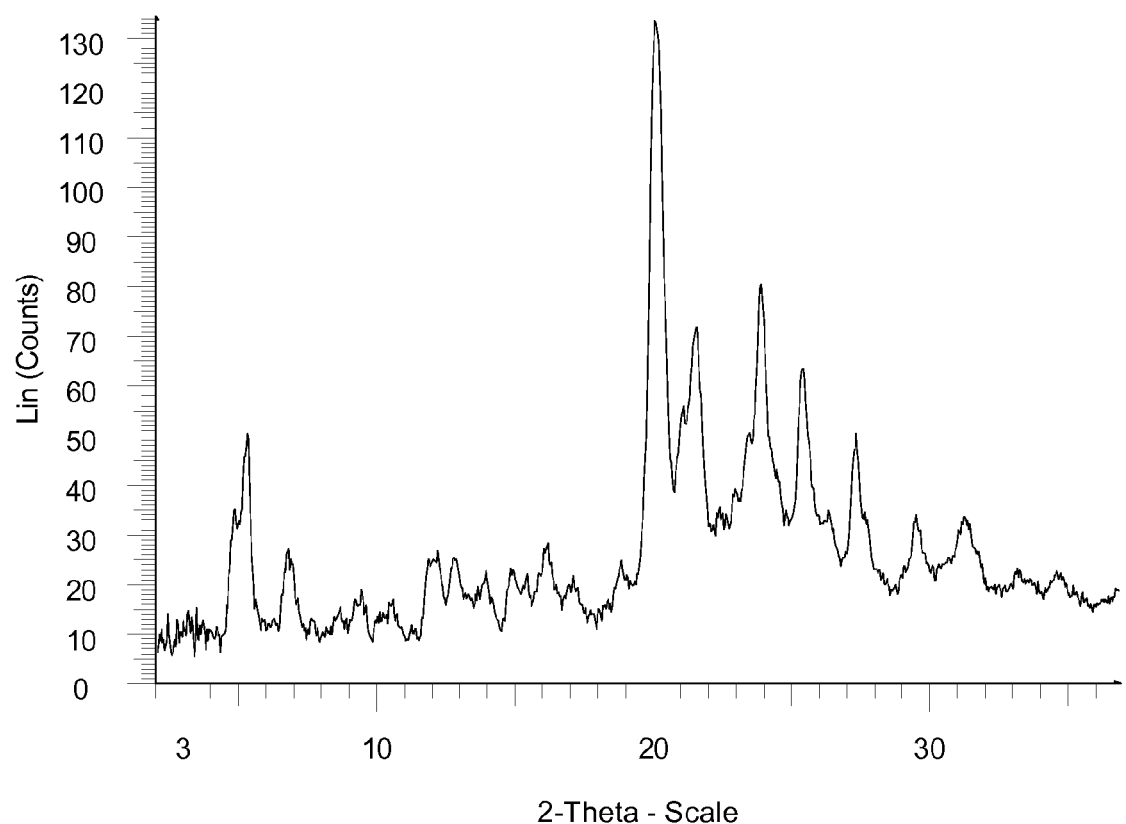
FIG. 19 shows an X-ray powder diffraction pattern for Compound (I) difumarate Form M. The x-axis shows the 2-theta value and the y-axis the counts.

A solution of Compound (I) difumarate was prepared in acetonitrile/water (50/50 v/v) and an aliquot was added to a microplate well. The solvent was evaporated and 2-propanol/water (90/10 v/v), was added to the well. The plate was sonicated and then the solvent was evaporated under ambient conditions. The XRPD pattern for the resulting Form M is shown in FIG. 19. The most prominent X-Ray Powder Diffraction peaks for Form M are shown in Table 20:

TABLE 20

| Angle 2-Theta ° | Intensity Count |
|---|---|
| 5.3 | 41.8 |
| 6.7 | 18.6 |
| 16.1 | 20 |
| 20.1 | 125 |
| 21.5 | 63.3 |
| 23.9 | 72.2 |
| 25.4 | 54.8 |
| 27.4 | 41.9 |
| 29.5 | 25.8 |
| 31.2 | 25.4 |

Example 18

Preparation of Compound (I) Difumarate Form N

Figure 20:
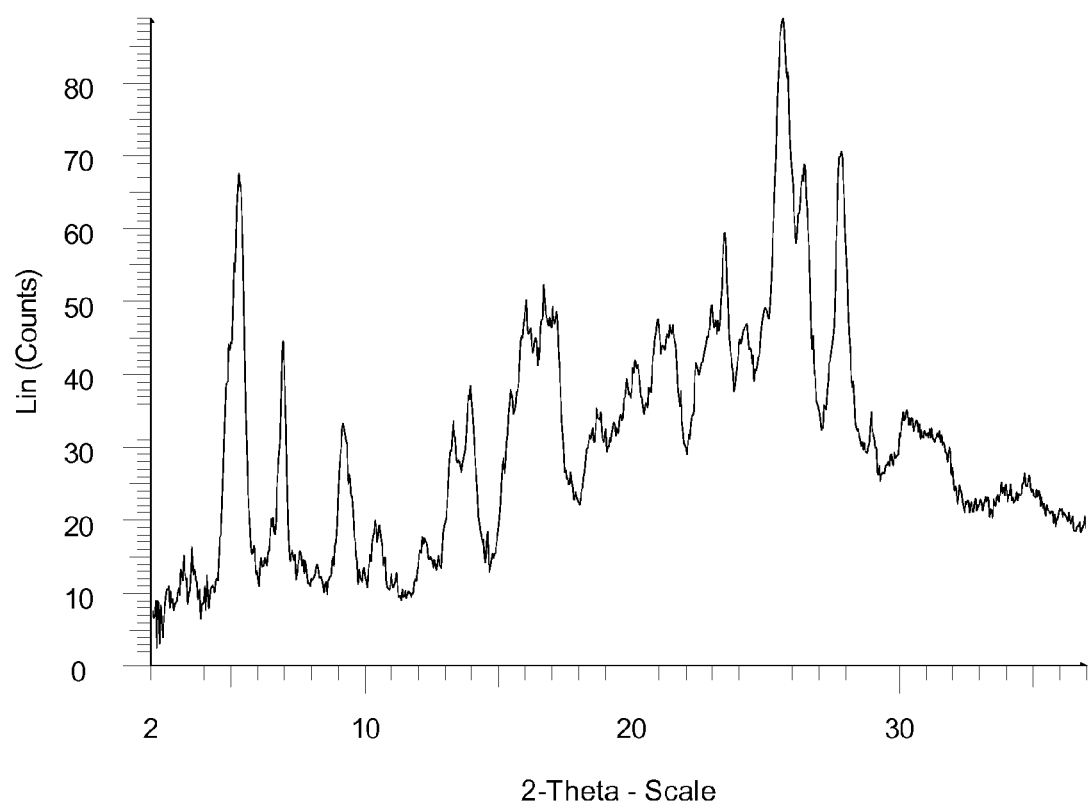
FIG. 20 shows an X-ray powder diffraction pattern for Compound (I) difumarate Form N. The x-axis shows the 2-theta value and the y-axis the counts.

A solution of Compound (I) difumarate was prepared in acetonitrile/water (50/50 v/v) and an aliquot was added to a microplate well. The solvent was evaporated and acetone/water (60/40 v/v), was added to the well. The plate was sonicated and then the solvent was evaporated at 4° C. The XRPD pattern for the resulting Form N is shown in FIG. 20. The most prominent X-Ray Powder Diffraction peaks for Form N are shown in Table 21:

TABLE 21

| Angle 2-Theta ° | Intensity Count |
|---|---|
| 5.3 | 59.2 |
| 6.9 | 36.2 |

TABLE 21-continued

| Angle 2-Theta ° | Intensity Count |
|---|---|
| 9.2 | 23.2 |
| 10.5 | 8.5 |
| 12.2 | 9.01 |
| 13.3 | 25.1 |
| 13.9 | 28.2 |
| 23.5 | 51.1 |
| 25.6 | 80.3 |
| 26.4 | 60.5 |
| 27.8 | 62.3 |

Example 19

Preparation of Compound (I) Difumarate Form O

Figure 21:
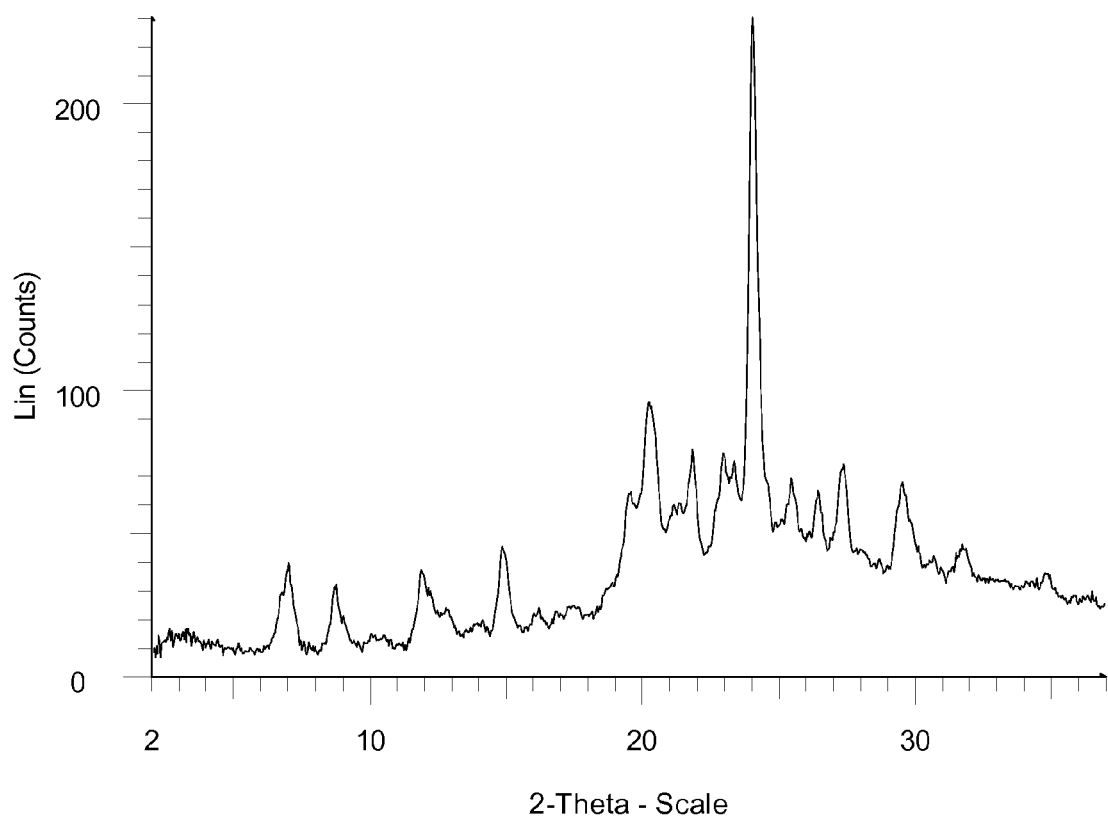
FIG. 21 shows an X-ray powder diffraction pattern for Compound (I) difumarate Form O. The x-axis shows the 2-theta value and the y-axis the counts.

A solution of Compound (I) difumarate was prepared in acetonitrile/water (50/50 v/v) and an aliquot was added to a microplate well. The solvent was evaporated and ethanol/water (30/70 v/v), was added to the well. The plate was sonicated and then the solvent was evaporated at 4° C. The XRPD pattern for the resulting Form O is shown in FIG. 21. The most prominent X-Ray Powder Diffraction peaks for Form O are shown in Table 22:

TABLE 22

| Angle 2-Theta ° | Intensity Count |
|---|---|
| 6.9 | 28.5 |
| 8.7 | 21.7 |
| 11.9 | 27.6 |
| 14.9 | 36.8 |
| 20.2 | 87.4 |
| 21.8 | 70.6 |
| 24.0 | 223 |
| 25.5 | 59.1 |
| 26.4 | 56.2 |
| 27.4 | 63.7 |
| 29.5 | 58.4 |

Example 20

Preparation of Compound (I) Difumarate Form P

Figure 22:
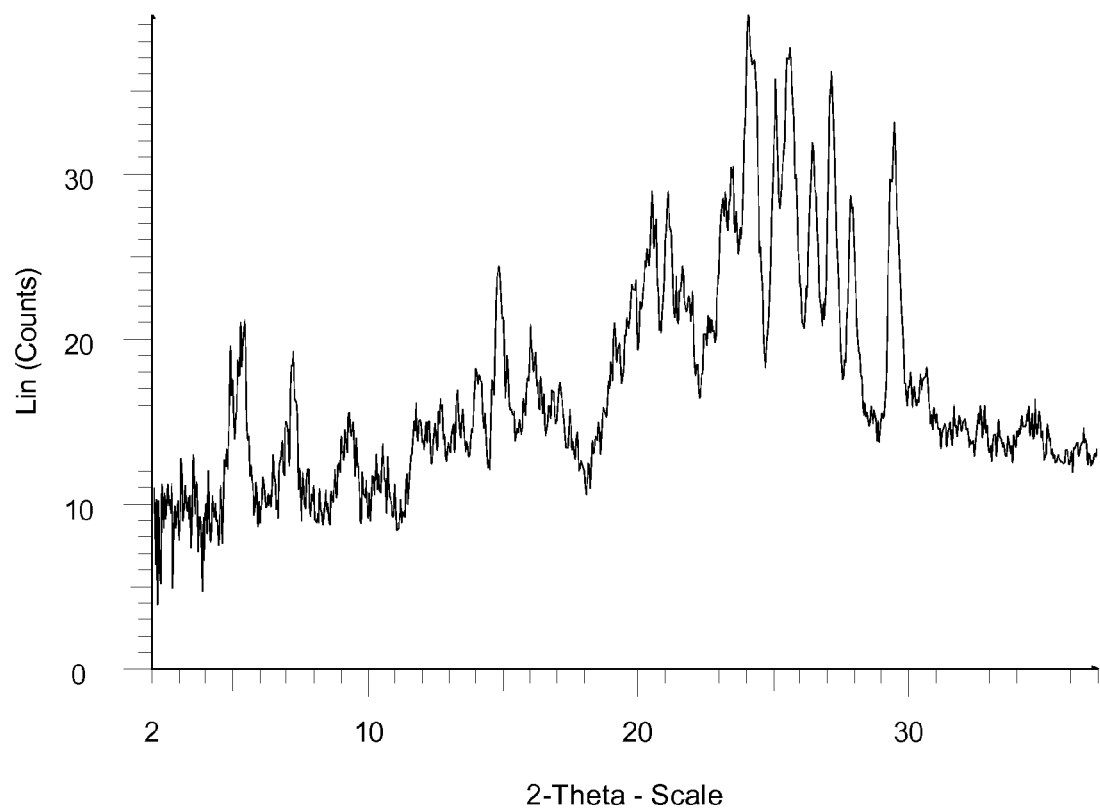
FIG. 22 shows an X-ray powder diffraction pattern for Compound (I) difumarate Form P. The x-axis shows the 2-theta value and the y-axis the counts.

A solution of Compound (I) difumarate was prepared in acetonitrile/water (50/50 v/v) and an aliquot was added to a microplate well. The solvent was evaporated and 2-propanol/water (90/10 v/v) was added to the well. The plate was sonicated and then the solvent was evaporated at 4° C. The XRPD pattern for the resulting Form P is shown in FIG. 22. The most prominent X-Ray Powder Diffraction peaks for Form P are shown in Table 23:

TABLE 23

| Angle 2-Theta ° | Intensity Count |
|---|---|
| 5.3 | 9.97 |
| 7.2 | 9.97 |
| 14.8 | 15.8 |
| 24.1 | 30.6 |
| 25.6 | 29.3 |
| 26.5 | 23.2 |
| 27.2 | 27.9 |

TABLE 23-continued

| Angle 2-Theta ° | Intensity Count |
|---|---|
| 27.9 | 20.3 |
| 29.5 | 23.2 |

Example 21

Preparation of Compound (I) Difumarate Form Q

Figure 23:
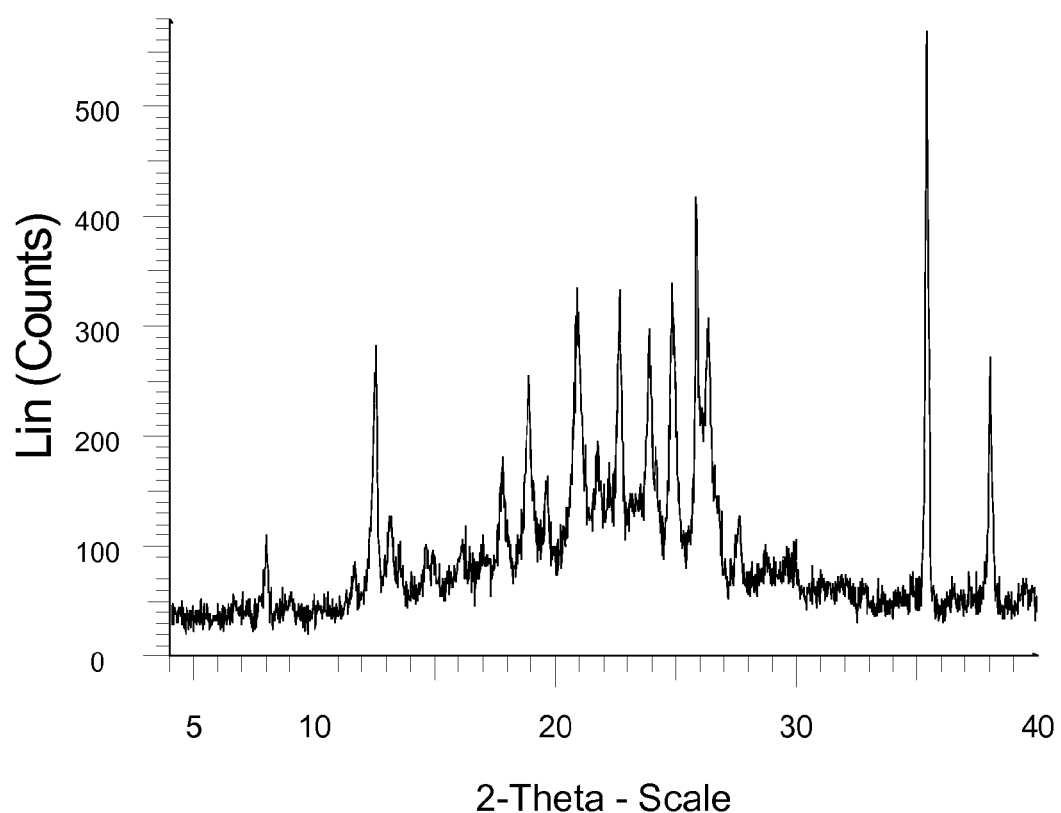
FIG. 23 shows an X-ray powder diffraction pattern for Compound (I) difumarate Form Q. The x-axis shows the 2-theta value and the y-axis the counts.

Form Q was observed when Form B was heated to 150° C. during variable temperature XRPD analysis. The XRPD pattern for Form Q is shown in FIG. 23. The most prominent X-Ray Powder Diffraction peaks for Form Q are shown in Table 24:

TABLE 24

| Angle 2-Theta ° | Intensity Count |
|---|---|
| 8.0 | 92 |
| 12.5 | 210 |
| 17.8 | 130 |
| 18.9 | 212 |
| 20.9 | 318 |
| 22.7 | 316 |
| 23.9 | 272 |
| 24.9 | 290 |
| 25.9 | 358 |
| 26.3 | 280 |
| 27.6 | 110 |
| 35.4 | 552 |
| 38.1 | 244 |

Example 22

Tablet formulation of Compound (I) Difumarate

The powdered ingredients shown below were charged to a mixer and mixed to produce a uniform distribution of Compound (I) difumarate. A binder solution was prepared and added to the powders with further mixing until a suitable wet mass formed. The wet mass was passed through a screen and the resultant granules dried to an appropriate moisture content (for example less than 2% by weight). The dried granules were passed through an appropriately sized screen and blended with magnesium stearate before compressing into tablet cores using conventional tabletting equipment. The compressed cores were then coated with an aqueous suspension of film coating components using a conventional perforated drum coater.

Film-coated tablets containing 2.5, 10, 40 and 100 mg of Compound (I) Difumarate Form A prepared as described above are illustrated in Table 25.

TABLE 25

| Ingredient | Tablet strength[1] | | | |
|---|---|---|---|---|
| | 2.5 mg g/batch | 10 mg g/batch | 40 mg g/batch | 100 mg g/batch |
| Tablet core | | | | |
| Compound (I) Difumarate Form A[2] | 37.25 | 149.0 | 448.1 | 448.1 |
| Lactose (450 mesh) | 782.75 | 671.0 | 371.9 | 371.9 |
| Microcrystalline cellulose (PH101) | 100.0 | 100.0 | 100.0 | 100.0 |
| Crospovidone | 50.0 | 50.0 | 50.0 | 50.0 |
| Polyvidone | 20.0 | 20.0 | 20.0 | 20.0 |
| Magnesium stearate | 10.0 | 10.0 | 10.0 | 10.0 |
| Core tablet weight | 100 mg | 100 mg | 133 mg | 333 mg |
| Tablet coating | | | | |
| Opadry White (03B28460) | 23.0 | 23.0 | 23.3 | 23.0 |
| Hypromellose[3] | 15.0 | 15.0 | 15.0 | 15.0 |
| Titanium dioxide[3] | 5.0 | 5.0 | 5.3 | 5.0 |
| Macrogol 300[3] | 3.0 | 3.0 | 3.0 | 3.0 |
| Purified water[4] | 177.0 | 177.0 | 176.7 | 177.0 |
| Nominal coated tablet weight | 102.1 mg | 102.1 mg | 136.1 mg | 140.6 mg |

[1]Tablet strengths refer to the equivalent amount of Compound (I) free base present in the tablet.
[2]The Compound (I) difumarate was micronised prior to formulation to give an average particle size of less than about 5 μm.
[3]The hypromellose, macrogol 300 and titanium dioxide are included as Opadry White (03B28460), supplied by Colorcon.
[4]Purified water is used as the solvent/carrier fluid during film-coating and is removed during the coating process.

A suitable manufacturing process is outlined below:

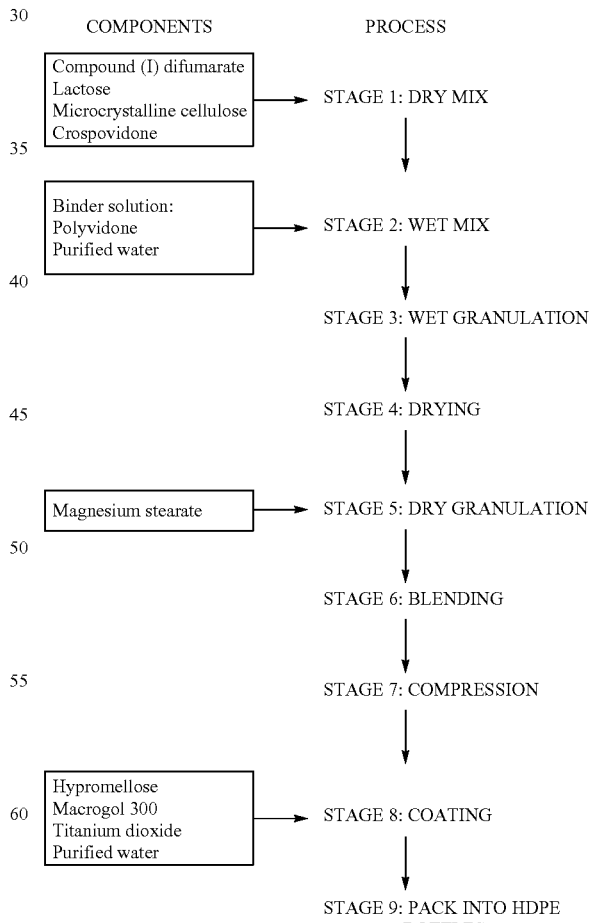

The invention claimed is:

1. Crystalline 4-(3-chloro-2-fluoroanilino)-7 methoxy-6-{[1-(N-methylcarbamoylmethyl)piperidin-4-yl]oxy}quinazoline difumarate Form A, wherein said Form A has an X-ray powder diffraction pattern with specific peaks at about 2-theta=26.4°, 14.9° and 7.1°.

2. A method of treating a cancer in a mammal comprising administering an effective amount of crystalline 4-(3-chloro-2-fluoroanilino)-7 methoxy-6-{[1-(N-methylcarbamoylmethyl)piperidin-4-yl]oxy}quinazoline difumarate Form A to the mammal, wherein said Form A has an X-ray powder diffraction pattern with specific peaks at about 2-theta=26.4°, 14.9° and 7.1° and wherein the cancer is breast cancer.

3. The method of claim 2, wherein the crystalline 4-(3-chloro-2-fluoroanilino)-7 methoxy-6-{[1-(N-methylcarbamoylmethyl)piperidin-4-yl]oxy}quinazoline difumarate Form A is used in combination with a taxane.

4. The method of claim 2, wherein the breast cancer has a low over-expression of erbB2.

5. The method of claim 2, wherein the method comprises adjuvant treatment of hormone sensitive breast cancer.

6. The method of claim 2, wherein the method comprises adjuvant treatment of estrogen receptor positive breast cancer in post-menopausal women.

* * * * *